US008663651B2

(12) United States Patent
Peled et al.

(10) Patent No.: US 8,663,651 B2
(45) Date of Patent: Mar. 4, 2014

(54) T-140 PEPTIDE ANALOGS HAVING CXCR4 SUPER-AGONIST ACTIVITY FOR IMMUNOMODULATION

(75) Inventors: Amnon Peled, Tel Aviv (IL); Michal Begin, Jerusalem (IL); Katia Beider, Jerusalem (IL); Michal Abraham, Mevaseret Zion (IL)

(73) Assignee: Biokine Therapeutics Ltd., Nes Ziona (IL)

( * ) Notice: Subject to any disclaimer, the term of this patent is extended or adjusted under 35 U.S.C. 154(b) by 662 days.

(21) Appl. No.: 12/520,811

(22) PCT Filed: Dec. 23, 2007

(86) PCT No.: PCT/IL2007/001598
§ 371 (c)(1),
(2), (4) Date: Feb. 16, 2010

(87) PCT Pub. No.: WO2008/075371
PCT Pub. Date: Jun. 26, 2008

(65) Prior Publication Data
US 2010/0143334 A1    Jun. 10, 2010

Related U.S. Application Data

(60) Provisional application No. 60/876,145, filed on Dec. 21, 2006.

(51) Int. Cl.
*A61K 31/00* (2006.01)
*A61K 38/00* (2006.01)
*A61K 39/00* (2006.01)
*A61K 39/38* (2006.01)
*A61K 39/385* (2006.01)
*A01N 61/00* (2006.01)

(52) U.S. Cl.
USPC .............. 424/196.11; 424/184.1; 424/185.1; 424/192.1; 424/193.1; 514/1; 514/1.1; 514/19.2; 514/19.3; 514/21.5

(58) Field of Classification Search
USPC ........ 424/184.1, 185.1, 192.1, 193.1, 196.11; 514/1, 1.1, 19.2, 19.3, 21.5
See application file for complete search history.

(56) References Cited

U.S. PATENT DOCUMENTS

| | | | |
|---|---|---|---|
| 4,179,337 A | 12/1979 | Davis et al. | |
| 4,342,828 A | 8/1982 | Takaku et al. | |
| 5,206,018 A | 4/1993 | Sehgal et al. | |
| 5,250,732 A | 10/1993 | Kogan et al. | |
| 5,492,126 A | 2/1996 | Hennige et al. | |
| 5,595,756 A | 1/1997 | Bally et al. | |
| 6,128,522 A | 10/2000 | Acker et al. | |
| 6,365,583 B1 | 4/2002 | MacFarland et al. | |
| 6,576,875 B1 | 6/2003 | Kleffner et al. | |
| 6,747,036 B2 | 6/2004 | Gourdeau et al. | |
| 6,875,738 B1 | 4/2005 | Clark-Lewis et al. | |
| 6,946,445 B1 | 9/2005 | Clark-Lewis et al. | |
| 7,138,488 B2 | 11/2006 | Fujii | |
| 7,169,750 B2 | 1/2007 | Bridger et al. | |
| 7,291,631 B2 | 11/2007 | Bridger et al. | |
| 7,419,667 B2 | 9/2008 | Hatake et al. | |
| 7,423,007 B2 | 9/2008 | Fujii et al. | |
| 7,595,298 B2 | 9/2009 | Fujii | |
| 7,630,750 B2 | 12/2009 | Liang et al. | |
| 8,017,585 B2 | 9/2011 | Fujii et al. | |
| 2002/0156034 A1 | 10/2002 | Tudan et al. | |
| 2002/0159996 A1 | 10/2002 | Hariharan et al. | |
| 2004/0116655 A1* | 6/2004 | Fujii | ............................. 530/326 |
| 2004/0209921 A1 | 10/2004 | Bridger et al. | |
| 2005/0002939 A1 | 1/2005 | Zlotnik et al. | |
| 2005/0043367 A1 | 2/2005 | Bridger et al. | |
| 2006/0008465 A1 | 1/2006 | Steinaa et al. | |
| 2006/0079492 A1 | 4/2006 | Ahlem et al. | |
| 2006/0264378 A1 | 11/2006 | Fujii et al. | |
| 2006/0264605 A1 | 11/2006 | Fujii | |
| 2007/0119969 A1 | 5/2007 | Collins, Jr. et al. | |
| 2007/0129760 A1 | 6/2007 | Demarais et al. | |
| 2007/0167459 A1 | 7/2007 | Habashita et al. | |
| 2008/0233053 A1 | 9/2008 | Gross et al. | |
| 2009/0181897 A1 | 7/2009 | Fujii et al. | |
| 2010/0143334 A1 | 6/2010 | Peled et al. | |
| 2010/0166715 A1 | 7/2010 | Peled et al. | |
| 2010/0184694 A1 | 7/2010 | Peled et al. | |
| 2010/0222256 A1 | 9/2010 | Fujii | |
| 2011/0269686 A1 | 11/2011 | Fujii et al. | |
| 2012/0094907 A1 | 4/2012 | Abraham et al. | |
| 2012/0207748 A1 | 8/2012 | Peled et al. | |

FOREIGN PATENT DOCUMENTS

| | | |
|---|---|---|
| CA | 1297007 | 3/1992 |
| EP | 0243153 | 10/1987 |
| EP | 0396158 | 11/1990 |
| EP | 0215126 | 7/1991 |
| EP | 0220520 | 9/1991 |
| EP | 0459516 | 12/1991 |
| EP | 0459795 | 12/1991 |

(Continued)

OTHER PUBLICATIONS

Requisition—Sequence Listing Dated May 9, 2013 From the Canadian Intellectual Property Office Re. Application No. 2,673,719.
Requisition by the Examiner Dated Jun. 18, 2013 From the Canadian Intellectual Property Office Re. Application No. 2,673,484.
Restriction Official Action Dated Dec. 28, 2011 From the US Patent and Trademark Office Re. U.S. Appl. No. 12/520,803.
Official Action Dated Dec. 7, 2012 From the US Patent and Trademark Office Re. U.S. Appl. No. 12/520,699.
Official Action Dated Sep. 12, 2012 From the US Patent and Trademark Office Re. U.S. Appl. No. 12/520,803.
Official Action Dated May 6, 2013 From the US Patent and Trademark Office Re. U.S. Appl. No. 13/360,751.
International Search Report and the Written Opinion Dated Jun. 24, 2009 From the International Searching Authority Re. Application No. PCT/IL2007/001597.

(Continued)

*Primary Examiner* — Alana Harris Dent

(57) ABSTRACT

The present invention is directed to novel therapeutic uses of T-140 analog peptides and compositions comprising same. Specifically, the invention provides compositions and methods useful for immunomodulation.

2 Claims, 7 Drawing Sheets

(56) References Cited

FOREIGN PATENT DOCUMENTS

| | | |
|---|---|---|
| EP | 0231819 | 4/1992 |
| EP | 0355811 | 12/1993 |
| EP | 0373679 | 6/1994 |
| EP | 0331186 | 8/1994 |
| EP | 0344796 | 9/1994 |
| EP | 0263490 | 1/1995 |
| EP | 0230980 | 3/1996 |
| EP | 0401384 | 3/1996 |
| EP | 0272703 | 10/1997 |
| EP | 0370205 | 7/1998 |
| EP | 0459630 | 8/1998 |
| EP | 0217404 | 1/1999 |
| EP | 0237545 | 8/1999 |
| EP | 0169566 | 7/2000 |
| EP | 0335423 | 3/2003 |
| EP | 1323730 | 7/2003 |
| EP | 0473268 | 10/2003 |
| EP | 2058395 | 5/2009 |
| JP | 2002-506830 | 3/2002 |
| JP | 2002-247843 | 8/2002 |
| WO | WO 91/07988 | 6/1991 |
| WO | WO 93/15211 | 8/1993 |
| WO | WO 95/10534 | 4/1995 |
| WO | WO 99/47158 | 9/1999 |
| WO | WO 00/06086 | 2/2000 |
| WO | WO 00/09152 | 2/2000 |
| WO | WO 01/38352 | 5/2001 |
| WO | WO 01/64716 | 9/2001 |
| WO | WO 01/85196 | 11/2001 |
| WO | WO 02/20561 | 3/2002 |
| WO | WO 2004/020462 | 3/2004 |
| WO | WO 2004/024178 | 3/2004 |
| WO | WO 2004/087068 | 10/2004 |
| WO | WO 2008/017025 A2 * | 2/2008 |
| WO | WO 2008/075369 | 6/2008 |
| WO | WO 2008/075370 | 6/2008 |
| WO | WO 2008/075371 | 6/2008 |
| WO | WO 2010/146578 | 12/2010 |
| WO | WO 2010/146584 | 12/2010 |
| WO | WO 2012/095849 | 7/2012 |
| WO | WO 2013/160895 | 10/2013 |

OTHER PUBLICATIONS

Notice of Allowance Dated Feb. 8, 2013 From the US Patent and Trademark Office Re. U.S. Appl. No. 12/520,699.
Notice of Allowance Dated Jan. 4, 2013 From the US Patent and Trademark Office Re. U.S. Appl. No. 12/583,746.
Notice of Allowance Dated Dec. 10, 2012 From the US Patent and Trademark Office Re. U.S. Appl. No. 13/178,737.
Advisory Action Before the Filing of an Appeal Brief Dated Nov. 16, 2012 From the US Patent and Trademark Office Re. U.S. Appl. No. 12/520,699.
Office Action Dated Mar. 13, 2013 From the Israel Patent Office Re. Application No. 199468 and Its Translation Into English.
Notification of Office Action and Search Report Dated Mar. 6, 2013 From the State Intellectual Property Office of the People's Republic of China Re. Application No. 201080035931.5 and Its Summary in English.
Kucia et al. "Trafficking of Normal Stem Cells and Metastasis of Cancer Stem Cells Involve Similar Mechanisms: Pivotal Role of the SDF-1—CXCR4 Axis", Stem Cells, 23(7): 879-894, Aug. 2005.
Voermans et al. "Migratory Behavior of Leukemic Cells From Acute Myeloid Leukemia Patients", Leukemia, 16(4): 650-657, Apr. 2002.
Translation of Office Action Dated Feb. 1, 2013 From the Japanese Patent Office Re. Application No. 2011-060367.
HIV "Report of the Investigation for Development of HIV Medicaments (Year 2000)" p. 16-21, 2001. Japanese Only!
Translation of Notification of Office Action Dated Mar. 6, 2013 From the State Intellectual Property Office of the People's Republic of China Re. Application No. 201080035931.5.
Translation of Search Report Dated Mar. 6, 2013 From the State Intellectual Property Office of the People's Republic of China Re. Application No. 201080035931.5.

Communication Pursuant to Rules 70(2) and 70a(2) EPC Dated Jan. 22, 2013 From the European Patent Office Re. Application No. 10789103.8.
Official Action Dated Jan. 29, 2013 From the US Patent and Trademark Office Re. U.S. Appl. No. 13/360,751.
Communication Pursuant to Article 94(3) EPC Dated May 3, 2013 From the European Patent Office Re. Application No. 10176632.7.
Official Action Dated Apr. 24, 2013 From the US Patent and Trademark Office Re. U.S. Appl. No. 13/360,751.
Restriction Official Action Dated Mar. 1, 2012 From the US Patent and Trademark Office Re. U.S. Appl. No. 12/520,699.
Esler et al. "Renal Sympathetic Denervation in Patients With Treatment-Resistant Hypertension (The Symplicity HTN-2 Trial): A Randomised Controlled Trial", The Lancet, 376: 1903-1909, Published Online Nov. 17, 2010.
Requisition—Sequence Listing Dated Jan. 5, 2011 From the Canadian Intellectual Property Office Re. Application No. 2,673,719.
Response Dated Mar. 22, 2011 to Requisition—Sequence Listing of Jan. 5, 2011 From the Canadian Intellectual Property Office Re. Application No. 2,673,719.
Official Action Dated Sep. 5, 2012 From the US Patent and Trademark Office Re. U.S. Appl. No. 12/520,699.
Official Action Dated Sep. 10, 2012 From the US Patent and Trademark Office Re. U.S. Appl. No. 12/583,746.
HIV "Strategic Generation of Anti-AIDS Agents Based on HIV Secondary Receptor Antagonists and Modification of the Agents for Pharmaceutical Use", Report of the Investigation for Development of HIV Medicaments (Year 2000), p. 16-21, 2001. English Translation.
Tamamura et al. "Development of Selective Antagonists Against an HIV Second Receptor", Yakugaku Zasshi, 121(11): 781-792, 2001. English Translation.
Official Action Dated Mar. 5, 2012 From the US Patent and Trademark Office Re. U.S. Appl. No. 12/520,803.
Heredia et al. "Rapamycin Causes Down-Regulation of CCR5 and Accumulation of Anti-HIV Beta-Chemokines: An Approach to Suppress R5 Strains of HIV-1", Proc. Natl. Acad. Sci. USA, PNAS, 100(18): 10411-10416, Sep. 2, 2003.
Ulvatne et al. "Short Antibacterial Peptides and Erythromycin Act Synergically Against *Escherichia coli*", Journal of Antimicrobial Chemotherapy, 48: 203-208, 2001.
International Preliminary Report on Patentability Dated Jun. 24, 2009 From the International Bureau of WIPO Re. Application No. PCT/IL2007/001596.
International Preliminary Report on Patentability Dated Jun. 24, 2009 From the International Bureau of WIPO Re. Application No. PCT/IL2007/001598.
International Search Report and the Written Opinion Dated Jun. 4, 2008 From the International Searching Authority Re. Application No. PCT/IL2007/001598.
International Search Report and the Written Opinion Dated Dec. 5, 2008 From the International Searching Authority Re. Application No. PCT/IL2007/001596.
Respone Dated Jan. 4, 2012 to Office Action of Sep. 4, 2011 From the Israel Patent Office Re. Application No. 199468 and Its Translation Into English.
Official Action Dated May 4, 2012 From the US Patent and Trademark Office Re. U.S. Appl. No. 12/520,699.
Bork "Powers and Pitfalls in Sequence Analysis: The 70% Hurdle", Genome Research, 10: 398-400, 2000.
Brenner "Errors in Genome Annotation", Trends in Genetics, TIG, 15(4): 132-133, Apr. 1999.
Doerks et al. "Protein Annotation: Detective Work for Function Predicition", Trends in Genetics, 14(6): 248-250, Jun. 1998.
Ngo et al. "Computational Complexity, Protein Structure Prediction, and the Levinthal Paradox", The Protein Folding Problem and Tertiary Structure Prediction, Chap.14: 433-440, 492-495, 1994.
Skolnick et al. "From Genes to Protein Structure and Function: Novel Applications of Computational Approaches in the Genomic Era", Trends in Biotechnology, TIBTECH, 18(1): 34-39, Jan. 2000.
Wells "Additivity of Mutational Effects in Proteins", Biochemistry, 29(37): 8509-8517, Sep. 18, 1990.
AACR "97th Annual Meeting 2006: Publications", AACR, American Association fo Cancer Research, Retreived From the Internet, 2006.

(56) References Cited

OTHER PUBLICATIONS

Avniel et al. "Involvement of the CXCL12/CXCR4 Pathway in the Recovery of Skin Following Burns", Journal of Investigative Dermatology, 126(2): 468-476, 2006.
Balkwill "The Significance of Cancer Cell Expression of the Chemokine Receptor CXCR4", Seminars in Cancer Biology, 14: 171-179, 2004.
Broxmeyer et al. "Rapid Mobilization of Murine and Human Hematopoietic Stem and Progenitor Cells With AMD3100, A CXCR4 Antagonist", The Journal of Experimental Medicine, 201(8): 1307-1318, Apr. 18, 2005.
Dar et al. "Chemokine Receptor CXCR4-Dependent Internalization and Resecretion of Functional Chemokine SDF-1 by Bone Marrow Endothelial and Stromal Cells", Nature Immunology, 6(10): 1038-1046, Oct. 2005.
Darash-Yahana et al. "Role of High Expression Levels of CXCR4 in Tumor Growth, Vascularization, and Metastasis", The FASEB Journal, 18: 1240-1242, 2004.
Flomenberg et al. "The Use of AMD3100 Plus G-CSF for Autologous Hematopoietic Progenitor Cell Mobilization Is Superior to G-CSF Alone", Blood, 106(5): 1867-1874, 2005.
Kim et al. "In Vitro Behavior of Hematopoietic Progenitor Cells Under the Influence of Chemoattractants: Stromal Cell-DErived Factor-1, Steel Factor, and the Bone Marrow Environment", Blood, 91(1): 100-110, 1998.
Kollet et al. "Human CD34+CXCR4-Sorted Cells Harbor Intracellular CXCR4, Which Can Be Functionally Expressed and Provide NOD/SCID Repopulation", Blood, 100(8): 2778-2786, 2002.
Lack et al. "A Pharmacokinetic-Pharmacodynamic Model for the Mobilization of CD34+ Hematopoietic Progenitor Cells by AMD3100", Clinical Pharmacology and Therapeutics, 77(5): 427-436, 2005.
Lapidot et al. "How Do Stem Cells Find Their Way Home?", Blood, 106(6): 1901-1910, 2005.
Lapidot et al. "The Essential Roles of the Chemokine SDF-1 and Its Receptor CXCR4 in Human Stem Cell Homing and Repopulation of Transplanted Immune-Deficient NOD/SCID and NOD/SCID/B2m<Null> Mice", Leukemia, 16(10): 1992-2003, 2002.
Levesque et al. "Disruption of the CXCR4/CXCL12 Chemotactic Interaction During Hematopoietic Stem Cell Mobilization Induced by GCSF or Cyclophosphamide", Journal of Clinical Investigation, 111(2): 187-196, Jan. 2003.
Martin et al. "Chemokines Acting Via CXCR2 and CXCR4 Control the Release of Neutrophils From the Bone Marrow and Their Return Following Senescence", Immunity, 19(4): 583-593, Oct. 2003.
Mueller et al. "Involvement of Chemokine Receptors in Breast Cancer Metastasis", Nature, 410: 50-56, Mar. 2001.
Nagasawa et al. "Molecular Cloning and Structure of a Pre-B-Cell Growth-Stimulating Factor", Proc. Natl. Acad. sci. USA, 91: 2305-2309, Mar. 1994.
Peled et al. "Dependence of Human Stem Cell Engraftment and Repopulation of NOD/SCIDMice on CXCR4", Science, 283(5403): 845-848, 1999.
Phillips et al. "The Stromal Derived Factor-1/CXCL12-CXC Chemokine Receptor 4 Biological Axis in Non-Small Cell Lung Cancer Metastatis", 167: 1676-1686, 2003.
Princen et al. "HIV Chemokine Receptor Inhibitors as Novel Anti-HIV Drugs", Cytokine & Growth Factor Reviews, 16(6): 659-677, 2005.
Rossi et al. "The Biology of Chemokines and Their Receptors", Annual Reviews of Immunology, 18: 217-242, 2000.
Tamamura et al. "A Low-Molecular-Weight Inhibitor Against the Chemokine Receptor CXCR4: A Strong Anti-HIV Paptide T140", Biochemical and Biophysical Research Communications, 253(3): 877-882, 1998.
Tamamura et al. "Enhancement of the T140-Based Pharmacophores Leads to the Development of More Potent and Bio-Stable CXCR4 Antagonists", Organic Biomolecular Chemistry, 1: 3663-3669, 2003.
Tamamura et al. "The Therapeutic Potential of CXCR4 Antagonists in the Treatment of HIV Infection, Cancer Metastasis and Rheumatoid Arthritis", Expert Opinion of Therapeutic Targets, 9(6): 1267-1282, 2005.
Zannettino et al. "Elevated Serum Levels of Stromal-Derived Factor-1Alpha Are Associated With Increased Osteoclast Activity and Osteolytic Bone Disease in Multiple Myeloma Patients", Cancer Research, 65(5): 1700-1709, Mar. 1, 2005.
Zhou et al. "CXCR4 Is a Major Chemokine Receptor on Glioma Cells and Mediates Their Survival", The Journal of Biological Chemistry, 277(51): 49481-49487, Dec. 29, 2002.
Zuluaga et al. "Neutropenia Induced in Outbred Mice by a Simplified Low-Dose Cyclophosphamide Regimen: Characterization and Applicability to Diverse Experimental Models of Infectious Diseases", BMC Infectious Diseases, 6(55): 1-10, Mar. 17, 2006.
Amendment Dated May 15, 2008 After Notice of Allowance of Apr. 14, 2008 From the US Patent and Trademark Office Re. U.S. Appl. No. 10/525,838.
Communication Pursuant to Article 94(3) EPC Dated Oct. 4, 2010 From the European Patent Office Re. Application No. 03791288.8.
Communication Pursuant to Article 94(3) EPC Dated Apr. 9, 2008 From the European Patent Office Re. Application No. 03791288.8.
Communication Pursuant to Article 94(3) EPC Dated Dec. 15, 2008 From the European Patent Office Re. Application No. 03791288.8.
Communication Pursuant to Article 94(3) EPC Dated Sep. 15, 2009 From the European Patent Office Re. Application No. 03791288.8.
Communication Pursuant to Article 96(2) EPC Dated Feb. 6, 2006 From the European Patent Office Re. Application No. 10963414.6.
Communication Pursuant to Article 96(2) EPC Dated Mar. 17, 2005 From the European Patent Office Re. Application No. 10963414.6.
Communication Pursuant to Article 96(2) EPC Dated Jul. 18, 2006 From the European Patent Office Re. Application No. 10963414.6.
Communication Pursuant to Article 96(2) EPC Dated Jul. 26, 2007 From the European Patent Office Re. Application No. 10963414.6.
Communication Pursuant to Rule 69 EPC—Reminder Concerning Payment of the Designation Fee (Art. 79(2) EPC) and of the Examination Fee (Art. 94(1) Epc)—and Invitation Pursuant to Rule 70a(1) EPC Dated Mar. 12, 2012 From the European Patent Office Re. Application No. 10176632.7.
Communication Under Rule 71(3) EPC Dated Apr. 16, 2012 From the European Patent Office Re. Application No. 03791288.8.
European Search Report and the European Search Opinion Dated Feb. 3, 2012 From the European Patent Office Re. Application No. 10176632.7.
International Preliminary Report on Patentability Dated Apr. 19, 2002 From the International Preliminary Examining Authority Re. PCT/JP2001/007668.
International Preliminary Report on Patentability Dated Aug. 19, 2004 From the International Preliminary Examining Authority Re. Application No. PCT/JP2003/010753.
International Preliminary Report on Patentability Dated Dec. 29, 2011 From the International Bureau of WIPO Re. Application No. PCT/IL2010/000466.
International Search Report and the Written Opinion Dated Oct. 15, 2010 From the International Searching Authority Re. Application No. PCT/IL2010/000466.
International Search Report and the Written Opinion Dated May 30, 2012 From the International Searching Authority Re. Application No. PCT/IL2012/050008.
International Search Report Dated Nov. 4, 2003 From the International Searching Authority Re. Application No. PCT/JP2003/010753.
International Search Report Dated Dec. 11, 2001 From the International Searching Authority Re. Application No. PCT/JP2001/007668.
Interview Summary Dated May 3, 2005 From the US Patent and Trademark Office Re. U.S. Appl. No. 10/363,209.
Interview Summary Dated Feb. 21, 2006 From the US Patent and Trademark Office Re. U.S. Appl. No. 10/363,209.
Notice of Allowance Dated Mar. 9, 2006 From the US Patent and Trademark Office Re. U.S. Appl. No. 10/363,209.
Notice of Allowance Dated Apr. 11, 2011 From the US Patent and Trademark Office Re. U.S. Appl. No. 12/172,007.

(56) References Cited

OTHER PUBLICATIONS

Notice of Allowance Dated Apr. 14, 2008 From the US Patent and Trademark Office Re. U.S. Appl. No. 10/525,838.
Notice of Allowance DAted May 21, 2009 From the US Patent and Trademark Office Re. U.S. Appl. No. 11/497,225.
Official Action Dated Jul. 1, 2010 From the US Patent and Trademark Office Re. U.S. Appl. No. 12/172,007.
Official Action Dated Nov. 3, 2005 From the US Patent and Trademark Office Re. U.S. Appl. No. 10/363,209.
Official Action Dated Jul. 11, 2007 From the US Patent and Trademark Office Re. U.S. Appl. No. 10/525,838.
Official Action Dated Jun. 15, 2005 From the US Patent and Trademark Office Re. U.S. Appl. No. 10/363,209.
Official Action Dated May 18, 2012 From the US Patent and Trademark Office Re. U.S. Appl. No. 13/178,737.
Official Action Dated Jan. 24, 2011 From the US Patent and Trademark Office Re. U.S. Appl. No. 12/172,007.
Official Action Dated Aug. 28, 2008 From the US Patent and Trademark Office Re. U.S. Appl. No. 11/497,225.
Official Action Dated Dec. 28, 2011 From the US Patent and Trademark Office Re. U.S. Appl. No. 12/583,746.
Requisition by the Examiner Dated Jul. 6, 2012 From the Canadian Intellectual Property Office Re. Application No. 2,421,183.
Requisition by the Examiner Dated Mar. 8, 2011 From the Canadian Intellectual Property Office Re. Application No. 2,421,183.
Requisition by the Examiner Dated Oct. 17, 2011 From the Canadian Intellectual Property Office Re. Application No. 2,537,158.
Requisition by the Examiner Dated May 19, 2011 From the Canadian Intellectual Property Office Re. Application No. 2,421,183.
Requisition by the Examiner Dated Aug. 25, 2009 From the Canadian Intellectual Property Office Re. Application No. 2,421,183.
Requisition by the Examiner Dated May 25, 2010 From the Canadian Intellectual Property Office Re. Application No. 2,537,158.
Response Dated Jul. 1, 2005 to Communication Pursuant to Article 96(2) EPC of Mar. 17, 2005 From the European Patent Office Re. Application No. 10963414.6.
Response Dated Nov. 1, 2010 to Official Action of Jul. 1, 2010 From the US Patent and Trademark Office Re. U.S. Appl. No. 12/172,007.
Response Dated Feb. 3, 2006 to Official Action of Nov. 3, 2005 From the US Patent and Trademark Office Re. U.S. Appl. No. 10/363,209.
Response Dated Jun. 4, 2008 to Restriction Official Action of Apr. 8, 2008 From the US Patent and Trademark Office Re. U.S. Appl. No. 11/497,225.
Response Dated Sep. 7, 2011 to Requisition by the Examiner of Mar. 8, 2011 From the Canadian Intellectual Property Office Re. Application No. 2,421,183.
Response Dated Dec. 8, 2009 to Office Action of Aug. 11, 2009 From the Japanese Patent Office Re. Application No. 2003-301176.
Response Dated Jan. 8, 2008 to Official Action of Jul. 11, 2007 From the US Patent and Trademark Office Re. U.S. Appl. No. 10/525,838.
Response Dated May 9, 2006 to Communication Pursuant to Article 96(2) EPC of Feb. 6, 2006 From the European Patent Office Re. Application No. 10963414.6.
Response Dated Jun. 10, 2009 to Restriction Official Action of Mar. 26, 2009 From the US Patent and Trademark Office Re. U.S. Appl. No. 12/172,007.
Response Dated Oct. 12, 2010 to Communication Pursuant to Article 94(3) EPC of Oct. 4, 2010 From the European Patent Office Re. Application No. 03791288.8.
Response Dated Oct. 14, 2011 to Restriction Official Action of Sep. 14, 2011 From the US Patent and Trademark Office Re. U.S. Appl. No. 12/583,746.
Response Dated Apr. 15, 2009 to Communication Pursuant to Article 94(3) EPC of Dec. 15, 2008 From the European Patent Office Re. Application No. 03791288.8.
Response Dated Oct. 15, 2008 to Communication Pursuant to Article 94(3) EPC of Apr. 9, 2008 From the European Patent Office Re. Application No. 03791288.8.
Response Dated Sep. 15, 2005 to Official Action of Jun. 15, 2005 From the US Patent and Trademark Office Re. U.S. Appl. No. 10/363,209.
Response Dated Nov. 16, 2007 to Communication Pursuant to Article 96(2) EPC of Jul. 26, 2007 From the European Patent Office Re. Application No. 10963414.6.
Response Dated Apr. 18, 2005 to Restriction Official Action of Mar. 18, 2005 From the US Patent and Trademark Office Re. U.S. Appl. No. 10/363,209.
Response Dated Jan. 21, 2010 to Communication Pursuant to Article 94(3) EPC of Sep. 15, 2009 From the European Patent Office Re. Application No. 03791288.8.
Response Dated Mar. 23, 2011 to Official Action of Jan. 24, 2011 From the US Patent and Trademark Office Re. U.S. Appl. No. 12/172,007.
Response Dated Feb. 24, 2010 to Requisition by the Examiner of Aug. 25, 2009 From the Canadian Intellectual Property Office Re. Application No. 2,421,183.
Response Dated May 25, 2007 to Restriction Official Action of Feb. 6, 2007 From the US Patent and Trademark Office Re. U.S. Appl. No. 10/525,838.
Response Dated Nov. 25, 2011 to Requisition by the Examiner of May 25, 2010 From the Canadian Intellectual Property Office Re. Application No. 2,537,158.
Response Dated Jan. 26, 2009 to Official Action of Aug. 28, 2008 From the US Patent and Trademark Office Re. U.S. Appl. No. 11/497,225.
Response Dated Jan. 29, 2007 to Communication Pursuant to Article 96(2) EPC of Jul. 18, 2006 From the European Patent Office Re. Application No. 10963414.6.
Response Dated Jun. 30, 2010 to Requisition by the Examiner of May 19, 2011 From the Canadian Intellectual Property Office Re. Application No. 2,421,183.
Response Dated Jan. 31, 2011 to Office Action of Oct. 19, 2010 From the Japanese Patent Office Re. Application No. 2003-301176.
Restriction Official Action Dated Feb. 6, 2007 From the US Patent and Trademark Office Re. U.S. Appl. No. 10/525,838.
Restriction Official Action Dated Apr. 8, 2008 From the US Patent and Trademark Office Re. U.S. Appl. No. 11/497,225.
Restriction Official Action Dated Sep. 14, 2011 From the US Patent and Trademark Office Re. U.S. Appl. No. 12/583,746.
Restriction Official Action Dated Feb. 16, 2012 From the US Patent and Trademark Office Re. U.S. Appl. No. 13/178,737.
Restriction Official Action Dated Mar. 18, 2005 From the US Patent and Trademark Office Re. U.S. Appl. No. 10/363,209.
Restriction Official Action Dated Mar. 26, 2009 From the US Patent and Trademark Office Re. U.S. Appl. No. 12/172,007.
Second Amendment Dated Jul. 14, 2008 to Amendment of May 15, 2008 After Notice of Allowance of Apr. 14, 2008 From the US Patent and Trademark Office Re. U.S. Appl. No. 10/525,838.
Supplementary European Search Report Dated Nov. 19, 2004 From the European Patent Office Re. Application No. 01963414.6.
Supplementary Partial European Search Report Dated Nov. 28, 2007 From the European Patent Office Re. Application No. 03791288.8.
Translation of Office Action Dated Aug. 11, 2009 From the Japanese Patent Office Re. Application No. 2003-301176.
Translation of Office Action Dated Oct. 19, 2010 From the Japanese Patent Office Re. Application No. 2003-301176.
Arakaki et al. "T134, A Small-Molecule CXCR4 Inhibitor, Has No Cross-Drug Resistance With AMD3100, a CXCR4 Antagonist With a Different Structure", Journal of Virology, XP002199036, 73(2): 1719-1723, Feb. 1999.
Auerbach et al. "Angiogenesis Assays: Problems, Pitfalls and Potential", Cancer and Metastasis Reviews, 19: 167-172, 2000.
Di Cesare et al. "In Vitro Characterization and Inhibition of the CXCR4/CXCL12 Chemokine Axis in Human Uveal Melanoma Cell Lines", Cancer Cell International, XP021036445, 7(17): 1-8, Nov. 14, 2007. Abstract, Last Para, Title, p. 5, Right Col., Last Para.
Fransen et al. "Suppression of Dualtropic Human Immunodeficiency Virus Type 1 by the CXCR4 Antagonist AMD3100 Is Associated With Efficiency of CXCR4 Use and Baseline Virus Composition", Antimicrobial Agents and Chemotherapy, 52(7): 2608-2615, Apr. 28, 2008.

(56) References Cited

OTHER PUBLICATIONS

Fujii et al. "Peptide-Lead CXCR4 Antagonists With High Anti-HIV Activity", Current Opinion in Investigational Drugs, 2(9): 1198-1202, 2001.

Gotoh et al. "Increase of R5 HIV-1 Infection and CCR5 Expression in T Cells Treated With High Concentrations of CXCR4 Antagonists and SDF-1", Journal of Infection and Chemotherapy, 7(1): 28-36, 2001.

Gura "Cancer Models: Systems for Identifying New Drugs Are Often Faulty", Science, 278(5340): 1041-1042, Nov. 7, 1997.

Hatse et al. "CXC-ChemokineReceptor 4 as a Potential New Therapeutic Target for Neuroblastoma and Breast Cancer", International Journal of Cancer, XP001156644, Supplement, 13: 349, Abstract # p. 669, Jul. 2002.

Hendrix et al. "Safety, Pharmacokinetics, and Antiviral Activity of AMD3100, A Selective CXCR4 Receptor Inhibitor, in HIV-1 Infection", Journal of Aquired Immune Deficiency Syndromes, JAIDS, 37(2): 1253-1261, Oct. 1, 2004.

Hesselgesser et al. "Neuronal Apoptosis Induced by HIV-1 Gp120 and the Chemokine SDF-1Alpha Is Mediated by the Chemokine Receptor CXCR4", Current Biology, 8: 595-598, Apr. 27, 1998.

Hiramatsu et al. "Synthesis of CXCR4 Antagonists, T140 Derivatives With Improved Biostability, and Their SAR Study", Peptide Science, XP009092185, 203: 213-216, 2002. Abstract, Fig. 1.

Jain "Barriers to Drug Delivery in Solid Tumors. Many Tumors Resist Full Penetration by Anticancer Agents. Such Resistance May Help Explain Why Drugs That Eradicate Tumor Cells in Laboratory Dishes Often Fail to Eliminate Malignancies in the Body", Scientific American, p. 58-65, Jul. 1994.

Koshiba et al. "Expression of Stromal Cell-Derived Factor 1 and CXCR4 Ligand Receptor System in Pancreatic Cancer: a Possible Role for Tumor Progression", Clinical Cancer Research, 6(9): 3530-3535, Sep. 2000.

Matthys et al. "AMD3100, a Potent and Specific Antagonist of the Stromal Cell-Derived Factor-1 Chemokine Receptor CXCR4, Inhibits Autoimmune Joint Inflammation in IFN-Gamma Receptor-Deficient Mice", The Journal of Immunology, 167(8): 4686-4692, 2001.

Merck "Clinical Aspects of Cancer", The Merck Manual, Jun. 26, 2007.

Merck "Introduction: Overview of Cancer", The Merck Manual, Jun. 26, 2007.

Merck "Rheumatoid Arthritis (RA)", The Merck Manual, 18th Ed., 2005.

Mori et al. "Involvement of Stromal Cell-Derived Factor 1 and CXCR4 Receptor System in Pancreatic Cancer", Gastroenterology, XP009021758, 122(4/Suppl.1): A490, Abstract # T1608, Apr. 2002.

Nakashima et al. "Anti-Human Immunodeficiency Virus Activity of a Novel Synthetic Peptide, T22 ([Tyr-5,12, Lys-7]Polyphemusin II): A Possible Inhibitor of Virus-Cell Fusion", Antimicrobial Agents and Chemotherapy, 36(6): 1249-1255, Jun. 1992.

Neidl "Failure Modes in the Discovery Process", Cancer Drug Design and Discovery, Chap.18.2.2: 427-431, 2008.

Omagari et al. "Development of Specific CXCR4 Inhibitors Based on an Anti-HIV Peptide, T140, and Their Structure-Activity Relationships Study", Peptide Science, 2000(37): 129-132, 2001.

Sporn et al. "Chemoprevention of Cancer", Carcinogenesis, 21(3): 525-530, 2000.

Tamamura "Development of Selective Antagonists Against an HIV Second Receptor", Yakugaku Zasshi, 121(11): 781-792, 2001. Abstract in English.

Tamamura et al. "A Future Perspective on the Development of Chemokine Receptor CXCR4 Antagonists", Database EMBASE [Online], XP002675634, Database Accession No. EMB-2008509452, Oct. 2008. & Expert Opinion on Drug Discovery, 3(10): 1155-1166, Oct. 2008.

Tamamura et al. "A Low-Molecular-Weight Inhibitor Against the Chemokine Receptor CXCR4: A Strong Anti-HIV Peptide T140", Biochemic and Biophysical Research Communications, XP002169961, 253(3): 877-882, Jan. 1, 1998. Abstract, Fig.1.

Tamamura et al. "A Low-Molecular-Weight Inhibitor Against the Chemokine Receptor CXCR4: A Strong Anti-HIV Peptide T140", Biochemical and Biophysical Research Communications, 253(3): 877-882, 1998.

Tamamura et al. "Certification of the Critical Importance of L-3-(2-Naphtyl)Alanine at Position 3 of a Specific CXCR4 Inhibitor, T140, Leads to an Exploratory Performance of Its Downsizing Study", Bioorganic & Medicinal Chemistry, 10: 1417-1426, 2002.

Tamamura et al. "Development of Specific CXCR4 Inhibitors Possessing High Selectivity Indexes as Well as Complete Stability in Serum Based on an Anti-HIV Peptide T140", Bioorganic & Medicinal Chemistry Letters, XP002265743, 11(14): 1897-1902, Jul. 23, 2001. Abstract, Fig.1, p. 1901, r-h Col., Last Sentence Before 'Acknowledgements'.

Tamamura et al. "Downsizing of an HIV-Cell Fusion Inhibitor, T22 ([Tyr5,12, Lys7]-Polyphemusin II), With the Maintenance of Anti-HIV Activity and Solution Structure", Bioorganic & Medicinal Chemistry, 6: 473-479, 1998.

Tamamura et al. "Downsizing of an HIV-Cell Fusion Inhibitor, T22 ([Tyr5,12, Lys7]-Polyphemusin II), With the Maintenance of Anti-HIV Activity and Solution Structure", Bioorganic & Medicinal Chemistry, XP002458598, 6(4): 473-479, Apr. 1998. Abstract, Fig.1.

Tamamura et al. "Effective Lowly Cytotoxic Analogs of an HIV-Cell Fusion Inhibitor, T22 ([Tyr5,12, Lys7]-Polyphemusin II)", Bioorganic & Medicinal Chemistry, 6(2): 231-238, 1998.

Tamamura et al. "Effective Lowly Cytotoxic Analogs of an HIV-Cell Fusion Inhibitor, T22 ([Tyr5,12, Lys7]-Polyphemusin II)", Bioorganic & Medicinal Chemistry, XP002906341, 6(2): 231-238, Jan. 1, 1998. Abstract, Fig.1.

Tamamura et al. "Efficient Analogs of an Anti-HIV Peptide, T22 ([Tyr5,12, Lys7]-Polyphemusin II), Having Low Cytotoxicity", Peptide Science—Present and Future, Proceedings of the 1st International Peptide Symposium, XP002973954, 1997: 427-429, Jan. 1, 1999. Abstract, Fig.2.

Tamamura et al. "HIV-Cell Fusion Inhibitors Targeted to the HIV Second Receptor: T22 and Its Downsized Analogs With High Activity", Peptide Science, 1998(35): 49-52, 1999.

Tamamura et al. "Pharmacophore Identification of a Specific CXCR4 Inhibitor, T140, Leads to Development of Effective Anti-HIV Agents With Very High Selectivity Indexes", Bioorganic & Medicinal Chemistry Letters, 10(23): 2633-2637, 2000.

Tamamura et al. "T140 Analogs as CXCR4 Antagonists Identified as Anti-Metastatic Agents in the Treatment of Breast Cancer", FEBS Letters, XP004448372, 550: 79-83, Aug. 28, 2003.

Office Action Dated May 4, 2010 From the Israel Patent Office Re. Application No. 199468.

Office Action Dated May 4, 2010 From the Israel Patent Office Re. Application No. 199469.

Office Action Dated Sep. 4, 2011 From the Israel Patent Office Re. Application No. 199468 and Its Translation Into English.

Office Action Dated Oct. 31, 2011 From the Israel Patent Office Re. Application No. 199469 and Its Translation Into English.

Response Dated Oct. 21, 2010 to Office Action of May 4, 2010 From the Israel Patent Office Re. Application No. 199468.

Response Dated Oct. 21, 2010 to Office Action of May 4, 2010 From the Israel Patent Office Re. Application No. 199469.

Burger et al. "Small Peptide Inhibitors of the CXCR4 Chemokine Receptor (CD184) Antagonize the Activation, Migration, and Antiapoptotic Responses of CXCL12 in Chronic Lymphocytic Leukemia B Cells", Blood, 106(5): 1824-1830, Sep. 1, 2005.

Ghobrial et al. "Molecular Mechanisms Involved in Homing and Migration of Plasma Cells in Response to CXCR4", Blood, XP002629051, 104(11): 1-33, Apr. 12, 2005.

Menu et al. "The Involvement of Stromal Derived Factor 1Alpha in Homing and Progression of Multiple Myeloma in the 5TMM Model", Haematologica/the Hematology Journal, 91(5): 605-612, 2006.

Phillips et al. "Epidermal Growth Factor and Hypoxia-Induced Expression of CXC Chemokine Receptor 4 on Non-Small Cell Lung Cancer Cells Is Regulated by the Phosphatidylinositol 3-Kinase/PTEN/AKT/Mammalian Target of Rapamycin Signaling Pathway and Activation of Hypoxia Inducible Factor-1Alpha", The Journal of Biological Chemistry, 280(23): 22473-22481, 2005.

(56) References Cited

OTHER PUBLICATIONS

Ratajczak et al. "T140 Enhances G-CSF-Induced Mobilization of Hematopoietic Stem Cells", Experimental Hematology, 31: 154, Abstract #280, 2003.

Tamamura et al. "T140 Analogs as CXCR4 Antagonists Identified as Anti-Metastatic Agents in the Treatment of Breast Cancer", FEBS Letters, 550: 79-83, 2003.

Tsutsumi et al. "Therapeutic Potential of the Chemokine Receptor CXCR4 Antagonists as Multifunctional Agents", Biopolymers (Peptide Science), XP002629052, 88(2): 279-289, 2006.

Weekes et al. "Stromal Derived Factor1Alpha Mediates Resistance to mTOR Inhibition by the Preservation of Hypoxia Inducible Factor-!Alpha (HIF-1Alpha) Expression", Proceedings of the Annual Meeting of the American Association for Cancer Research, AACR, 47: 553, Abstract #2341, 2006.

Communication Pursuant to Article 94(3) EPC Dated Sep. 11, 2013 From the European Patent Office Re. Application No. 10176632.7.

International Preliminary Report on Patentability Dated Jul. 18, 2013 From the International Bureau of WIPO Re. Application No. PCT/IL2012/050008.

International Search Report and the Written Opinion Dated Sep. 2, 2013 From the International Searching Authority Re. Application No. PCT/IL2013/050352.

Office Action Dated Jul. 28, 2013 From the Israel Patent Office Re. Application No. 199469 and Its Translation Into English.

Requisition by the Examiner Dated Jul. 4, 2013 From the Canadian Intellectual Property Office Re. Application No. 2,537,158.

Requisition by the Examiner Dated Jul. 8, 2013 From the Canadian Intellectual Property Office Re. Application No. 2,421,183.

Burger et al. "CXCR4 Chemokine Receptor Antagonists: Perspectives in SCLC", Expert Opinion on Investigational Drugs, XP002711650, 18(4): 481-490, Apr. 2009.

Burger et al. "Potential of CXCR4 Antagonists for the Treatment of Metastatic Lung Cancer", Expert Reviews of Anticancer Therapy, XP009152669, 1(4): 621-630, Apr. 1, 2011.

Su et al. "Differential Expression of CXCR4 Is Associated With the Metastatic Potential of Human Non-Small Cell Lung Cancer Cells", Clinical Cancer Research, XP055076137, 11(23): 8273-8280, Dec. 1, 2005.

Communication Pursuant to Article 94(3) EPC Dated Oct. 4, 2013 From the European Patent Office Re. Application No. 07849622.1.

Communication Pursuant to Article 94(3) EPC Dated Oct. 4, 2013 From the European Patent Office Re. Application No. 07849623.9.

Completion Requirement Letter Dated Oct. 24, 2013 From the Canadian Intellectual Property Office Re. Application No. 2,765,345.

Notification of Office Action and Search Report Dated Nov. 5, 2013 From the State Intellectual Property Office of the People's Republic of China Re. Application No. 201080035931.5 and Its Translation into English.

Restriction Official Action Dated Oct. 3, 2013 From the US Patent and Trademark Office Re. U.S. Appl. No. 13/378,061.

Abraham et al. "Enhanced Unique Pattern of Hematopoietic Cell Mobilization Induced by the CXCR4 Antagonist 4F-Benzoyl-TN14003", Stem Cells, XP002629045, 25(9): 2158-2166, May 24, 2007.

\* cited by examiner

US 8,663,651 B2

T-140 PEPTIDE ANALOGS HAVING CXCR4 SUPER-AGONIST ACTIVITY FOR IMMUNOMODULATION

RELATED APPLICATION DATA

This application is the U.S. national stage of PCT/IL2007/001598 filed on Dec. 23, 2007, which claims priority to and benefit of U.S. Provisional Patent Application No. 60/876,145 filed on Dec. 21, 2006, the content of each of which is expressly incorporated herein in its entirety by reference hereto.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 49,811 byte ASCII (text) file named "Seq_List" created on Jun. 22, 2009.

FIELD OF THE INVENTION

The present invention is directed to compositions comprising T-140 peptide analogs having CXCR4 super-agonist activity and to novel therapeutic uses thereof for immunotherapy and vaccination.

BACKGROUND OF THE INVENTION

Chemokines, a family of small pro-inflammatory cytokines, and their receptors, regulate a variety of immune responses to infection, inflammation and tissue repair. Chemokines are divided between two major families on the basis of relative position of cysteine residues in the mature protein (C—C and C—X—C). Primarily, they are responsible for the directional migration, or chemotaxis, of lymphocytes to specific lymphoid tissues, and the recruitment of leukocytes to the sites of infection or tissue damage. In addition to their chemotactic function, chemokines are implicated in other biological events including embryogenesis, lymphopoiesis, vascularization, and HIV pathogenesis. More recently, it has been established that cancer cells exploit signaling through chemokine receptors for several key steps involved in initiation and progression of primary and metastatic cancer. Different types of cancers express different CC and CXC chemokine receptors. There is one chemokine receptor, however, that appears to be expressed by the majority of cancer types, namely, CXCR4.

The CXCR4/CXCL12 Axis

The chemokine receptor CXCR4 is a G-protein coupled receptor that is expressed in a wide assortment of normal tissues, and plays a fundamental role in fetal development, mobilization of hematopoietic stem cells and trafficking of naive lymphocytes (Rossi and Zlotnik, 2000). Besides normal tissues, CXCR4 appears to be expressed by at least 23 different epithelial, mesenchymal and hematopoietic cancers, including prostate cancer, and acute and chronic myeloid leukemias (Balkwill, 2004). The chemokine CXCL12 (also known as stromal-derived factor-1, or SDF-1) is CXCR4's only natural ligand. CXCL12 is expressed constitutively in a variety of tissues, including lung, liver, bone marrow and lymph nodes. These organs with highest expression of CXCL12 correlate with common metastatic destinations in many cancers. The chemokine receptor, CXCR4, and its ligand, CXCL12, appear to be an important chemokine axis regulating tumor growth and metastasis (Nagasawa, et al., 1994; Muller et al., 2001; Phillips, et al., 2003).

Binding of CXCL12 to CXCR4 activates a variety of intracellular signal transduction pathways and effector molecules that regulate cell chemotaxis, adhesion, survival, and proliferation. There are a number of key molecules that mediate signaling through CXCR4, and some of them will be described below.

CXCL12 and CXCR4 stimulate the phosphatidyl-inositol-3-kinase pathway that subsequently activates the protein kinase, Akt. Activated Akt phosphorylates a variety of intracellular targets, functioning to inhibit apoptosis and prolonging survival in different types of cancer cells. Beyond cell survival, Akt has also been implicated in effects of CXCR4 on migration of cells toward CXCL12 and their proliferation.

The mitogen-activated protein (MAP) kinase pathway is another signal transduction pathway regulated by CXCR4. Following stimulation with CXCL12, CXCR4 activates the kinase MEK, which in turn activates ERK1/2 MAP kinases. Activated ERK1/2 kinases phosphorylate transcription factors such as Elk-1; this process increases expression of genes that promote survival and proliferation of cancer cells.

CXCR4 also appears to regulate angiogenesis, the process that is important for both normal physiology and growth of tumors. Mice lacking CXCR4 or CXCL12 have defective formation of blood vessels in the gastrointestinal tract. Pro-angiogenic effect of CXCR4 signaling may be mediated through up-regulation of vascular-endothelial growth factor (VEGF). Thus, another potential function of CXCR4 signaling in tumor development is promotion of blood vessel production.

The CXCR4/CXCL 12 Axis in Hematopoietic Stem Cell Mobilization

All mature blood cells are derived from hematopoietic stem cells (HSC) through intermediates that are termed hematopoietic progenitor cells (HPCs). Hematopoietic cells at various stages of differentiation are localized within the bone marrow (BM), their main site of production. Their mobilization between BM and blood is a physiological process, but under steady-state conditions HPCs and HSCs circulate in the blood at frequencies too low to allow for efficient collection of numbers sufficient to transplantation. Recently, the use of peripheral blood as source of HSCs for transplantations has replaced bone marrow as the preferred source of hematopoietic rescue. Stem cell frequencies in blood are considerably increased both in responses to various growth factors and during the recovery phase following myelosuppressive chemotherapy. Increased number of hematopoietic cells in the blood and amelioration of their mobilization ability will improve the efficiency of transplantation and will shorten the time of cytopenia and engraftment.

Granulocyte Colony-stimulating Factor (G-CSF)-mobilized peripheral-blood mononuclear cells are routinely used as a source of hematopoietic stem cells for transplantation. However, this mobilization results in broad inter-individual variations in circulating progenitor cell numbers. Thus, optimal methods to mobilize and collect peripheral-blood progenitor cells for hematopoietic rescue still need to be found.

Over recent years it has become apparent that the interaction between CXCL12 and its receptor, CXCR4, plays pivotal role in mobilization and engraftment of hematopoietic cells (Kollet et al., 2002; Lapidot et al., 2002; Levesque et al., 2003; Peled et al., 1999; Lapidot et al., 2005; Dar et al., 2005). The CXCR4 receptor is widely expressed on many cell types including HSCs and HPCs and the interaction with its ligand seems to be involved in their chemotaxis, homing and survival. The CXCL12/CXCR4 axis was found to be involved in the retention of hematopoietic cells within the bone marrow microenvironment (Kim et al., 1998) and consequently, it was suggested that antagonizing the interactions of marrow-produced CXCL12 with CXCR4 expressed on HSCs might be an effective HSC mobilizing strategy.

CXCR4 Modulators and T-140 Analogs

Various uses of chemokine receptor modulators, including CXCR4 agonists and antagonists, have been described in the art (Princen et al., 2005; Tamamura et al., 2005). For example, the bicyclam drug termed AMD3100, originally discovered as an anti-HIV compound, specifically interacts with CXCR4 in an antagonistic manner. Blocking CXCR4 receptor with AMD3100 results in the mobilization of hematopoietic progenitor cells; when combining AMD3100 with G-CSF, additive effects were detected (Flomenberg et al., 2005; Broxmeyer et al., 2005). AMD3100 is currently undergoing clinical trials to evaluate its ability to increase stem cells available for transplant (Lack et al., 2005). U.S. Pat. No. 6,365,583 discloses a method to treat a subject who would be benefited by elevation of white blood cell count which method comprises administering to said subject a cyclic polyamine such as AMD3100. Martin et al. (2003) show that the mobilization of neutrophils from the bone marrow by the CXCR2-chemokine, KC, was enhanced by AMD3100, examined 60 minutes after administration to normal BALB/c mice.

U.S. Patent Application Publication No. 2004/0209921 discloses heterocyclic compounds that bind to chemokine receptors, including CXCR4 and CCR5, which may possess protective effects against infection of target cells by a human immunodeficiency virus (HIV). Other potential uses for these compounds suggested by '921 are enhancing the population of progenitor and/or stem cells, stimulating the production of white blood cells, and/or effecting regeneration of cardiac tissue.

U.S. Pat. No. 6,946,445 discloses CXCR4 antagonists comprising the sequence KGVSLSYR. The antagonists disclosed by the '445 patent are suggested to be potentially useful for reducing interferon gamma production by T-cells, treatment of an autoimmune disease, treatment of multiple sclerosis, treatment of other neurological diseases, treatment of cancer, and regulation of angiogenesis. U.S. Pat. No. 6,875,738 discloses methods for treating a solid tumor in a mammal and for inhibiting angiogenesis in a mammal using these antagonists.

U.S. Patent Application Publication No. 2005/0002939 discloses a method of treating ovarian cancer in a mammal, the method comprising administering to the mammal a therapeutically effective dose of a CXCR4 inhibitor. The '939 publication suggests that an anti-CXCR4 antibody may impact the survival or growth of a CXCR4-expressing tumor derived from a bladder tumor cell line in a mouse model.

T-140 is a 14-residue synthetic peptide developed as a specific CXCR4 antagonist that suppresses HIV-1 (X4-HIV-1) entry to T cells through specific binding to CXCR4 (Tamamura et al., 1998). Subsequently, peptide analogs of T-140 were developed as specific CXCR4 antagonist peptides with inhibitory activity at nanomolar levels (see Tamamura et al., 2003, WO 2002/020561 and WO 2004/020462).

WO 2002/020561 discloses novel peptide analogs and derivatives of T-140. The '561 publication demonstrates that the claimed peptides are potent CXCR4 inhibitors, manifesting high anti-HIV virus activity and low cytotoxicity.

WO 2004/020462 discloses additional novel peptide analogs and derivatives of T-140, including 4F-benzoyl-TN14003 (SEQ ID NO:1). The '462 publication further discloses novel preventive and therapeutic compositions and methods of using same utilizing T-140 analogs for the treatment of cancer and chronic rheumatoid arthritis. The specification of '462 demonstrates the ability of these peptides to inhibit cancer cell migration, including breast cancer and leukemia cells, and to inhibit metastasis formation in vivo. Further demonstrated therein is inhibition of delayed-type hypersensitivity reaction in mice and collagen-induced arthritis, an animal model of rheumatoid arthritis.

WO 2004/087068 is directed to a method for treating or preventing a CXCR4 mediated pathology comprising administering a CXCR4 peptide antagonist to a host in an amount sufficient to inhibit CXCR4 signal transduction in a cell expressing a CXCR4 receptor or homologue thereof, wherein the CXCR4 peptide antagonist is not an antibody or fragment thereof. The '068 publication discloses that exemplary CXCR4 peptide antagonists include T140 and derivatives of T140, and that the pathology includes cancer such as breast, brain, pancreatic, ovarian, prostate, kidney, and non-small lunch cancer. Other publications directed to the use of CXCR4 antagonists in cancer therapy include, for example, WO 00/09152, US 2002/0156034, and WO 2004/024178.

A recent publication by some of the inventors of the present invention (Avniel et al., 2006) discloses that blocking the CXCR4/CXCL12 axis by a T-140 analog resulted in a significant reduction in eosinophil accumulation in the dermis and improved epithelialization, thus significantly improving skin recovery after burns.

None of the prior art discloses or suggests that CXCR4 inhibitor peptides belonging to the T-140 analog family may also affect CXCR4 activity in an agonist manner. There exists a long felt need for compositions and methods useful for modulating CXCR4-mediated processes involved in pathological conditions in vivo.

SUMMARY OF THE INVENTION

The present invention is directed to novel therapeutic applications of T-140 analog peptides. The present invention discloses, for the first time, that T-140 analogs, hitherto known as CXCR4 inhibitors, unexpectedly also possess CXCR4 superagonistic properties. The present invention thus provides compositions and methods utilizing T-140 analogs in applications in which activation of CXCR4 in an agonistic manner is beneficial, such as for use as adjuvants for vaccination.

The present invention is based, in part, on the surprising discovery that the known T-140 analog 4F-benzoyl-TN14003 (4F-benzoyl-Arg-Arg-Nal-Cys-Tyr-Cit-Lys-DLys-Pro-Tyr-Arg-Cit-Cys-Arg-NH$_2$, SEQ ID NO:1), but not the bicyclam CXCR4 inhibitor AMD3100, induces, in an agonist manner, secretion of macrophage inflammatory protein 3α (MIP3α), a cytokine known to promote recruitment of dendritic cells and of B an T cells expressing CCR6, the receptor for MIP3α.

According to certain aspects of the present invention, there are provided novel vaccine compositions and methods of using same, utilizing 4F-benzoyl-TN14003 or other peptides of the T-140 analog family as adjuvants for increasing the immunogenicity of antigens. Without wishing to be bound by any theory or mechanism of action, the adjuvant effect of these peptides may be associated with their ability to stimulate MIP3α secretion, thereby increasing immunity to the administered antigen, or, in other embodiments, to CXCR4-expressing tumors.

Thus, in a first aspect, there is provided a vaccine composition comprising: (i) at least one antigen; (ii) at least one pharmaceutically acceptable adjuvant comprising a compound having CXCR4 agonistic properties in an amount sufficient to increase the immunogenicity of the at least one antigen; and (iii) a pharmaceutically acceptable carrier, excipient or diluent. Preferably, the compound is 4F-benzoyl-TN14003 or an analog or derivative thereof. Thus, in another embodiment there is provided a vaccine composition comprising: (i) at least one antigen; (ii) at least one pharmaceutically acceptable adjuvant comprising a peptide having an amino acid sequence as set forth in SEQ ID NO:1 or an analog or derivative thereof in an amount sufficient to increase the immunogenicity of the at least one antigen; and (iii) a pharmaceutically acceptable carrier, excipient or diluent.

The 4F-benzoyl-TN14003 analogs and derivatives used in the novel compositions and methods of the invention are the structurally and functionally related peptides disclosed in patent applications WO 2002/020561 and WO 2004/020462, also known as "T-140 analogs", as detailed hereinbelow.

In various particular embodiments, the analog or derivative has an amino acid sequence as set forth in the following formula (I) or a salt thereof:

```
1  2  3   4   5   6  7  8  9  10  11  12  13  14
A₁-A₂-A₃-Cys-Tyr-A₄-A₅-A₆-A₇-A₈-A₉-A₁₀-Cys-A₁₁    (I)
``` wherein:
- $A_1$ is an arginine, lysine, ornithine, citrulline, alanine or glutamic acid residue or a N-α-substituted derivative of these amino acids, or $A_1$ is absent;
- $A_2$ represents an arginine or glutamic acid residue if $A_1$ is present, or $A_2$ represents an arginine or glutamic acid residue or a N-α-substituted derivative of these amino acids if $A_1$ is absent;
- $A_3$ represents an aromatic amino acid residue;
- $A_4$, $A_5$ and $A_9$ each independently represents an arginine, lysine, ornithine, citrulline, alanine or glutamic acid residue;
- $A_6$ represents a proline, glycine, ornithine, lysine, alanine, citrulline, arginine or glutamic acid residue;
- $A_7$ represents a proline, glycine, ornithine, lysine, alanine, citrulline or arginine residue;
- $A_8$ represents a tyrosine, phenylalanine, alanine, naphthylalanine, citrulline or glutamic acid residue;
- $A_{10}$ represents a citrulline, glutamic acid, arginine or lysine residue;
- $A_{11}$ represents an arginine, glutamic acid, lysine or citrulline residue wherein the C-terminal carboxyl may be derivatized;

and the cysteine residue of the 4-position or the 13-position can form a disulfide bond, and the amino acids can be of either L or D form.

Exemplary peptides according to formula (I) are peptides having an amino acid sequence as set forth in any one of SEQ ID NOS:1-72, as presented in Table 1 hereinbelow.

In another preferable embodiment, the analog or derivative has an amino acid sequence as set forth in SEQ ID NO:65 (H-Arg-Arg-Nal-Cys-Tyr-Cit-Lys-DLys-Pro-Tyr-Arg-Cit-Cys-Arg-OH; TC14003).

In certain other particular embodiments, said analog or derivative is selected from the group consisting of:

```
                                                            (SEQ ID NO: 1)
4F-benzoyl-Arg-Arg-Nal-Cys-Tyr-Cit-Lys-DLys-Pro-Tyr-Arg-Cit-Cys-Arg-NH₂, (SEQ ID NO: 2)
Ac-Arg-Arg-Nal-Cys-Tyr-Cit-Lys-DLys-Pro-Tyr-Arg-Cit-Cys-Arg-OH, (SEQ ID NO: 3)
Ac-Arg-Arg-Nal-Cys-Tyr-Arg-Lys-DCit-Pro-Tyr-Arg-Cit-Cys-Arg-OH, (SEQ ID NO: 4)
Ac-Arg-Arg-Nal-Cys-Tyr-Cit-Lys-DCit-Pro-Tyr-Arg-Cit-Cys-Arg-OH, (SEQ ID NO: 10)
Ac-Arg-Arg-Nal-Cys-Tyr-Cit-Lys-DCit-Pro-Tyr-Arg-Cit-Cys-Arg-NH₂, (SEQ ID NO: 46)
TMguanyl-Arg-Arg-Nal-Cys-Tyr-Cit-Lys-DCit-Pro-Tyr-Arg-Cit-Cys-Arg-NH₂;, (SEQ ID NO: 47)
ACA-Arg-Arg-Nal-Cys-Tyr-Cit-Lys-DCit-Pro-Tyr-Arg-Cit-Cys-Arg-NH₂, (SEQ ID NO: 51)
Ac-Arg-Arg-Nal-Cys-Tyr-Cit-Lys-DLys-Pro-Tyr-Arg-Cit-Cys-Arg-NH₂, (SEQ ID NO: 52)
Ac-Arg-Arg-Nal-Cys-Tyr-Arg-Lys-DCit-Pro-Tyr-Arg-Cit-Cys-Arg-NH₂, (SEQ ID NO: 53)
4F-benzoyl-Arg-Arg-Nal-Cys-Tyr-Cit-Lys-DGlu-Pro-Tyr-Arg-Cit-Cys-Arg-NHMe, (SEQ ID NO: 54)
4F-benzoyl-Arg-Arg-Nal-Cys-Tyr-Cit-Lys-DGlu-Pro-Tyr-Arg-Cit-Cys-Arg-NHEt, (SEQ ID NO: 55)
4F-benzoyl-Arg-Arg-Nal-Cys-Tyr-Cit-Lys-DGlu-Pro-Tyr-Arg-Cit-Cys-Arg-NHiPr, (SEQ ID NO: 56)
4F-benzoyl-Arg-Arg-Nal-Cys-Tyr-Cit-Lys-DGlu-Pro-Tyr-Arg-Cit-Cys-Arg-tyramine, (SEQ ID NO: 65)
H-Arg-Arg-Nal-Cys-Tyr-Cit-Lys-DLys-Pro-Tyr-Arg-Cit-Cys-Arg-OH, (SEQ ID NO: 66)
H-Arg-Arg-Nal-Cys-Tyr-Cit-Lys-DLys-Pro-Tyr-Arg-Cit-Cys-Arg-NH₂,
```

-continued

H-Arg-Arg-Nal-Cys-Tyr-Cit-Lys-DCit-Pro-Tyr-Arg-Cit-Cys-Arg-NH$_2$, (SEQ ID NO: 68)

H-Arg-Arg-Nal-Cys-Tyr-Cit-Lys-DCit-Pro-Tyr-Arg-Cit-Cys-Arg-OH, (SEQ ID NO: 70)
and H-Arg-Arg-Nal-Cys-Tyr-Arg-Lys-DCit-Pro-Tyr-Arg-Cit-Cys-Arg-OH. (SEQ ID NO: 71)

In other particular embodiments, said analog or derivative has an amino acid sequence as set forth in any one of SEQ ID NOS:4, 10, 45, 46, 68 and 70. In further particular embodiments, said analog or derivative has an amino acid sequence as set forth in any one of SEQ ID NOS:2, 51, 65 and 66. In other particular embodiments, said analog or derivative has an amino acid sequence as set forth in any one of SEQ ID NOS:53-56, presented in Table 1 hereinbelow.

The vaccines of the invention comprise at least one antigen capable of eliciting a desired immune response in the subject. In various embodiments, the antigen may include, for example, proteins, peptides, attenuated or killed microorganisms or cells (e.g. cancer cells), saccharides (e.g. bacterial polysaccharides), and antibodies or active fragments thereof. In a particular embodiment, the antigen is a tumor-associated antigen.

In another embodiment, the antigen is encoded by a nucleic acid sequence administered to the subject in combination with an adjuvant comprising a T-140 analog or a nucleic acid sequence encoding same. Thus, another embodiment of the invention provides a DNA vaccine composition comprising: (i) a recombinant construct comprising a nucleic acid sequence encoding at least one antigen, the nucleic acid sequence being operably linked to at least one transcription control sequence; (ii) at least one pharmaceutically acceptable adjuvant comprising a compound having CXCR4 agonistic properties, preferably a peptide having an amino acid sequence as set forth in SEQ ID NO:1 or an analog or derivative thereof in an amount sufficient to increase the immunogenicity of the at least one antigen; and (iii) a pharmaceutically acceptable carrier, excipient or diluent.

In another aspect, the invention provides a method for enhancing the immunogenicity of an antigen, comprising combining the antigen with a compound having CXCR4 agonistic properties, preferably a peptide having an amino acid sequence as set forth in SEQ ID NO:1 or an analog or derivative thereof in an amount sufficient to increase the immunogenicity of said antigen.

In another aspect, there is provided a method for stimulating or enhancing in a subject in need thereof an immune response to an antigen, comprising administering to the subject an immunogenic amount of the antigen or a nucleic acid sequence encoding said antigen and an immunogenicity-augmenting amount of a compound having CXCR4 agonistic properties, preferably a peptide having an amino acid sequence as set forth in SEQ ID NO:1 or an analog or derivative thereof in concurrent or sequential combination with said antigen.

In another aspect, the invention provides a method for enhancing the immunogenicity of a tumor characterized by CXCR4 membrane expression in a subject in need thereof, comprising administering to the subject a compound having CXCR4 agonistic properties, preferably a peptide having an amino acid sequence as set forth in SEQ ID NO:1 or an analog or derivative thereof in an amount sufficient to increase the immunogenicity of said tumor.

In another aspect, the invention provides a method for inducing or enhancing secretion of MIP3α from cells characterized by CXCR4 membrane expression, comprising contacting the cells with a compound having CXCR4 agonistic properties, preferably a peptide having an amino acid sequence as set forth in SEQ ID NO:1 or an analog or derivative thereof. In one embodiment, the cells are malignant cells (e.g. prostate cancer or lymphoma cells).

Other objects, features and advantages of the present invention will become clear from the following description and drawings.

BRIEF DESCRIPTION OF THE DRAWINGS

FIG. 1 demonstrates that 4F-benzoyl-TN14003 enhances MIP3α secretion by the prostate cancer cell line PC3 in a CXCR4-dependent manner.

FIG. 2 demonstrates that CXCR4 silencing with siRNA inhibits the secretion of MIP3α by PC3-CXCR4.5 cells.

DETAILED DESCRIPTION OF THE INVENTION

Figure 1A:
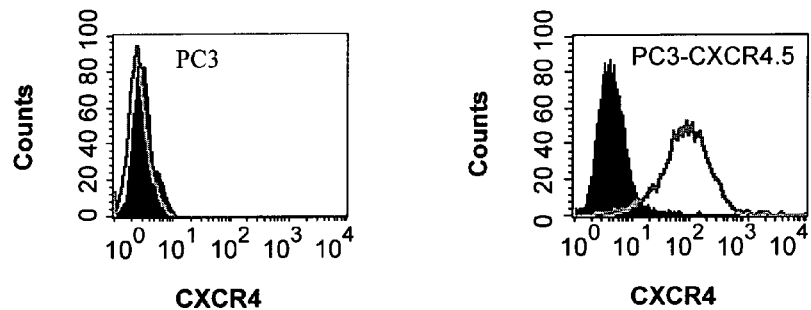
FIG. 1A illustrates FACS analysis of PC3 cells (left panel) and PC3-CXCR4.5 cells (right panel) stained for the control and CXCR4 antibodies.

The present invention is directed to novel compositions and methods wherein T-140 analog peptides, hitherto known as CXCR4 antagonists, are used to stimulate CXCR4-mediated processes in an agonistic manner.

The present invention discloses surprisingly that 4F-benzoyl-TN14003 (SEQ ID NO:1), a known CXCR4 inhibitor belonging to the T-140 peptide family, mediates unique beneficial effects, which are not mediated by other CXCR4 inhibitors such as AMD3100. 4F-benzoyl-TN14003 was surprisingly found to induce MIP3α secretion from CXCR4-expressing cell lines and tumors, and is thus useful for inducing anti-tumor immunity and to induce an enhanced immune response when used as an adjuvant. The invention further discloses for the first time that the natural ligand of CXCR4, namely CXCL12, was also able to induce MIP3α secretion, to a lesser extent than 4F-benzoyl-TN14003.

T-140 Analogs

The peptides described in this specification have an N-terminus (amino-terminal) at the left extremity and a C-terminus (carboxyl-terminal) at the right extremity in accordance with the customary practice of peptide notations.

In this specification and drawings, the representations of amino acids, etc. by brevity codes are made by the use of the codes prescribed by IUPAC-IUB Commission on Biochemical Nomenclature or by the codes customarily used in the relevant art. Examples of such codes are shown below. If an optical isomer exists with respect to an amino acid, it preferably represents the L form unless otherwise expressly specified.

Gly or G: glycine; Ala or A: alanine; Val or V: valine; Leu or L: leucine; Ile or I: isoleucine; Ser or S: serine; Thr or T: threonine; Cys or C: cysteine; Met or M: methionine; Glu or E: glutamic acid; Asp or D: aspartic acid; Lys or K: lysine; Arg or R: arginine; His or H: histidine; Phe or F: phenylalanine; Tyr or Y: tyrosine; Trp or W: tryptophan; Pro or P: proline; Asn or N: asparagine; Gln or Q: glutamine; pGlu: pyroglutamic acid; Nal: 3-(2-naphthyl) alanine; Cit: citrulline; DLys: D-lysine; DCit: D-citrulline; DGlu: D-glutamic acid; Me: methyl group; Et: ethyl group; Bu: butyl group; Ph: phenyl group.

The substituents, protective group and reagents often used in this specification are indicated by the following codes.
BHA: benzhydrylamine
pMBHA: p-methylbenzhydrylamine
Tos: p-toluenesulphonyl
CHO: formyl
HONB: N-hydroxy-5-norbornene-2,3-dicarboximide
OcHex: cyclohexyl ester
Bzl: benzyl
Cl$_2$-Bzl: dichloro-benzyl
Bom: benzyloxymethyl
Z: benzyloxycarbonyl
Br-Z: 2-bromobenzyloxycarbonyl
Boc: t-butyloxycarbonyl
DCM: dichloromethane
HOBt: 1-hydroxybenzotriazole
DCC: N,N'-dicyclohexylcarbodiimide
TFA: trifluoroacetic acid
DIEA: diisopropylethylamine
Fmoc: N-9-fluorenylmethoxycarbony
DNP: dinitrophenyl
Bum: tertiarybutoxymethyl
Trt: trityl
Ac: acetyl
Guanyl: guanyl
Succinyl: succinyl
glutaryl: glutaryl
TMguanyl: tetramethylguanyl
2F-benzoyl: 2-fluorobenzoyl
4F-benzoyl: 4-fluorobenzoyl
APA: 5-aminopentanoyl
ACA: 6-aminohexanoyl
desamino-Arg: 2-desamino-arginyl
Deamino TMG-APA: the Following Formula (IV):

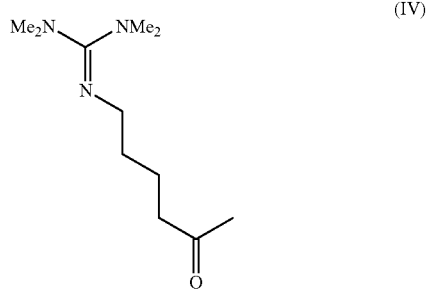

R—CH2: the following formula (V):

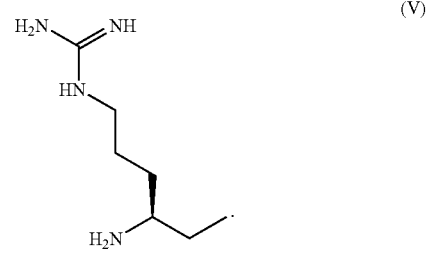

In N-terminal amino acids, [H—] indicates that the terminal amino group is not derivatized, and in C-terminal amino acids, [—OH] indicates that the terminal carboxyl group is not derivatized.

The 4F-benzoyl-TN14003 analogs and derivatives of the invention belong to a family of structurally closely related peptides, also known as T-140 analogs.

T-140 is a known peptide having the amino acid sequence H-Arg-Arg-Nal-Cys-Tyr-Arg-Lys-DLys-Pro-Tyr-Arg-Cit-Cys-Arg-OH (SEQ ID NO:69, Tamamura et al., 2003). The preferable peptides of the invention include analogs and derivatives disclosed in patent applications WO 2002/020561 and WO 2004/020462.

In one aspect, the present invention relates to the use of pharmaceutical compositions comprising as an active ingredient a peptide indicated by the following formula (I) or a salt thereof:

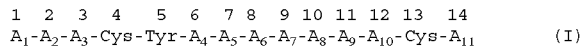

A₁-A₂-A₃-Cys-Tyr-A₄-A₅-A₆-A₇-A₈-A₉-A₁₀-Cys-A₁₁    (I)

wherein:

$A_1$ in the above-mentioned formula (I) represents an arginine, lysine, ornithine, citrulline, alanine or glutamic acid residue (either L or D form) which may be derivatized at the N-terminus, or $A_1$ is a hydrogen atom, or it is preferable that $A_1$ is an arginine, citrulline, alanine or D-glutamic acid residue, or $A_1$ is a hydrogen atom.

Examples of "N-terminal derivatized peptides" or "N-α-substituted derivatives" include, but are not limited to, those protected by formyl group; acyl group, e.g., acetyl group, propionyl group, butyryl group, pentanoyl group, $C_{2-6}$alkanoyl group e.g. hexanoyl group, benzoyl group, arylcarbonyl group e.g. substituted benzoyl group (e.g.: 2-fluorobenzoyl, 3-fluorobenzoyl group, 4-fluorobenzoyl group, 2-bromobenzoyl group, 3-bromobenzoyl group, 4-bromobenzoyl group, 2-nitrobenzoyl group, 3-nitrobezoyl group, 4-nirtobenzoyl group), succinyl group, glutaryl group; nicotinyl group; isonicotinyl group; alkylsulfonyl group (e.g.: methanesulfonyl group, ethanesulfonyl group, propanesulfonyl group, camphorsulfonyl group); arylsulfonyl group (e.g.: p-toluenesulfonyl group, 4-fluorobenzenesulfonyl group, mesitylenesulfonyl group, 4-aminobenzenesulfonyl group, dansyl group, 4-bromobenzenesulfonyl group) etc. Or, the N-terminal amino acid group may be absent.

Optionally and preferably, the peptide is derivatized at the N terminus with a substituted benzoyl group. In a particular embodiment, the substituted benzoyl group is a 4-fluorobenzoyl group. In another particular embodiment, the substituted benzoyl group is a 2-fluorobenzoyl group.

$A_2$ in the above-mentioned formula (I) represents an arginine or glutamic acid residue (either L or D form) if $A_1$ is an arginine, lysine, ornithine, citrulline, alanine or glutamic acid residue (either L or D form) which may be derivatized at the N-terminus, or $A_2$ represents an arginine or glutamic acid residue (either L or D form) which may be derivatized at the N-terminus if $A_1$ is absent, or it is preferable that $A_2$ is an arginine or glutamic acid residue if $A_1$ is an arginine, citrulline, alanine or glutamic acid residue which may be derivatized at the N-terminus, or $A_2$ is an arginine or glutamic acid residue which may be derivatized at N-terminus if $A_1$ is absent. Examples of "peptides derivatized at the N-terminus" include, but are not limited to, the same ones as those mentioned in A1.

$A_3$ in the above-mentioned formula (I) represents an aromatic amino acid residue (e.g., phenylalanine, tryptophan, 3-(2-naphthyl)alanine, tyrosine, 4-fluorophenylalanine, 3-(1-naphthyl)alanine (either L or D form), or preferably, $A_3$ represents phenylalanine, tryptophan or 3-(2-naphthyl)alanine.

$A_4$ in the above-mentioned formula (I) represents an arginine, lysine, ornithine, citrulline, alanine or glutamic acid residue (either L or D form), or it is preferable that $A_4$ is an arginine, citrulline, alanine or L- or D-glutamic acid residue.

$A_5$ in the above-mentioned formula (I) represents an arginine, lysine, ornithine, citrulline, alanine or glutamic acid residue (either L or D form), or it is preferable that $A_5$ is an arginine, citrulline, alanine, lysine or glutamic acid residue.

$A_6$ in the above-mentioned formula (I) represents a proline, glycine, ornithine, lysine, alanine, citrulline, arginine or glutamic acid residue (either L or D form), or it is preferable that $A_6$ is a D-lysine, D-alanine, D-citrulline or D-glutamic acid residue.

$A_7$ in the above-mentioned formula (I) represents a proline, glycine, ornithine, lysine, alanine, citrulline or arginine residue (either L or D form), or it is preferable that $A_7$ is a proline or alanine residue.

$A_8$ in the above-mentioned formula (I) represents a tyrosine, phenylalanine, alanine, naphthylalanine, citrulline or glutamic acid residue (either L or D form), or it is preferable that $A_8$ is a tyrosine, alanine or D-glutamic acid residue.

$A_9$ in the above-mentioned formula (I) represents an arginine, lysine, ornithine, citrulline, alanine or glutamic acid residue (either L or D form), or it is preferable that $A_9$ is an arginine, citrulline or glutamic acid residue.

$A_{10}$ in the above-mentioned formula (I) represents a citrulline, glutamic acid, arginine or lysine residue (either L or D form), or it is preferable that $A_{10}$ is a citrulline or D-glutamic acid residue.

$A_{11}$ in the above-mentioned formula (I) represents an arginine, glutamic acid, lysine or citrulline residue (either L or D form) which may be derivatized at C-terminus, or it is preferable that $A_{11}$ is an arginine or glutamic acid residue which may be derivatized at the C-terminus.

"C-terminal derivatization" or "C-terminal carboxyl derivatization" includes, without limitation, amidation (—CONH₂, —CONHR, —CONRR') and esterification (—COOR). Herein, R and R' in amides and esters include, for example, $C_{1-6}$ alkyl group e.g. methyl, ethyl, n-propyl, iso-propyl, or n-butyl, $C_{3-8}$ cycloalkyl group e.g. cyclopentyl, cyclohexyl, $C_{6-12}$ aryl group e.g. phenyl and α-naphthyl, phenyl-$C_{1-2}$ alkyl group e.g. benzyl, phenethyl or $C_{7-14}$ aralkyl group e.g. $C_{1-2}$ alkyl group e.g. α-naphthyl methyl group, and additionally, pivaloyloxymethyl group which is generally used as an oral bioavailable ester.

If a peptide of the present invention has carboxy groups (or carboxylates) at side-chain terminals other than C-terminus, the peptide having amidated or esterificated carboxy groups at side-chain terminals is included in the peptides of the present invention. As the amides and esters in this case, for example, the amides and esters exemplified in $A_{11}$ are similarly used. Also, the peptides of the present invention include peptides in which substituents (e.g.—OH, —SH, amino group, imidazole group, indole group, guanidino group, etc.) on the intramolecular amino acid side chains are protected by suitable protective group (e.g. $C_{1-6}$ acyl group, $C_{2-6}$ alkanoyl such as formyl group, acetyl group, etc.), or complex peptides such as glycopeptides combined with sugar chain in the above-mentioned peptides.

Salts of the peptides of the present invention include physiologically acceptable salts of acids or bases and particularly, physiologically acceptable acid addition salts are preferable. Such salts are exemplified by salts of inorganic acids (e.g. hydrochloric acid, phosphoric acid, hydrobromic acid, sulfuric acid), or salts of organic acids (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid).

In one embodiment, the composition comprises a peptide as set forth in formula (I) as defined hereinabove, wherein $A_1$ is a glutamic acid residue or is absent.

In another embodiment, the composition comprises a peptide as set forth in formula (I) as defined hereinabove, wherein $A_4$ is a glutamic acid residue.

In another embodiment, the composition comprises a peptide as set forth in formula (I) as defined hereinabove, wherein $A_6$ is a glutamic acid residue.

In another embodiment, the composition comprises a peptide as set forth in formula (I) as defined hereinabove, wherein $A_8$ is a glutamic acid residue.

In another embodiment, the composition comprises a peptide as set forth in formula (I) as defined hereinabove, wherein $A_9$ is a glutamic acid residue.

In another embodiment, the composition comprises a peptide as set forth in formula (I) as defined hereinabove, wherein $A_5$ is an arginine or glutamic acid residue.

In another embodiment, the composition comprises a peptide as set forth in formula (I) as defined hereinabove, wherein $A_{10}$ is a glutamic acid, arginine or lysine residue.

In another embodiment, the composition comprises a peptide as set forth in formula (I) as defined hereinabove, wherein $A_{11}$ is a glutamic acid, lysine or citrulline residue.

In another embodiment, the peptide has an amino acid sequence as set forth in any one of SEQ ID NOS:1-72 presented in Table 1 herein:

TABLE 1

T-140 and currently preferred T-140 analogs

| Analog | SEQ ID NO: | Amino acid sequence |
|---|---|---|
| 4F-benzoyl-TN14003 | 1 | 4F-benzoyl-Arg-Arg-Nal-Cys-Tyr-Cit-Lys-DLys-Pro-Tyr-Arg-Cit-Cys-Arg-NH$_2$ |
| AcTC14003 | 2 | Ac-Arg-Arg-Nal-Cys-Tyr-Cit-Lys-DLys-Pro-Tyr-Arg-Cit-Cys-Arg-OH |
| AcTC14005 | 3 | Ac-Arg-Arg-Nal-Cys-Tyr-Arg-Lys-DCit-Pro-Tyr-Arg-Cit-Cys-Arg-OH |
| AcTC14011 | 4 | Ac-Arg-Arg-Nal-Cys-Tyr-Cit-Lys-DCit-Pro-Tyr-Arg-Cit-Cys-Arg-OH |
| AcTC14013 | 5 | Ac-Arg-Arg-Nal-Cys-Tyr-Cit-Lys-DLys-Pro-Tyr-Cit-Cit-Cys-Arg-OH |
| AcTC14015 | 6 | Ac-Cit-Arg-Nal-Cys-Tyr-Cit-Lys-DLys-Pro-Tyr-Arg-Cit-Cys-Arg-OH |
| AcTC14017 | 7 | Ac-Cit-Arg-Nal-Cys-Tyr-Arg-Lys-DCit-Pro-Tyr-Arg-Cit-Cys-Arg-OH |
| AcTC14019 | 8 | Ac-Arg-Arg-Nal-Cys-Tyr-Arg-Lys-DCit-Pro-Tyr-Cit-Cit-Cys-Arg-OH |
| AcTC14021 | 9 | Ac-Cit-Arg-Nal-Cys-Tyr-Arg-Lys-DLys-Pro-Tyr-Cit-Cit-Cys-Arg-OH |
| AcTC14012 | 10 | Ac-Arg-Arg-Nal-Cys-Tyr-Cit-Lys-DCit-Pro-Tyr-Arg-Cit-Cys-Arg-NH$_2$ |
| AcTC14014 | 11 | Ac-Arg-Arg-Nal-Cys-Tyr-Cit-Lys-DLys-Pro-Tyr-Cit-Cit-Cys-Arg-NH$_2$ |
| AcTC14016 | 12 | Ac-Cit-Arg-Nal-Cys-Tyr-Cit-Lys-DLys-Pro-Tyr-Arg-Cit-Cys-Arg-NH$_2$ |
| AcTC14018 | 13 | Ac-Cit-Arg-Nal-Cys-Tyr-Arg-Lys-DCit-Pro-Tyr-Arg-Cit-Cys-Arg-NH$_2$ |
| AcTC14020 | 14 | Ac-Arg-Arg-Nal-Cys-Tyr-Arg-Lys-DCit-Pro-Tyr-Cit-Cit-Cys-Arg-NH$_2$ |
| AcTC14022 | 15 | Ac-Cit-Arg-Nal-Cys-Tyr-Arg-Lys-DLys-Pro-Tyr-Cit-Cit-Cys-Arg-NH$_2$ |
| TE14001 | 16 | H-DGlu-Arg-Nal-Cys-Tyr-Arg-Lys-DLys-Pro-Tyr-Arg-Cit-Cys-Arg-OH |
| TE14002 | 17 | H-Arg-Glu-Nal-Cys-Tyr-Arg-Lys-DLys-Pro-Tyr-Arg-Cit-Cys-Arg-OH |
| TE14003 | 18 | H-Arg-Arg-Nal-Cys-Tyr-Glu-Lys-DLys-Pro-Tyr-Arg-Cit-Cys-Arg-OH |
| TE14004 | 19 | H-Arg-Arg-Nal-Cys-Tyr-Arg-Glu-DLys-Pro-Tyr-Arg-Cit-Cys-Arg-OH |
| TE14005 | 20 | H-Arg-Arg-Nal-Cys-Tyr-Arg-Lys-DGlu-Pro-Tyr-Arg-Cit-Cys-Arg-OH |
| TE14006 | 21 | H-Arg-Arg-Nal-Cys-Tyr-Arg-Lys-DLys-Pro-Tyr-Glu-Cit-Cys-Arg-OH |
| TE14007 | 22 | H-Arg-Arg-Nal-Cys-Tyr-Arg-Lys-DLys-Pro-Tyr-Arg-Cit-Cys-Glu-OH |
| TE14011 | 23 | H-Arg-Arg-Nal-Cys-Tyr-Cit-Lys-DGlu-Pro-Tyr-Arg-Cit-Cys-Arg-NH$_2$ |
| TE14012 | 24 | H-Arg-Arg-Nal-Cys-Tyr-DGlu-Lys-DCit-Pro-Tyr-Arg-Cit-Cys-Arg-NH$_2$ |
| TE14013 | 25 | H-Arg-Arg-Nal-Cys-Tyr-DGlu-Lys-DGlu-Pro-Tyr-Arg-Cit-Cys-Arg-NH$_2$ |
| TE14014 | 26 | H-DGlu-Arg-Nal-Cys-Tyr-Cit-Lys-DGlu-Pro-Tyr-Arg-Cit-Cys-Arg-NH$_2$ |
| TE14015 | 27 | H-Arg-Arg-Nal-Cys-Tyr-Cit-Lys-DGlu-Pro-DGlu-Arg-Cit-Cys-Arg-NH$_2$ |
| TE14016 | 28 | H-Arg-Arg-Nal-Cys-Tyr-Cit-Lys-DGlu-Pro-Tyr-Arg-DGlu-Cys-Arg-NH2 |
| AcTE14014 | 29 | Ac-DGlu-Arg-Nal-Cys-Tyr-Cit-Lys-DGlu-Pro-Tyr-Arg-Cit-Cys-Arg-NH$_2$ |
| AcTE14015 | 30 | Ac-Arg-Arg-Nal-Cys-Tyr-Cit-Lys-DGlu-Pro-DGlu-Arg-Cit-Cys-Arg-NH$_2$ |
| AcTE14016 | 31 | Ac-Arg-Arg-Nal-Cys-Tyr-Cit-Lys-DGlu-Pro-Tyr-Arg-DGlu-Cys-Arg- |

TABLE 1-continued

T-140 and currently preferred T-140 analogs

| Analog | SEQ ID NO: | Amino acid sequence |
|---|---|---|
| | | NH₂ |
| TF1: AcTE14011 | 32 | Ac-Arg-Arg-Nal-Cys-Tyr-Cit-Lys-DGlu-Pro-Tyr-Arg-Cit-Cys-Arg-NH₂ |
| TF2: guanyl-TE14011 | 33 | guanyl-Arg-Arg-Nal-Cys-Tyr-Cit-Lys-DGlu-Pro-Tyr-Arg-Cit-Cys-Arg-NH₂ |
| TF3: TMguanyl-TE14011 | 34 | TMguanyl-Arg-Arg-Nal-Cys-Tyr-Cit-Lys-DGlu-Pro-Tyr-Arg-Cit-Cys-Arg-NH₂ |
| TF4: TMguanyl-TE14011 (2-14) | 35 | TMguanyl-Arg-Nal-Cys-Tyr-Cit-Lys-DGlu-Pro-Tyr-Arg-Cit-Cys-Arg-NH₂ |
| TF5: 4F-benzoyl-TE14011 | 36 | 4F-benzoyl-Arg-Arg-Nal-Cys-Tyr-Cit-Lys-DGlu-Pro-Tyr-Arg-Cit-Cys-Arg-NH₂ |
| TF6: 2F-benzoyl-TE14011 | 37 | 2F-benzoyl-Arg-Arg-Nal-Cys-Tyr-Cit-Lys-DGlu-Pro-Tyr-Arg-Cit-Cys-Arg-NH₂ |
| TF7: APA-TE14011 (2-14) | 38 | APA-Arg-Nal-Cys-Tyr-Cit-Lys-DGlu-Pro-Tyr-Arg-Cit-Cys-Arg-NH₂ |
| TF8: desamino-R-TE14011 (2-14) | 39 | desamino-R-Arg-Nal-Cys-Tyr-Cit-Lys-DGlu-Pro-Tyr-Arg-Cit-Cys-Arg-NH₂ |
| TF9: guanyl-TE14011 (2-14) | 40 | Guanyl-Arg-Nal-Cys-Tyr-Cit-Lys-DGlu-Pro-Tyr-Arg-Cit-Cys-Arg-NH₂ |
| TF10: succinyl-TE14011 (2-14) | 41 | succinyl-Arg-Nal-Cys-Tyr-Cit-Lys-DGlu-Pro-Tyr-Arg-Cit-Cys-Arg-NH₂ |
| TF11: glutaryl-TE14011 (2-14) | 42 | glutaryl-Arg-Nal-Cys-Tyr-Cit-Lys-DGlu-Pro-Tyr-Arg-Cit-Cys-Arg-NH₂ |
| TF12: deaminoTMG-APA-TE14011 (2-14) | 43 | deaminoTMG-APA-Arg-Nal-Cys-Tyr-Cit-Lys-DGlu-Pro-Tyr-Arg-Cit-Cys-Arg-NH₂ |
| TF15: H-Arg-CH₂NH-RTE14011 (2-14) | 44 | R-CH₂-Arg-Nal-Cys-Tyr-Cit-Lys-DGlu-Pro-Tyr-Arg-Cit-Cys-Arg-NH₂ |
| TF17: TE14011 (2-14) | 45 | H-Arg-Nal-Cys-Tyr-Cit-Lys-DGlu-Pro-Tyr-Arg-Cit-Cys-Arg-NH₂ |
| TF18: TMguanyl-TC14012 | 46 | TMguanyl-Arg-Arg-Nal-Cys-Tyr-Cit-Lys-DCit-Pro-Tyr-Arg-Cit-Cys-Arg-NH₂ |
| TF19: ACA-TC14012 | 47 | ACA-Arg-Arg-Nal-Cys-Tyr-Cit-Lys-DCit-Pro-Tyr-Arg-Cit-Cys-Arg-NH₂ |
| TF20: ACA-T140 | 48 | ACA-Arg-Arg-Nal-Cys-Tyr-Arg-Lys-DLys-Pro-Tyr-Arg-Cit-Cys-Arg-OH |
| TZ14011 | 49 | H-Arg-Arg-Nal-Cys-Tyr-Cit-Arg-DLys-Pro-Tyr-Arg-Cit-Cys-Arg-NH₂ |

TABLE 1-continued

T-140 and currently preferred T-140 analogs

| Analog | SEQ ID NO: | Amino acid sequence |
|---|---|---|
| AcTZ14011 | 50 | Ac-Arg-Arg-Nal-Cys-Tyr-Cit-Arg-DLys-Pro-Tyr-Arg-Cit-Cys-Arg-NH$_2$ |
| AcTN14003 | 51 | Ac-Arg-Arg-Nal-Cys-Tyr-Cit-Lys-DLys-Pro-Tyr-Arg-Cit-Cys-Arg-NH$_2$ |
| AcTN14005 | 52 | Ac-Arg-Arg-Nal-Cys-Tyr-Arg-Lys-DCit-Pro-Tyr-Arg-Cit-Cys-Arg-NH$_2$ |
| 4F-benzoyl-TN14011-Me | 53 | 4F-benzoyl-Arg-Arg-Nal-Cys-Tyr-Cit-Lys-DGlu-Pro-Tyr-Arg-Cit-Cys-Arg-NHMe |
| 4F-benzoyl-TN14011-Et | 54 | 4F-benzoyl-Arg-Arg-Nal-Cys-Tyr-Cit-Lys-DGlu-Pro-Tyr-Arg-Cit-Cys-Arg-NHEt |
| 4F-benzoyl-TN14011-iPr | 55 | 4F-benzoyl-Arg-Arg-Nal-Cys-Tyr-Cit-Lys-DGlu-Pro-Tyr-Arg-Cit-Cys-Arg-NHiPr |
| 4F-benzoyl-TN14011-tyramine | 56 | 4F-benzoyl-Arg-Arg-Nal-Cys-Tyr-Cit-Lys-DGlu-Pro-Tyr-Arg-Cit-Cys-Arg-tyramine |
| TA14001 | 57 | H-Ala-Arg-Nal-Cys-Tyr-Arg-Lys-DLys-Pro-Tyr-Arg-Cit-Cys-Arg-OH |
| TA14005 | 58 | H-Arg-Arg-Nal-Cys-Tyr-Ala-Lys-DLys-Pro-Tyr-Arg-Cit-Cys-Arg-OH |
| TA14006 | 59 | H-Arg-Arg-Nal-Cys-Tyr-Arg-Ala-DLys-Pro-Tyr-Arg-Cit-Cys-Arg-OH |
| TA14007 | 60 | H-Arg-Arg-Nal-Cys-Tyr-Arg-Lys-DAla-Pro-Tyr-Arg-Cit-Cys-Arg-OH |
| TA14008 | 61 | H-Arg-Arg-Nal-Cys-Tyr-Arg-Lys-DLys-Ala-Tyr-Arg-Cit-Cys-Arg-OH |
| TA14009 | 62 | H-Arg-Arg-Nal-Cys-Tyr-Arg-Lys-DLys-Pro-Ala-Arg-Cit-Cys-Arg-OH |
| TA14010 | 63 | H-Arg-Arg-Nal-Cys-Tyr-Arg-Lys-DLys-Pro-Tyr-Ala-Cit-Cys-Arg-OH |
| TC14001 | 64 | H-Cit-Arg-Nal-Cys-Tyr-Arg-Lys-DLys-Pro-Tyr-Arg-Cit-Cys-Arg-OH |
| TC14003 | 65 | H-Arg-Arg-Nal-Cys-Tyr-Cit-Lys-DLys-Pro-Tyr-Arg-Cit-Cys-Arg-OH |
| TN14003 | 66 | H-Arg-Arg-Nal-Cys-Tyr-Cit-Lys-DLys-Pro-Tyr-Arg-Cit-Cys-Arg-NH$_2$ |
| TC14004 | 67 | H-Arg-Arg-Nal-Cys-Tyr-Arg-Cit-DLys-Pro-Tyr-Arg-Cit-Cys-Arg-OH |
| TC14012 | 68 | H-Arg-Arg-Nal-Cys-Tyr-Cit-Lys-DCit-Pro-Tyr-Arg-Cit-Cys-Arg-NH$_2$ |
| T-140 | 69 | H-Arg-Arg-Nal-Cys-Tyr-Arg-Lys-DLys-Pro-Tyr-Arg-Cit-Cys-Arg-OH |
| TC14011 | 70 | H-Arg-Arg-Nal-Cys-Tyr-Cit-Lys-DCit-Pro-Tyr-Arg-Cit-Cys-Arg-OH |
| TC14005 | 71 | H-Arg-Arg-Nal-Cys-Tyr-Arg-Lys-DCit-Pro-Tyr-Arg-Cit-Cys-Arg-OH |
| TC14018 | 72 | H-Cit-Arg-Nal-Cys-Tyr-Arg-Lys-DCit-Pro-Tyr-Arg-Cit-Cys-Arg-NH$_2$ |

In each one of SEQ ID NOS:1-72, two cysteine residues are preferably coupled in a disulfide bond.

Currently preferred peptides according to the present invention are peptides having an amino acid sequence as set forth in any one of SEQ ID NOS:1-72. More preferably, it has been previously reported that the T-140 derivatives having an amino acid sequence as set forth in any one of SEQ ID NOS: 1-68 and 70-72 presented in Table 1 may have improved stability in serum and reduced cytotoxicity relative to T-140 (SEQ ID NO:69). However, T-140 may be suitable for use in the methods of the present invention, e.g. when applied by local administration routes.

In another preferable embodiment, the peptide used in the compositions and methods of the invention consists essentially of an amino acid sequence as set forth in SEQ ID NO:1. In another preferable embodiment, the peptide used in the compositions and methods of the invention is of an amino acid sequence as set forth in SEQ ID NO:1. In another embodiment, the peptide is at least 60%, preferably at least 70% and more preferably at least 80% homologous to SEQ ID NO:1. In another embodiment, the peptide is at least about 90% homologous to SEQ ID NO:1. In another embodiment, the peptide is at least homologous to SEQ ID NO:1. In another embodiment, the peptide is at least about 95% homologous to SEQ ID NO:1. Each possibility represents a separate embodiment of the present invention.

In various other particular embodiments, the peptide is selected from SEQ ID NOS:1-72, wherein each possibility represents a separate embodiment of the present invention.

In another particular embodiment, said peptide has an amino acid sequence as set forth in any one of SEQ ID NOS:1-4, 10, 46, 47, 51-56, 65, 66, 68, 70 and 71. In another particular embodiment, said peptide has an amino acid sequence as set forth in any one of SEQ ID NOS:4, 10, 46, 47, 68 and 70. In another particular embodiment, said peptide has an amino acid sequence as set forth in any one of SEQ ID NOS:1, 2, 51, 65 and 66. In another particular embodiment, said peptide has an amino acid sequence as set forth in any one of SEQ ID NOS:53-56.

In a preferable particular embodiment, said peptide has an amino acid sequence as set forth in SEQ ID NO:1. In another particular embodiment, said peptide has an amino acid sequence as set forth in SEQ ID NO:2. In another particular embodiment, said peptide has an amino acid sequence as set forth in SEQ ID NO:51. In another particular embodiment, said peptide has an amino acid sequence as set forth in SEQ ID NO:66.

In another aspect, the invention relates to the use of a pharmaceutical composition comprising a peptide indicated by the following formula (II) or a salt thereof:

```
 1    2   3   4   5  6  7 8 9  10 11 12 13
A₁-Arg-A₂-Cys-Tyr-A₃-A₄-X-A₅-A₆-Cit-Cys-A₇        (II)
``` wherein:
$A_1$ represents a hydrogen atom, or an arginine, lysine, ornithine, citrulline or alanine residue or a N-α-substituted derivative of these amino acids;
$A_2$ represents an aromatic amino acid residue;
$A_3$, $A_4$ and $A_6$ each independently represent an arginine, lysine, ornithine, citrulline or alanine residue;
$A_5$ represents a tyrosine, phenylalanine, alanine, naphthylalanine or citrulline residue;
$A_7$ represents a lysine or arginine residue in which a carboxyl group may be amidated or esterified;
X is selected from the group consisting of:
(i) a peptide residue represented by the following formula (III):

```
  1'  2'  3'  4'   5'  6'
 -A₈-A₉-A₁₀-Gly-A₁₁-A₁₂-                           (III)
``` wherein $A_8$ and $A_{12}$ each independently represents an alanine, valine, leucine, isoleucine, serine, cysteine or methionine residue;
$A_9$ represents an aromatic amino acid residue, $A_{10}$ is selected from the same amino acid residues as in $A_3$, $A_{11}$ represents a tyrosine, phenylalanine, tryptophan, alanine, valine, leucine, isoleucine, serine, cysteine or methionine residue, provided that when both of the 1'-position and the 6'-position are cysteine residues, they may be bonded in a disulfide bond,
(ii) a peptide selected from the group consisting of a D-ornithyl-proline, prolyl-D-ornithine, D-lysyl-proline, prolyl-D-lysine, D-arginyl-proline, prolyl-D-arginine, D-citrullyl-proline, D-citrullyl-alanine, D-alanyl-citrulline, prolyl-D-citrulline, glycyl-ornithine, ornithyl-glycine, glycyl-lysine, lysyl-glycine, glycyl-arginine, arginyl-glycine, glycyl-citrulline, citrullyl-glycine, D-alanyl-proline, and D-lysyl-alanine,
and a hydrogen atom of a side chain ω-amino group of D-arginine, L-arginine, D-lysine, L-lysine, D-ornithine or L-ornithine which are constitutional amino acids of said peptide residues may be substituted by a ω-aminoacyl group,
and the peptide residues of (i) and (ii) represent a peptide residue which binds amino acid residues at the 7-position and the 9-position through a peptide bond;
and the cysteine residues at the 4-position and the 12-position may be bonded in a disulfide bond;
provided that, in the above polypeptide or a salt thereof, either of the amino acid residues of $A_1$, $A_3$, $A_4$, $A_5$, $A_6$ and $A_7$ is an alanine or citrulline residue; or
(iii) a peptide residue containing a D-citrulline, D-alanine, citrulline, or alanine residue) or a salt thereof.

In the polypeptides of the formula (II) of the present invention, $A_1$ is preferably an arginine, alanine or citrulline residue; $A_2$ is preferably a tryptophan or naphthylalanine residue; $A_3$ is preferably arginine, alanine or citrulline residue; $A_4$ is preferably a lysine, alanine or citrulline residue; X is preferably a D-lysyl-proline, D-alanyl-proline, D-lysyl-alanine or D-citrullyl-proline residue; $A_5$ is preferably a tyrosine or alanine residue; $A_6$ is preferably an arginine, alanine or citrulline residue; $A_7$ is preferably an arginine residue.

Exemplary peptides of the formula (II) are peptides wherein $A_1$, $A_6$ and $A_7$ are arginine residues, $A_2$ is a naphthylalanine residue, $A_3$ is a citrulline residue, $A_4$ is a lysine residue, X is a D-lysyl-proline residue, and $A_5$ is a tyrosine residue, a polypeptide of the formula (II) wherein $A_1$, $A_3$, $A_6$ and $A_7$ are arginine residues, $A_2$ is a naphthylalanine residue, $A_4$ is a lysine residue, X is a D-citrullyl-proline residue, and $A_5$ is a tyrosine residue, a polypeptide of the formula (II) wherein $A_1$, $A_6$ and $A_7$ are arginine residues, $A_2$ is a naphthylalanine residue, $A_3$ is a citrulline residue, $A_4$ is a lysine residue, X is a D-citrullyl-proline residue, $A_5$ is a tyrosine residue, and a polypeptide of the formula (II) wherein $A_1$ is a citrulline residue, $A_2$ is a naphthylalanine residue, $A_3$, $A_6$ and $A_7$ are arginine residues, $A_4$ is a lysine residue, X is a D-citrullyl-proline residue, $A_5$ is a tyrosine residue.

The peptides of formula (II) may be exemplified in another embodiment by a peptide of the formula (II) wherein $A_1$, $A_6$ and $A_7$ are arginine residues, $A_2$ is a naphthylalanine residue, $A_3$ is a alanine residue, $A_4$ is a lysine residue, X is a D-lysyl-proline residue, and $A_5$ is a tyrosine residue, a polypeptide of the formula (II) wherein $A_1$ is a citrulline residue, $A_2$ is a naphthylalanine residue, $A_3$, $A_6$ and $A_7$ are arginine residues, $A_4$ is a lysine residue, X is a D-lysyl-proline residue, and $A_5$ is a tyrosine residue, a polypeptide of the formula (II) wherein $A_1$, $A_3$ and $A_7$ are arginine residues, $A_2$ is a naphthylalanine residue, $A_4$ is a lysine residue, X is a D-lysyl-proline residue, $A_5$ is a tyrosine residue, and $A_6$ is a citrulline residue, a polypeptide of the formula (II) wherein $A_1$ and $A_3$ are citrulline residues, $A_2$ is a naphthylalanine residue, $A_4$ is a lysine residue, X is a D-lysyl-proline residue, $A_5$ is a tyrosine residue, $A_6$ and $A_7$ are arginine residues, and a polypeptide of the formula (II) wherein $A_1$, $A_3$ and $A_7$ are arginine residues, $A_2$ is a naphthylalanine residue, $A_4$ is a lysine residue, X is a D-citrullyl-proline residue, $A_5$ is a tyrosine residue, and $A_6$ is a citrulline residue.

The amino acid of $A_7$ as presented in formula II herein is preferably one in which the carboxyl group is amidated for improving stability of the polypeptide in vivo such as in serum, etc.

A peptide of the present invention includes a peptide or its amide, ester or salt containing the amino acid sequence which is substantially the same amino acid sequence as the sequence of any of the above-mentioned peptides. Here, "substantially the same amino acid sequence" means an amino acid sequence that is qualitatively identical in the activity of the peptide or the biological activity of the peptide (e.g. MIP3α secretion) or the like. Accordingly, quantitative variances are acceptable to some extent (e.g. about 0.01 to 100 times, preferably 0.5 to 20 times, or more preferably 0.5 to 2 times). Therefore, one or more of the amino acids in the amino acid sequences indicated in any of the above-mentioned formula (I), (II) and SEQ ID NOS:1-72 can have variances, so far as they have any of the above-mentioned properties. That is to say, in the present invention, any peptide (variant peptide) resulting from the variance in the amino acid sequence such as substitution, deletion or insertion (addition) etc. which brings about any significant change (i.e. a qualitatively different change, or a qualitatively identical but quantitatively significantly different change) in the physiological property or chemical property of the original (non-variant) peptide is deemed as substantially the same as the original (non-variant) peptide having no such variance, and, the amino acid sequence of such variant peptide is deemed as substantially the same as the amino acid sequence of the original (non-variant) peptide.

It is a well-known fact that generally, the changes such as substitution, deletion or insertion (addition) of an amino acid in a peptide sequence often do not make a significant change to physiological properties or chemical properties of such peptide. For example, it is generally considered that substitution of a certain amino acid by another amino acid of similar chemical properties results in a peptide having minimized deviation from the properties of the original peptide.

Amino acids are classified, using the similarity of their properties as to one of the criteria, into the following classes, for example: (i) nonpolar (hydrophobic) amino acids (examples: alanine, leucine, isoleucine, valine, proline, phenylalanine, tryptophan, methionine, etc.); (ii) polar (neutral) amino acids (examples: glycine, serine, threonine, cysteine, tyrosine, asparagine, glutamine, etc.); (iii) basic amino acids carrying positive electric charge (examples: arginine, lysine, histidine, etc.); (iv) acidic amino acids carrying negative electric charge (examples: asparatic acid, glutamic acid, etc.), and accordingly, amino acid substitution within each class can be conservative with regard to the property of a peptide (namely, substitution generating "substantially same" amino acid sequences).

In other words, "substantially the same amino acid sequences" may include:

(i) amino acid sequences wherein 1 or more, or, in other embodiments, 1 to 3 amino acids were substituted by other amino acids in the amino acid sequences indicated in the above-mentioned formula (I), (II) and SEQ ID NOS:1-72;

(ii) amino acid sequences wherein 1 or more, or, in other embodiments, 1 to 3 amino acids were deleted in the amino acid sequences indicated in the above-mentioned formula (I), (II) and SEQ ID NOS:1-72;

(iii) amino acid sequences wherein 1 or more or, in other embodiments, 1 to 3 amino acids were added (inserted) in the amino acid sequences indicated in the above-mentioned formula (I), (II) and SEQ ID NOS:1-72; or (iv) peptides including modifications to amino acids (particularly, the side chains thereof) among the peptides having the amino acid sequences indicated in above (i), (ii) or (iii), or esters, amides or salts thereof.

A peptide of the present invention, if and when the substitution, deletion, insertion (addition), modification, etc. of above (i) to (iv) is intentionally or incidentally provided in the amino acid sequence thereof, can be varied to a stable peptide against heat or protease or a high-activity peptide having more enhanced activity. The peptides of the present invention include also these variant peptides or amides thereof; esters thereof or salts thereof.

Furthermore, among the peptides of the present invention are the peptide consisting of the amino acid sequence indicated in any of the above-mentioned formula (I), (II) and SEQ ID NOS:1-72, and the peptide containing the amino acid sequence sharing the homology of about 50 to 99.9% (preferably, 70 to 99.9%, more preferably 90 to 99.9%) with the foregoing amino acid sequence and having the activities of substantially the same nature as the peptide consisting of the amino acid sequence indicated in any of the above-mentioned formula (I), (II) and SEQ ID NOS:1-72, or amides thereof, esters thereof or salts thereof.

The amides, esters or salts of the peptide having the amino acid sequence indicated in any of the above-mentioned SEQ ID NOS:1-72 include the same ones as are exemplified for the peptide indicated in the above-mentioned formula (I). Preferably, the peptide having the amino acid sequence indicated in any of the above-mentioned SEQ ID NOS:1-72 is amidated at the carboxyl group of the C-terminal amino acid residue.

The peptides of the present invention including the peptide containing the amino acid sequence indicated in any of the above-mentioned SEQ ID NOS:1-72 can be produced by conventionally known methods of synthesizing peptides. For the syntheses of peptides, either solid phase peptide synthesis or liquid phase synthesis may be utilized. Namely, an expected peptide can be produced by condensing a partial peptide able to constitute a peptide or an amino acid with remaining portions, and if the product has a protecting group, by eliminating the protecting group. As the known condensation methods and elimination of protecting groups, the following examples (1) to (5) are included:

(1) M. Bodanszky and M. A. Ondetti, Peptide Synthesis, Interscience Publishers, New York (1966).
(2) Schroeder and Luebke, The Peptide, Academic Press, New York (1965).
(3) N. Izumiya, et. al., Peptide Synthesis, Basics and Practice, Maruzen, Tokyo (1975).
(4) H. Yajima and S. Sakakibara, Seikagaku-Jikken-Koza I, Protein Chemistry IV, Tokyo Kagakudoj in, Tokyo, pp 205 (1977).
(5) H. Yajima, Zoku-Iyakuhin-no-Kaihatsu, Vol. 14, Peptide Synthesis, Hirokawa Publishing Co., Tokyo (1991).

As practical methods for syntheses of peptides, the following examples can be given:

Generally, commercially available resins for synthesis of polypeptides can be used. Such resins include, for example, chloromethyl resin, hydroxymethyl resin, benzhydroxylamine resin, aminomethyl resin, 4-hydroxybenzylalcohol resin, 4-methylbenzhydroxylamine resin, PAM resin, 4-hydroxymethylmethylphenylacetoamidomethyl resin, polyacrylamide resin, 4-(2',4'-dimetoxyphenyl-hydroxymethyl) phenoxy resin, 4-2',4'-dimetoxyphenyl-Fmoc aminoethylphenoxy resin, etc. Using such resin, an amino acid with suitably protected α-amino group and side chain functional group is condensed on the resin to the sequence of the expected polypeptide in accordance with conventionally known condensation methods. In the last stage of the reaction, the polypeptide is cleared from the resin and simultaneously various protective groups are removed, and then, by carrying out intramolecular disulfide bond-forming reaction in highly diluted solution, the expected polypeptide or amide thereof is obtained. For the above-mentioned condensation of the protected amino acid, various activated reagents usable for the syntheses of polypeptides can be used, but it is particularly better to use carboxylmides. Among such carboxylmides are DCC, N,N'-diisopropylcarbodiimide, N-ethyl-N'-(3-dimethylaminopropyl)cabodiimde, etc. For the activation by these, together with racemization inhibitory additives (for example, HOBt, HOOBt), a protected amino acid is added directly to the resin, or after activating the protected amino acid as symmetric acid anhydride or HOBt ester or HOOBt ester, it can be added to ester resin.

Solvents used for the activation of protected amino acids and the condensation with resins can be chosen from among the solvents known to be usable for polypeptide condensation reactions. For example, acid amides such as N,N-dimethylformamide, N,N-dimethylacetoamide and N-methylpyrrolidone, halogenated hydrocarbons such as methylene chloride and chloroform, alcohols such as trifluoroethanol, sulfoxides such as methyl sulfoxide, ethers such as pyridine, dioxane and tetrahydrofuran, nitriles such as acetonitrile and propionitrile, esters such as methyl acetate and ethyl acetate, or appropriated mixtures of the foregoing are used. A solvent used for activation of a protected amino acid or its condensation with resin can be selected from among the solvents known to be usable for condensing reactions of polypeptides. The reaction temperature is appropriately set within the scope known to be applicable to polypeptide bond forming reactions, usually, at −20° C. to 50° C. Activated amino acid derivatives are usually used at 1.5 to 4 times excess. According to the result of tests adopting ninhydrin reaction, if the condensation is insufficient, the repetition of condensation reactions without eliminating protective groups can lead to sufficient condensation. If sufficient condensation is attained by the repetition of reactions, unreacted amino acids can be acetylated by the use of acetic anhydride or acetylimidazole.

The protective group of the amino group used as ingredients include, for example, Z, Boc, tertialypentyloxycarbony, isobornyloxycarbonyl, 4-methoxybenzyloxycabonyl, Cl-Z, Br-Z, adamantyloxycabonyl, trifluoroacetyl, phtaloyl, formyl, 2-nitrophenylsulphenyl, diphenylphosphinothioyl, Fmoc, etc. Carboxyl group can be protected, for example, by alkyl esterification (e.g. straight-chain, branching or circular alkyl esterification of methyl, ethyl, propyl, butyl, tertialbutyl, cyclopentyl, cyclohexyl, cycloheptyl, cyclooctyl, 2-adamantyl, etc.), aralkyl esterification (e.g. benzylester, 4-nitrobenzylester, 4-methoxybenzylester, 4-chlorbenzylester, benzhydryl esterification), phenacylesterification, benzylcarbonylhydrazidation, tertialybutoxycarbonylhydrazidation, tritylhydrazidation, etc. The hydroxyl group of serine can be protected, for example, by esterification or etherification. The groups suitable for this eterification include, for example, groups derivatized from carboxylic acid such as lower alkanoyl group such as acetyl group, aroyl group such as benzoyl group, benzyloxycarbonyl group, ethoxycarbonyl group. The groups suitable for etherification include, for example, benzyl group, tetrahydropiranyl group, tertiarybutyl group, etc. As the protective groups of phenolic OH group of tyrosine, for example, Bzl, Cl2-Bzl, 2-nitrobenzyl, Br-Z, tertiarlybutyl, etc. are used. As the protective groups of imidazole of histidine, for example, Tos, 4-methoxy-2,3,6-trimethylbenzenesulfonyl, DNP, benzyloxymethyl, Bum, Boc, Trt, Fmoc etc. are used.

Ingredients with activated carboxyl groups include, for example, corresponding acid anhydride, azide, active ester [ester of alcohol (e.g. pentachlorophenol, 2,4,5-trichlorophenol, 2,4-dinitrophenol, cyanomethylalcohol, p-nitrophenol, HONB, N-hydroxysuccimide, N-hydroxyphtalimide, HOBO] are used. Ingredients with activated amino group include, for example, corresponding phosphoric amide. As the methods to remove (elimiate) protective groups, for example, catalytic reduction in hydrogen airstream in the presence of a catalyst such as Pd-black or Pd-carbon, acid treatment by anhydrous hydrogen fluoride, methanesulfonic acid, trifluoromethanesulfonic acid, trifluoroacetic acid or a mixture thereof, etc, base treatment by diisopropylethylamine, triethylamine, piperidine, piperadine, etc., and reduction by natrium in liquid ammonia are used. Elimination reaction by the above-mentioned acid treatment is done generally at the temperature of about −20° C. to 40° C., but in the acid treatment, it is effective to add a cation trapping agent such as anisole, phenol, thioanisole, m-cresol, p-cresol, dimethylsulfide, 1,4-butanedithiol, 1,2-ethanedithiol. 2,4-dinitrophenyl group used as the protective group of imidazole of histidine is removed by thiophenol treatment. Formyl group used as the protective group of indole of tryptophan is removed by elimination of protection by the above-mentioned acid treatment in the presence of 1,2-ethanedithiol, 1,4-butanedithiol, etc. and also is removed by alkaline treatment by dilute sodium hydroxide solution, dilute ammonia, etc.

Protection and protective group of functional groups not to be involved in the reaction of ingredients, and elimination of such protective group, and activation of functional groups to be involved in the reaction, etc. can be appropriately selected from among conventionally known groups or conventionally known measures. As alternative methods to obtain amides of polypeptides, there is, for example, a method to manufacture, after amidating and protecting α-carboxyl group of carboxy-terminal amino acid and then extending the peptide chain to the desired chain length on the side of amino group, a polypeptide eliminating the protective group of α-amino group of N-terminus of such peptide chain and a polypeptide eliminating the protective group of carboxyl group of C-terminus, and then these two peptides are condensed in the above-mentioned mixed solvent. The details of the condensation reaction are the same as described above. After purifying the protected polypeptide obtained by the condensation, the desired raw polypeptide can be obtained by eliminating all the protective groups by the above-mentioned method. Having purified this raw polypeptide using various known purification methods, if the main fraction is freeze-dried, an amide type of the desired polypeptide can be obtained. To get an ester type of the polypeptide, for example, make an amino acid ester by condensing α-carboxyl group of carboxy-terminal amino acid with the desired alcohols, and then, the ester type of the desired polypeptide can be obtained in the same way as the amide type of the polypeptide.

After the reaction, the peptides of the present invention can be purified and isolated by combining usual purification methods such as solvent extraction, distillation, column chromatography, liquid chromatography, re-crystallization, etc. If a peptide obtained by the above-mentioned methods is a salt-free type, it can be converted to a suitable salt by known methods, or if such peptide is a salt, it can be converted to a salt-free type by known methods.

CXCR4 Agonists

Although peptides of the T-140 analog family as detailed herein are preferably used in the compositions and methods of the invention, and have been found superior to the natural ligand of CXCR4, namely CXCL12, in certain other embodiments other compounds having CXCR4 agonist activity may be used.

In one embodiment, the compound is a CXCR4 agonist. In another embodiment, the compound is a CXCR4 partial agonist (having similar or lower activity compared to CXCL12). In yet another embodiment, the compound is a CXCR4 super-agonist (having increased activity compared to CXCL12).

A "CXCR4 agonist" for use in the invention is an agent that can bind a CXCR4 receptor expressed on a target cell, e.g. a dendritic cell, and mediates secretion of MIP3α in a CXCR4 dependent manner. The term encompasses natural proteins of the body such as the chemokine ligand of CXCR4, CCL12 (also known as SDF-1). The term also includes variants of said chemokine. Such variants will continue to possess the desired activity discussed above. Variants refers to a polypeptide derived from the native protein by deletion or addition of one or more amino acids to the N-terminal and/or C-terminal end of the native protein; deletion or addition of one or more amino acids at one or more sites in the native protein; or substitution of one or more amino acids at one or more sites in the native protein. Such variants include mutants, fragments, allelic variants, homologous orthologs, and fusions of native protein. Chemokine receptor agonists may also be modified by glycosylation, phosphorylation, substitution of non-natural amino acid analogs and the like. Other CXCR4 agonists, partial agonists and super-agonists are known in the art, and may be used as long as they retain the activity of CXCL12 with respect to MIP3α. For example, such agonist may include e.g. polypeptides, peptides, small organic molecules and the like, which are able to selectively bind CXCR4 and act as a CXCL12 agonist as detailed herein. Preparation and use of such inhibitors is within the abilities of those of skill in the art.

In another embodiment, the CXCR4 agonist is an antibody-based moiety directed against the CXCR4 receptor, which antibody-based moiety is capable of acting as a CXCL12 agonist. Such molecules include, but are not limited to: monoclonal antibodies, polyclonal antibodies, and antibody fragments such as recombinant antibody fragments, single-chain antibodies (scFv), single antibody variable domains, and the like. Single-chain antibodies are small recognition units consisting of the variable regions of the immunoglobulin heavy ($V_H$) and light ($V_L$) chains which are connected by a synthetic linker sequence. Single antibody domain proteins (dAbs) are minimized antibody fragments comprising either an individual $V_L$ domain or an individual $V_H$ domain.

Methods of generating monoclonal and polyclonal antibodies are well known in the art. Antibodies may be generated via any one of several known methods, which may employ induction of in vivo production of antibody molecules, screening of immunoglobulin libraries, or generation of monoclonal antibody molecules by continuous cell lines in culture. These include, but are not limited to, the hybridoma technique, the human B-cell hybridoma technique, and the Epstein-Barr virus (EBV)-hybridoma technique. Antibody fragments may be obtained using methods well known in the art, including, but not limited to by proteolytic hydrolysis of the antibody or by expression in E. coli or mammalian cells (e.g., Chinese hamster ovary (CHO) cell culture or other protein expression systems) of DNA encoding the fragment. F(ab')$_2$ antibody fragments can be produced by enzymatic cleavage of antibodies with pepsin to provide a 5S fragment. This fragment can be further cleaved using a thiol reducing agent, and optionally a blocking group for the sulfhydryl groups resulting from cleavage of disulfide linkages, to produce 3.5S Fab' monovalent fragments. Alternatively, enzymatic cleavage using pepsin produces two monovalent Fab' fragments and an Fc fragment directly. Other methods of cleaving antibodies, such as separation of heavy chains to form monovalent light-heavy chain fragments, further cleavage of fragments, or other enzymatic, chemical, or genetic techniques may also be used, so long as the fragments retain the ability to bind to the antigen that is recognized by the intact antibody. An Fv is composed of paired heavy chain variable and light chain variable domains. This association may be non-covalent. Alternatively, as described hereinabove, the variable domains may be linked to generate a single-chain Fv by an intermolecular disulfide bond, or alternately such chains may be cross-linked by chemicals such as glutaraldehyde. Preferably, the Fv is a single-chain Fv. Single-chain Fvs are prepared by constructing a structural gene comprising DNA sequences encoding the heavy chain variable and light chain variable domains connected by an oligonucleotide encoding a peptide linker. The structural gene is inserted into an expression vector, which is subsequently introduced into a host cell such as E. coli. The recombinant host cells synthesize a single polypeptide chain with a linker peptide bridging the two variable domains. In addition, techniques may be utilized to change a "murine" antibody to a "human" antibody, without altering the binding specificity of the antibody.

An antibody "reactive fragment", as used herein, denotes any molecule comprising the antigen-binding reactive fraction of an antibody. An "antibody or active fragment thereof" as used herein includes, but is not limited to, intact immunoglobulin molecules of any isotype and generated by any animal cell line or microorganism, the antigen-binding reactive fraction thereof, including, but not limited to, the Fab fragment, the Fab' fragment, the F(ab')$_2$ fragment, the variable portion of the heavy and/or light chains thereof, Fab miniantibodies (see e.g. WO 93/15210, U.S. patent application Ser. No. 08/256,790, WO 96/13583, U.S. patent application Ser. No. 08/817,788, WO 96/37621, U.S. patent application Ser. No. 08/999,554, the entire contents of which are incorporated herein by reference), dimeric bispecific miniantibodies and chimeric or single-chain antibodies incorporating such reactive fraction, as well as any other type of molecule or cell in which such antibody reactive fraction has been physically inserted, such as a chimeric T-cell receptor. Such molecules may be provided by any known technique, including, but not limited to, enzymatic cleavage, peptide synthesis or recombinant techniques.

Pharmaceutical Compositions

As used herein, a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Hereinafter, the phrases "physiologically acceptable carrier" and "pharmaceutically acceptable carrier", which may be used interchangeably, refer to a carrier or a diluent that does not cause significant irritation to an organism and does not abrogate the biological activity and properties of the administered compound.

Herein, the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils, and polyethylene glycols.

Techniques for formulation and administration of drugs may be found in the latest edition of "Remington's Pharmaceutical Sciences", Mack Publishing Co., Easton, Pa., which is herein fully incorporated by reference (Remington: The Science and Practice of Pharmacy, Gennaro, A., Lippincott, Williams & Wilkins, Philidelphia, Pa., $20^{th}$ ed, 2000).

Pharmaceutical compositions of the present invention may be manufactured by processes well known in the art, e.g., by means of conventional mixing, dissolving, granulating, dragee-making, levigating, emulsifying, encapsulating, entrapping, or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations that can be used pharmaceutically. Proper formulation is dependent upon the route of administration chosen.

The pharmaceutical compositions of the invention are suitable for administration systemically or in a local manner, for example, via injection of the pharmaceutical composition directly into a tissue region of a patient (e.g. intralesional injection).

For injection, the active ingredients of the pharmaceutical composition may be formulated in aqueous solutions, preferably in physiologically compatible buffers such as Hank's solution, Ringer's solution, or physiological salt buffer.

Pharmaceutical compositions for parenteral administration include aqueous solutions of the active preparation in water-soluble form. Additionally, suspensions of the active ingredients may be prepared as appropriate oily or water-based injection suspensions. Suitable lipophilic solvents or vehicles include fatty oils such as sesame oil, or synthetic fatty acid esters such as ethyl oleate, triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active ingredients, to allow for the preparation of highly concentrated solutions.

Alternatively, the active ingredient may be in powder form for constitution with a suitable vehicle, e.g., a sterile, pyrogen-free, water-based solution, before use.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries as desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, and sodium carbomethylcellulose; and/or physiologically acceptable polymers such as polyvinylpyrrolidone (PVP). If desired, disintegrating agents, such as cross-linked polyvinyl pyrrolidone, agar, or alginic acid or a salt thereof, such as sodium alginate, may be added.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions that can be used orally include push-fit capsules made of gelatin, as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate, and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

Pharmaceutical compositions suitable for use in the context of the present invention include compositions wherein the active ingredients are contained in an amount effective to achieve the intended purpose. Determination of a therapeutically effective amount is well within the capability of those skilled in the art, especially in light of the detailed disclosure provided herein.

In one aspect, the invention provides a vaccine composition comprising: (i) at least one antigen; (ii) at least one pharmaceutically acceptable adjuvant comprising a peptide having an amino acid sequence as set forth in SEQ ID NO:1 or an analog or derivative thereof in an amount sufficient to increase the immunogenicity of the at least one antigen; and (iii) a pharmaceutically acceptable carrier, excipient or diluent.

The term "antigen" means a substance that is recognized and bound specifically by an antibody or by a T cell antigen receptor. Antigens can include for example peptides, proteins, glycoproteins, polysaccharides, complex carbohydrates, sugars, gangliosides, lipids and phospholipids; portions thereof and combinations thereof. The antigens can be those found in nature or can be synthetic. Antigens suitable for administration with the peptide adjuvants of the invention include any molecule capable of eliciting a B cell or T cell antigen-specific response.

In various embodiments the antigen is selected from the group consisting of: proteins, peptides, attenuated or killed microorganisms or cells (e.g. cancer cells, bacteria and viruses), saccharides (e.g. bacterial polysaccharides, oligosaccharides and lipopolysaccharides), antibodies and antibody active fragments (e.g. Fv, single-chain Fv, Fab, Fab', and F(ab')$_2$). In a particular embodiment the antigen is a tumor-associated antigen (or an epitopic portion thereof).

Tumor-associated antigens suitable for use in the subject invention include both mutated and non-mutated molecules which may be indicative of single tumor type, shared among several types of tumors, and/or exclusively expressed or overexpressed in tumor cells in comparison with normal cells. In addition to proteins and glycoproteins, tumor-specific patterns of expression of carbohydrates, gangliosides, glycolipids and mucins have also been documented. Exemplary tumor-associated antigens for use in the subject cancer vaccines include protein products of oncogenes, tumor suppressor genes and other genes with mutations or rearrangements unique to tumor cells, reactivated embryonic gene products, oncofetal antigens, tissue-specific (but not tumor-specific) differentiation antigens, growth factor receptors, cell surface carbohydrate residues, foreign viral proteins and a number of other self proteins.

Specific embodiments of tumor-associated antigens include, e.g., mutated antigens such as the protein products of the Ras p21 protooncogenes, tumor suppressor p53 and HER-2/neu and BCR-ab1 oncogenes, as well as CDK4, MUM1, Caspase 8, and Beta catenin; overexpressed antigens such as galectin 4, galectin 9, carbonic anhydrase, Aldolase A, PRAME, Her2/neu, ErbB-2 and KSA, oncofetal antigens such as alpha fetoprotein (AFP), human chorionic gonadotropin (hCG); self antigens such as carcinoembryonic antigen (CEA) and melanocyte differentiation antigens such as Mart 1/Melan A, gp100, gp75, Tyrosinase, TRP1 and TRP2; prostate associated antigens such as PSA, PAP, PSMA, PSM-P1 and PSM-P2; reactivated embryonic gene products such as MAGE 1, MAGE 3, MAGE 4, GAGE 1, GAGE 2, BAGE, RAGE, and other cancer testis antigens such as NY-ESO1, SSX2 and SCP1; mucins such as Muc-1 and Muc-2; gangliosides such as GM2, GD2 and GD3, neutral glycolipids and glycoproteins such as Lewis (y) and globo-H; and glycoproteins such as Tn, Thompson-Freidenreich antigen (TF) and sTn. Also included as tumor-associated antigens herein are whole cell and tumor cell lysates as well as immunogenic portions thereof, as well as immunoglobulin idiotypes expressed on monoclonal proliferations of B lymphocytes for use against B cell lymphomas.

Tumor-associated antigens and their respective tumor cell targets include, e.g., cytokeratins, particularly cytokeratin 8, 18 and 19, as antigens for carcinoma. Epithelial membrane antigen (EMA), human embryonic antigen (HEA-125), human milk fat globules, MBr1, MBr8, Ber-EP4, 17-1A, C26 and T16 are also known carcinoma antigens. Desmin and muscle-specific actin are antigens of myogenic sarcomas. Placental alkaline phosphatase, beta-human chorionic gonadotropin, and alpha-fetoprotein are antigens of trophoblastic and germ cell tumors. Prostate specific antigen is an antigen of prostatic carcinomas, carcinoembryonic antigen of colon adenocarcinomas. HMB-45 is an antigen of melanomas. In cervical cancer, useful antigens could be encoded by human papilloma virus. Chromagranin-A and synaptophysin are antigens of neuroendocrine and neuroectodermal tumors. Of particular interest are aggressive tumors that form solid tumor masses having necrotic areas. The lysis of such necrotic cells is a rich source of antigens for antigen-presenting cells, and thus the subject therapy may find advantageous use in conjunction with conventional chemotherapy and/or radiation therapy.

Tumor-associated antigens (and other antigens of the present invention) can be prepared by methods well known in the art. For example, these antigens can be prepared from their natural source (e.g. cancer cells) either by preparing crude extracts of e.g. cancer cells, by partially purifying the antigens, by recombinant technology, or by de novo synthesis of known antigens. The antigen may also be in the form of a nucleic acid encoding an antigenic peptide in a form suitable for expression in a subject and presentation to the immune system of the immunized subject. Further, the antigen may be a complete antigen, or it may be a fragment of a complete antigen comprising at least one epitope In other embodiments, the antigen is a viral antigen, a bacterial antigen, a fungal antigen and a parasite-derived antigen.

Exemplary viral pathogens include, but are not limited to, infectious viruses that infect mammals, and more particularly humans. Examples of infectious virus include, but are not limited to: Retroviridae (e.g., human immunodeficiency viruses, such as HIV-1, also referred to as HTLV-III, LAV or HTLV-III/LAV, or HIV-III; and other isolates, such as HIV-LP); Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviradae (e.g. vesicular stomatitis viruses, rabies viruses); Coronaviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae herpes simplex virus (HSV) 1 and 2, varicella zoster virus, cytomegalovirus (CMV), herpes virus; Poxyiridae (variola viruses, vaccinia viruses, pox viruses); and Iridoviridae (e.g. African swine fever virus).

Also, gram negative and gram positive bacteria may be targeted by the subject compositions and methods. Such gram positive bacteria include, but are not limited to Pasteurella species, Staphylococci species, and Streptococcus species. Gram negative bacteria include, but are not limited to, Escherichia coli, Pseudomonas species, and Salmonella species. Specific examples of infectious bacteria include but are not limited to: Helicobacter pyloris, Borella burgdorferi, Legionella pneumophilia, Mycobacteria sps (e.g. M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes (Group A Streptococcus), Streptococcus agalactiae (Group B Streptococcus), Streptococcus (viridans group), Streptococcus faecalis, Streptococcus bovis, Streptococcus (anaerobic sps.), Streptococcus pneumoniae, pathogenic Campylobacter sp., Enterococcus sp., Haemophilus infuenzae, Bacillus antracis, corynebacterium diphtheriae, corynebacterium sp., Erysipelothrix rhusiopathiae, Clostridium perfringers, Clostridium tetani, Enterobacter aerogenes, Klebsiella pneumoniae, Pasturella multocida, Bacteroides sp., Fusobacterium nucleatum, Streptobacillus moniliformis, Treponema pallidium, Treponema pertenue, Leptospira, Rickettsia, and Actinomyces israelli.

Polypeptides of bacterial pathogens which may find use as sources of microbial antigens in the subject compositions include but are not limited to an iron-regulated outer membrane protein, ("IROMP"), an outer membrane protein ("OMP"), and an A-protein of Aeromonis salmonicida which causes furunculosis, p57 protein of Renibacterium salmoninarum which causes bacterial kidney disease ("BKD"), major surface associated antigen ("MSA"), a surface expressed cytotoxin ("MPR"), a surface expressed hemolysin ("ISH"), and a flagellar antigen of Yersiniosis; an extracellular protein ("ECP"), an iron-regulated outer membrane protein ("IROMP"), and a structural protein of Pasteurellosis; an OMP and a flagellar protein of Vibrosis anguillarum and V. ordalii; a flagellar protein, an OMP protein, aroA, and purA of Edwardsiellosis ictaluri and E. tarda; and surface antigen of Ichthyophthirius; and a structural and regulatory protein of Cytophaga columnari; and a structural and regulatory protein of Rickettsia. Such antigens can be isolated or prepared recombinantly or by any other means known in the art.

Examples of pathogens further include, but are not limited to, infectious fungi that infect mammals, and more particularly humans. Examples of infectious fungi include, but are not limited to: Cryptococcus neoformans, Histoplasma capsulatum, Coccidioides immitis, Blastomyces dermatitidis, Chlamydia trachomatis, Candida albicans. Examples of infectious parasites include Plasmodium such as Plasmodium falciparum, Plasmodium malariae, Plasmodium ovale, and Plasmodium vivax. Other infectious organisms (i.e. protists) include Toxoplasma gondii. Polypeptides of a parasitic pathogen include but are not limited to the surface antigens of Ichthyophthirius.

Microbial antigens can be prepared by methods well known in the art. For example, these antigens can be prepared directly from viral and bacterial cells either by preparing crude extracts, by partially purifying the antigens, or alternatively by recombinant technology or by de novo synthesis of known antigens. The antigen may also be in the form of a nucleic acid encoding an antigenic peptide in a form suitable for expression in a subject and presentation to the immune system of the immunized subject. Further, the antigen may be a complete antigen, or it may be a fragment of a complete antigen comprising at least one epitope.

The vaccine composition may optionally comprise additional adjuvants such as vegetable oils or emulsions thereof, surface active substances, e.g., hexadecylamin, octadecyl amino acid esters, octadecylamine, lysolecithin, dimethyl-dioctadecylammonium bromide, N,N-dicoctadecyl-N'—N' bis(2-hydroxyethyl-propane diamine), methoxyhexadecylglycerol, and pluronic polyols; polyamines, e.g., pyran, dextransulfate, poly IC, carbopol; peptides, e.g., muramyl dipeptide, dimethylglycine, tuftsin; immune stimulating complexes; oil emulsions (including, but not limited to, oil-in-water emulsions having oil droplets in the submicron range, such as those disclosed by U.S. Pat. Nos. 5,961,970, 4,073,943 and 4,168,308); liposaccharides such as MPL® and mineral gels. The antigens and T-140 analog peptide adjuvants can also be incorporated into liposomes, cochleates, biodegradable polymers such as poly-lactide, poly-glycolide and poly-lactide-co-glycolides, or ISCOMS (immunostimulating complexes), and supplementary active ingredients may also be employed. The protein and peptide antigens of the present invention can be coupled to albumin or to other carrier molecule in order to modulate or enhance the immune response, all as are well known to those of ordinary skill in the vaccine art.

The vaccines can be administered to a human or animal by a variety of routes, including but not limited to parenteral, intradermal, transdermal (such as by the use of slow release polymers), intramuscular, intraperitoneal, intravenous, subcutaneous, oral and intranasal routes of administration, according to protocols well known in the art. The particular dosage of the conjugate antigen will depend upon the age, weight and medical condition of the subject to be treated, as well as on the identity of the antigen and the method of administration. Suitable doses will be readily determined by the skilled artisan.

In another embodiment, there is provided a DNA vaccine composition comprising a nucleic acid sequence encoding at least one antigen and an adjuvant comprising a T-140 analog or a nucleic acid sequence encoding same. Thus another embodiment of the invention provides a DNA vaccine comprising: (i) a recombinant construct comprising a nucleic acid sequence encoding at least one antigen operably linked to at least one transcription control sequence; (ii) at least one pharmaceutically acceptable adjuvant comprising a peptide having an amino acid sequence as set forth in SEQ ID NO:1 or an analog or derivative thereof in an amount sufficient to increase the immunogenicity of the at least one antigen; and (iii) a pharmaceutically acceptable carrier, excipient or diluent.

The nucleic acid molecules may include DNA, RNA, or derivatives of either DNA or RNA. An isolated nucleic acid sequence encoding a viral antigen or a HSP60 peptide can be obtained from its natural source, either as an entire (i.e., complete) gene or a portion thereof. A nucleic acid molecule can also be produced using recombinant DNA technology (e.g., polymerase chain reaction (PCR) amplification, cloning) or chemical synthesis. Nucleic acid sequences include natural nucleic acid sequences and homologs thereof, including, but not limited to, natural allelic variants and modified nucleic acid sequences in which nucleotides have been inserted, deleted, substituted, and/or inverted in such a manner that such modifications do not substantially interfere with the nucleic acid molecule's ability to encode a functional peptide of the present invention.

A nucleic acid molecule homolog can be produced using a number of methods known to those skilled in the art (see, for example, Sambrook et al., Molecular Cloning: A Laboratory Manual, Cold Spring Harbor Labs Press, 1989). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologs can be selected from a mixture of modified nucleic acids by screening for the function of the protein encoded by the nucleic acid e.g. with respect to the induction of the desired immune response.

The oligonucleotides or polynucleotides of the invention may contain a modified internucleoside phosphate backbone to improve the bioavailability and hybridization properties of the oligonucleotide or polynucleotide. Linkages are selected from the group consisting of phosphodiester, phosphotriester, methylphosphonate, phosphoroselenoate, phosphorodiselenoate, phosphoroanilothioate, phosphoroanilidate, phosphoramidate, phosphorothioate, phosphorodithioate or combinations thereof.

Additional nuclease linkages include alkylphosphotriester such as methyl- and ethylphosphotriester, carbonate such as carboxymethyl ester, carbamate, morpholino carbamate, 3'-thioformacetal, silyl such as dialkyl (C1-C6)- or diphenyl-silyl, sulfamate ester, and the like.

The DNA vaccines of the present invention includes a nucleic acid sequence encoding an antigen operably linked to one or more transcription control sequences to form a recombinant molecule. The phrase "operably linked" refers to linking a nucleic acid sequence to a transcription control sequence in a manner such that the molecule is able to be expressed when transfected (i.e., transformed, transduced or transfected) into a host cell. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Exemplary transcription control sequences include, but are not limited to RSV control sequences, CMV control sequences, retroviral LTR sequences, SV-40 control sequences and β-actin control sequences as well as other sequences capable of controlling gene expression in eukaryotic cells. Additional suitable transcription control sequences include tissue-specific promoters and enhancers.

According to still further features in the described preferred embodiments the recombinant construct is a eukaryotic expression vector.

According to still further features in the described particular embodiments the expression vector is selected from the group consisting of pcDNA3, pcDNA3.1(+/−), pZeoSV2 (+/−), pSecTag2, pDisplay, pEF/myc/cyto, pCMV/myc/cyto, pCR3.1, pCI, pBK-RSV, pBK-CMV, pTRES and their derivatives.

According to the present invention, a host cell can be transfected in vivo (i.e., in an animal) or ex vivo (i.e., outside of an animal). Transfection of a nucleic acid molecule into a host cell can be accomplished by any method by which a nucleic acid molecule can be inserted into the cell. Transfection techniques include, but are not limited to, transfection, electroporation, microinjection, lipofection, adsorption, and protoplast fusion. Preferred methods to transfect host cells in vivo include lipofection and adsorption.

It may be appreciated by one skilled in the art that use of recombinant DNA technologies can improve expression of transfected nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, and deletion of sequences that destabilize transcripts. The activity of an expressed recombinant protein of the present invention may be improved by fragmenting, modifying, or derivatizing nucleic acid molecules encoding such a protein.

In another embodiment of the present invention, a DNA vaccine composition further comprises a pharmaceutically acceptable carrier. With respect to DNA vaccines, a "carrier" refers to any substance suitable as a vehicle for delivering a nucleic acid sequence of the present invention to a suitable in vivo site. As such, carriers can act as a pharmaceutically acceptable excipient of a therapeutic composition containing a nucleic acid molecule of the present invention. Preferred carriers are capable of maintaining a nucleic acid molecule of the present invention in a form that, upon arrival of the nucleic acid molecule to a cell, the nucleic acid molecule is capable of entering the cell and being expressed by the cell. Carriers for DNA vaccines of the present invention include: (1) excipients or formularies that transport, but do not specifically target a nucleic acid molecule to a cell (referred to herein as non-targeting carriers); and (2) excipients or formularies that deliver a nucleic acid molecule to a specific site in an animal or a specific cell (i.e., targeting carriers). Examples of non-targeting carriers include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity.

Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- and o-cresol, formalin and benzol alcohol. Preferred auxiliary substances for aerosol delivery include surfactant substances non-toxic to an animal, for example, esters or partial esters of fatty acids containing from about six to about twenty-two carbon atoms. Examples of esters include, caproic, octanoic, lauric, palmitic, stearic, linoleic, linolenic, olesteric, and oleic acids. Other carriers can include metal particles (e.g., gold particles) for use with, for example, a biolistic gun through the skin. Therapeutic compositions of the present invention can be sterilized by conventional methods.

Targeting carriers are herein referred to as "delivery vehicles". Delivery vehicles of the present invention are capable of delivering a therapeutic composition of the present invention to a target site in an animal. A "target site" refers to a site in an animal to which one desires to deliver a therapeutic composition. Examples of delivery vehicles include, but are not limited to, artificial and natural lipid-containing delivery vehicles. Natural lipid-containing delivery vehicles include cells and cellular membranes. Artificial lipid-containing delivery vehicles include liposomes and micelles. A delivery vehicle of the present invention can be modified to target to a particular site in an animal, thereby targeting and making use of a nucleic acid molecule of the present invention at that site. Suitable modifications include manipulating the chemical formula of the lipid portion of the delivery vehicle and/or introducing into the vehicle a compound capable of specifically targeting a delivery vehicle to a preferred site, for example, a preferred cell type. Specifically targeting refers to causing a delivery vehicle to bind to a particular cell by the interaction of the compound in the vehicle to a molecule on the surface of the cell. Suitable targeting compounds include ligands capable of selectively (i.e., specifically) binding another molecule at a particular site. Examples of such ligands include antibodies, antigens, receptors and receptor ligands. For example, an antibody specific for an antigen found on the surface of a cancer cell can be introduced to the outer surface of a liposome delivery vehicle so as to target the delivery vehicle to the cancer cell. Manipulating the chemical formula of the lipid portion of the delivery vehicle can modulate the extracellular or intracellular targeting of the delivery vehicle. For example, a chemical can be added to the lipid formula of a liposome that alters the charge of the lipid bilayer of the liposome so that the liposome fuses with particular cells having particular charge characteristics.

In order to treat an animal with disease or infection, a DNA vaccine composition of the present invention is administered to the animal in an effective manner such that the composition is capable of treating that animal from disease or infection. For example, a recombinant molecule, when administered to an animal in an effective manner, is able to stimulate effector cell immunity in a manner that is sufficient to alleviate the disease afflicting the animal. According to the present invention, treatment of a disease refers to alleviating a disease and/or preventing the development of a secondary disease resulting from the occurrence of a primary disease. An effective administration protocol (i.e., administering a DNA vaccine composition in an effective manner) comprises suitable dose parameters and modes of administration that result in treatment of a disease. Effective dose parameters and modes of administration can be determined using methods standard in the art for a particular disease. Such methods include, for example, determination of survival rates, side effects (i.e., toxicity) and progression or regression of disease. In particular, the effectiveness of dose parameters and modes of administration of a therapeutic composition of the present invention when treating inflammatory diseases can be determined by assessing response rates. Such response rates refer to the percentage of treated patients in a population of patients that respond with either partial or complete remission.

A DNA vaccine composition is administered to an animal in a fashion to enable expression of the administered recombinant molecule of the present invention into a curative protein in the animal to be treated for disease. A DNA vaccine composition can be administered to an animal in a variety of methods including, but not limited to, local administration of the composition into a site in an animal, and systemic administration.

DNA vaccine compositions to be delivered by local administration include: (a) recombinant molecules of the present invention in a non-targeting carrier (e.g., as "naked" DNA molecules, such as is taught, for example in Wolff et al., 1990, Science 247, 1465-1468); and (b) recombinant molecules of the present invention complexed to a delivery vehicle of the present invention. Suitable delivery vehicles for local administration comprise liposomes. Delivery vehicles for local administration can further comprise ligands for targeting the vehicle to a particular site.

DNA vaccine compositions useful in systemic administration, include recombinant molecules of the present invention complexed to a targeted delivery vehicle of the present invention. Suitable delivery vehicles for use with systemic administration comprise liposomes comprising ligands for targeting the vehicle to a particular site. Systemic administration is particularly advantageous when organs, in particular difficult to reach organs (e.g., heart, spleen, lung or liver) are the targeted sites of treatment.

Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., Proc. Natl. Acad. Sci. USA 189: 11277-11281, 1992, which is incorporated herein by reference in its entirety). Oral delivery can be performed by complexing a DNA vaccine composition of the present invention to a carrier capable of withstanding degradation by digestive enzymes in the gut of an animal. Examples of such carriers, include plastic capsules or tablets, such as those known in the art. Topical delivery can be performed by mixing a therapeutic composition of the present invention with a lipophilic reagent (e.g., DMSO) that is capable of passing into the skin.

Therapeutic Uses

In another aspect, there is provided a method for enhancing the immunogenicity of an antigen, comprising combining the antigen with a peptide having an amino acid sequence as set forth in SEQ ID NO:1 or an analog or derivative thereof in an amount sufficient to increase the immunogenicity of said antigen.

In another aspect, there is provided a method for stimulating or enhancing in a subject in need thereof an immune response to an antigen, comprising administering to the subject an immunogenic amount of the antigen and an immunogenicity-augmenting amount of a peptide having an amino acid sequence as set forth in SEQ ID NO:1 or an analog or derivative thereof in concurrent or sequential combination with said antigen.

An "immunogenic amount" of an antigen indicates an amount that is sufficient to stimulate a beneficial immune response, when administered with an adjuvant of the invention. The amount of antigen necessary to provide an immunogenic amount is readily determined by one of ordinary skill in the art. For example, an immune response may be determined by measuring serum antibody titer (e.g. by ELISA), antigen-induced swelling in the skin, and the like.

In another aspect, there is provided a method for enhancing the immunogenicity of a tumor characterized by CXCR4 membrane expression (e.g leukemia) in a subject in need thereof, comprising administering to the subject (e.g. by intralesional injection to the tumor site) a peptide having an amino acid sequence as set forth in SEQ ID NO:1 or an analog or derivative thereof in an amount sufficient to increase the immunogenicity of said tumor.

In another aspect, there is provided a method for immunizing a subject in need thereof, comprising administering to the subject an effective amount of a vaccine composition of the invention, as detailed herein.

By the term "immunizing a subject" is meant administering to the subject a composition of the invention, in an amount effective to elicit or enhance a beneficial immune response in said subject (e.g. administration of a vaccine of the invention elicits an immune response against the antigen, and subsequently provides enhanced protection against the pathogen from which said antigen is derived). While this disclosure generally discusses immunization in the context of prophylactic methods of protection, the term "immunizing" is meant to refer to both prophylactic and therapeutic methods. Accordingly, the present invention may be used as a vaccine for prophylactic protection or in a therapeutic manner; that is, as immunotherapeutic methods and preparations.

In another aspect, the invention provides a method for inducing or enhancing secretion of MIP3α from cells characterized by CXCR4 membrane expression, comprising contacting the cells with a compound having CXCR4 agonistic properties, preferably a peptide having an amino acid sequence as set forth in SEQ ID NO:1 or an analog or derivative thereof. In one embodiment, the cells are malignant cells.

In another aspect, there is provided a method for stimulating or enhancing in a subject in need thereof an immune response to an antigen, comprising administering to the subject an immunogenic amount of a recombinant construct comprising a nucleic acid sequence encoding the antigen, the nucleic acid sequence being operably linked to at least one transcription control sequence, and an immunogenicity-augmenting amount of a compound having CXCR4 agonistic properties in concurrent or sequential combination with said antigen, preferably a peptide having an amino acid sequence as set forth in SEQ ID NO:1 or an analog or derivative thereof.

In another aspect, the invention is directed to the use of a pharmaceutical composition comprising a compound having CXCR4 agonistic properties, preferably a peptide having an amino acid sequence as set forth in SEQ ID NO:1 or an analog or derivative thereof for the preparation of a medicament for enhancing the immunogenicity of an antigen, for enhancing the immunogenicity of a tumor characterized by CXCR4 membrane expression, and/or for inducing or enhancing secretion of MIP3α from cells characterized by CXCR4 membrane expression.

In another aspect, the invention is directed to a pharmaceutical composition comprising a compound having CXCR4 agonistic properties, preferably a peptide having an amino acid sequence as set forth in SEQ ID NO:1 or an analog or derivative thereof, for enhancing the immunogenicity of an antigen, for enhancing the immunogenicity of a tumor characterized by CXCR4 membrane expression, and/or for inducing or enhancing secretion of MIP3α from cells characterized by CXCR4 membrane expression.

In another aspect, the invention is directed to the use of a vaccine composition comprising i) an immunogenic amount of an antigen or a nucleic acid construct comprising a nucleic acid sequence encoding the antigen, and ii) an immunogenicity-augmenting amount of a compound having CXCR4 agonistic properties, preferably a peptide having an amino acid sequence as set forth in SEQ ID NO:1 or an analog or derivative thereof, for the preparation of a medicament for stimulating or enhancing an immune response to said antigen and/or for immunizing a subject in need thereof.

In another aspect, the invention is directed to a vaccine composition comprising i) an immunogenic amount of an antigen or a nucleic acid construct comprising a nucleic acid sequence encoding the antigen and ii) an immunogenicity-augmenting amount of a compound having CXCR4 agonistic properties, preferably a peptide having an amino acid sequence as set forth in SEQ ID NO:1 or an analog or derivative thereof, for stimulating or enhancing an immune response to said antigen and/or for immunizing a subject in need thereof.

In various embodiments of the present invention, the subject is selected from humans and non-human mammals. In a preferable embodiment, the subject is human.

For any preparation used in the methods of the invention, the dosage or the therapeutically effective amount can be estimated initially from in vitro and cell culture assays. For example, a dose can be formulated in animal models to achieve a desired concentration or titer. Such information can be used to more accurately determine useful doses in humans. An exemplary dosage range for human use may be from about 1 µg to about 5 mg per kg.

The following examples are presented in order to more fully illustrate some embodiments of the invention. They should, in no way be construed, however, as limiting the broad scope of the invention.

EXAMPLES

Example 1

4F-benzoyl-TN14003 Induces MIP3α Secretion from Prostate Cell Lines in a CXCR4 Agonist Manner In order to study the in vitro and in vivo role of CXCR4 in cancer, a PC3 prostate cell line that overexpresses high levels of CXCR4 was generated. Single cell clones were generated from this PC3-CXCR4 cell line, and one of the clones (PC3-CXCR4.5), which showed Thigh and stable expression level of CXCR4, was selected for the experiments.

FIG. 1A presents FACS histograms of PC3 cells (left panel) and a single cell clone with stable overexpression of CXCR4, GFP and luc genes (PC3-CXCR4.5, right panel) that were stained for the control (IgG2a-PE, full histograms) and CXCR4 (IgG2a-12G5, empty histograms) antibodies.

Figure 1B:
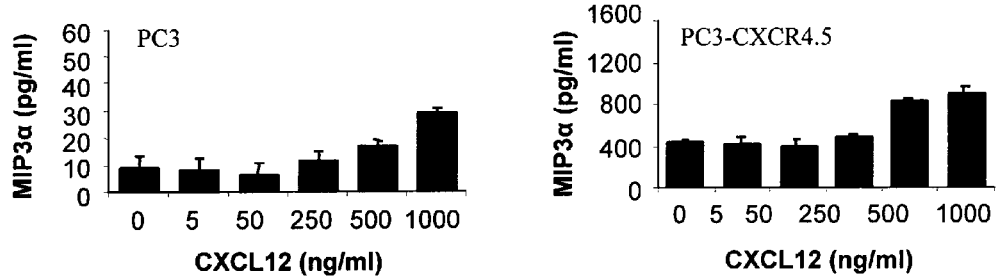
FIG. 1B illustrates MIP3α secretion, assessed by ELISA, of PC3 cells (left panel) and PC3-CXCR4.5 cells (right panel) stimulated with different concentrations of CXCL12 for 48 hours.

In this example, regulation of the chemokine MIP3α (macrophage inflammatory protein 3α) was examined. It was found that PC3-CXCR4.5 cells secreted higher levels of MIP3α than PC3 cells, and increasing doses of CXCL12 increased the secretion of MIP3α in both PC3 and PC3-CXCR4.5 cells (FIG. 1B). In FIG. 1B, PC3 (left panel) and PC3-CXCR4.5 (right panel) cells were stimulated with the indicated concentrations of CXCL12 for 48 hours and MIP3α secretion was assessed by ELISA. The results represent the average of triplicates±STDEV.

Figure 1C:
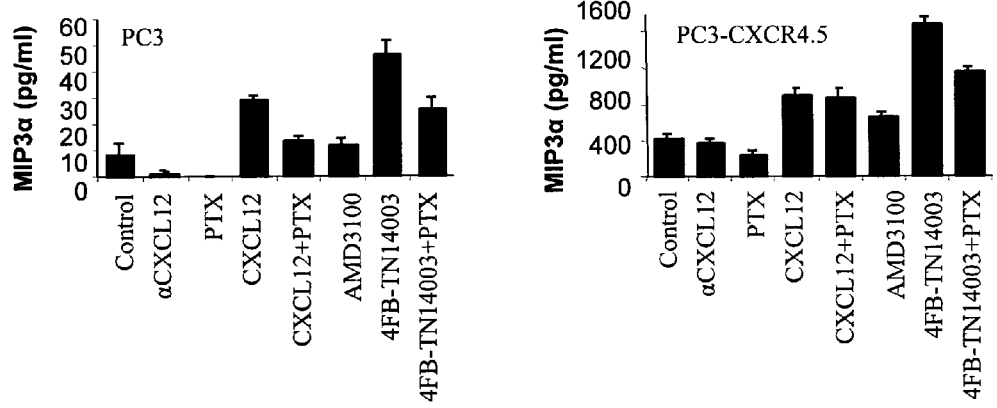
FIG. 1C illustrates MIP3α secretion, assessed by ELISA, of PC3 cells (left panel) and PC3-CXCR4.5 cells (right panel) treated with anti-CXCL12 antibodies, Pertussis toxin, AMD3100 or 4F-benzoyl-TN14003, alone or in combination with CXCL12.

In PC3 cells, treatment with neutralizing antibodies against CXCL12 (αCXCL12) or with Pertussis toxin (PTX; alone or in combination with CXCL12) effectively inhibited the secretion of MIP3α (FIG. 1C). In contrast, in PC3-CXCR4.5 cells, anti-CXCL12 antibodies did not quite affect the secretion level of MIP3α; with PTX treatment alone, secretion of MIP3α was decreased, but PTX in combination with CXCL12 did not demonstrate an inhibitory effect on the level of MIP3α (FIG. 1C). The effects of the CXCR4 antagonist AMD3100 and of 4F-benzoyl-TN14003 (4FB-TN14003), hitherto known as a CXCR4 antagonist, on MIP3α secretion were further tested. Surprisingly, 4F-benzoyl-TN14003, but not AMD3100 induced in both cell lines MIP3α secretion in an agonist manner (FIG. 1C). The effect of 4F-benzoyl-TN14003 was partially inhibited by PTX treatment in both cell lines (FIG. 1C). In FIG. 1C, CXCR4 signaling in PC3 (left panel) and PC3-CXCR4.5 (right panel) cells was inhibited with anti-CXCL12 antibodies (αCXCL12) and Pertussis toxin (PTX) treatments alone or in combination with CXCL12, as indicated. Secretion of MIP3α was assessed by ELISA. The results represent the average of triplicates±STDEV.

Figure 2A:
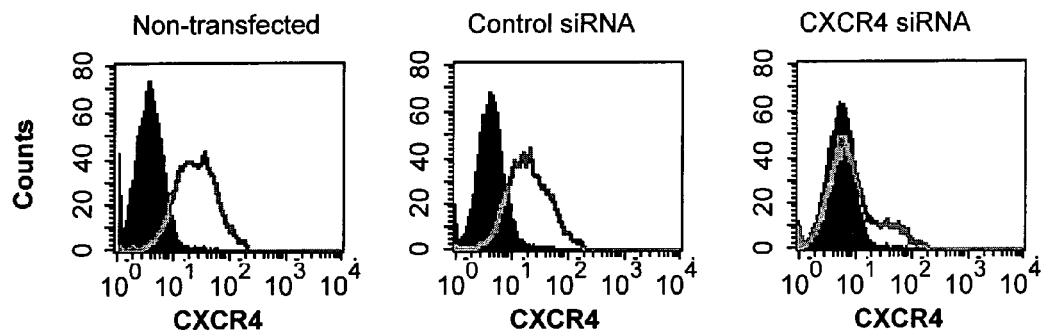
FIG. 2A illustrates FACS analysis of PC3-CXCR4.5 cells 48 hours following the transfection with CXCR4 siRNA, stained for the control and CXCR4 antibodies.
Figure 2B:
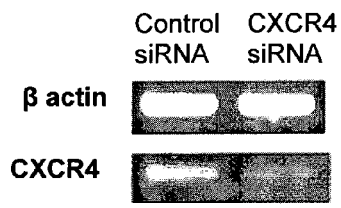
FIG. 2B illustrates RT-PCR analysis of CXCR4 of the siRNA-transfected PC3-CXCR4.5 cells 48 hours following the transfection.
Figure 2C:
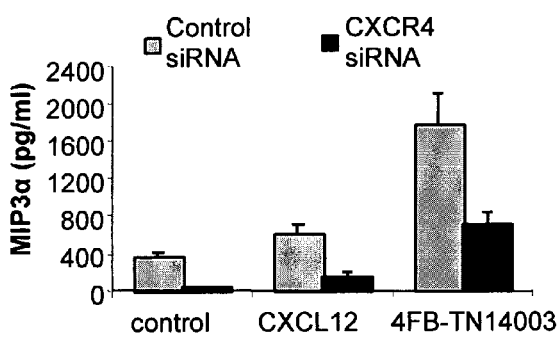
FIG. 2C illustrates MIP3α secretion, assessed by ELISA, of control and CXCR4 siRNA-transfected PC3-CXCR4.5 cells at 48 hours post-transfection incubated with CXCL12 and 4F-benzoyl-TN14003 for an additional 48 hours.

PC3-CXCR4.5 cells secreted higher levels of MIP3α than PC3 cells, and increasing doses of CXCL12 increased the secretion of MIP3α from these cells. Spontaneous secretion of MIP3α is CXCL12 and PTX independent in these cells. In order to find out whether the spontaneous, CXCL12-induced and 4F-benzoyl-TN14003-induced secretion is CXCR4 dependent, the cells were transfected with CXCR4-specific siRNA and tested for CXCR4 and MIP3α expression. It was found, that siRNA specific for CXCR4, but not control siRNA reduced CXCR4 mRNA and cell surface expression (FIGS. 2A and 2B). Silencing of CXCR4 expression inhibited the spontaneous, CXCL12 induced and 4F-benzoyl-TN14003 induced secretion of MIP3α by PC3-CXCR4.5 cells (FIG. 2C). These results strongly suggest that 4F-benzoyl-TN14003 induced secretion of MIP3α is mediated by CXCR4 and that 4F-benzoyl-TN14003 act as a super agonist for CXCR4.

The Dicer-substrate siRNA duplexes of CXCR4 (NCBI accession number NM 003467): sense 5'-UAAAAUCUUC-CUGCCCACCAUCUAC-3' (SEQ ID NO:78), antisense 5' GUAGAUGGUGGGCAGGAAGAUUUUAUU-3' (SEQ ID NO:79) were purchased from IDT, Coralville, Iowa. The non-specific siRNA duplexes were used as a control. PC3-CXCR4.5 cells were transfected with 200 nmol/L siRNA in serum-free medium using Oligofectamine reagent (Invitrogen, Carlsbad, Calif., USA), according to the manufacturer's instructions. To determine the efficiency of CXCR4RNA interference, at 48 hours post-transfection, the cells were analyzed for CXCR4 expression on mRNA and cell-surface levels.

In FIG. 2A, PC3-CXCR4.5 cells 48 hours following the transfection with CXCR4-specific siRNA were stained for the control and CXCR4 antibodies and evaluated by FACS. Left panel, non-transfected cells; middle panel, cells transfected with a control (non-specific) siRNA; right panel, cells transfected with a siRNA directed to CXCR4 (CXCR4 siRNA). Cells were stained for the control (IgG2a-PE, full histograms) and CXCR4 antibodies (IgG2a-12G5, empty histograms).

In FIG. 2B, RT-PCR analysis of CXCR4 of the siRNA-transfected PC3-CXCR4.5 cells 48 hours following the transfection is presented. Left, cells transfected with a control (non-specific) siRNA; right, cells transfected with a siRNA directed to CXCR4. Gene expression was determined using primers specific to CXCR4, or to the housekeeping gene β-actin as a control.

The following primer pairs were used for PCR: β-actin sense 5'-CCCTGGACTTCGAGCAAGAG'-3' (SEQ ID NO: 80), antisense 5'-TCTCCTTCTGCATCCTGTCG-3' (SEQ ID NO: 81);
CCL20 sense 5' ATGTGCTGTACCAAGAGTTT-3' (SEQ ID NO: 82), antisense 5'-CAAGTCTGTTTTGGATTTGC-3' (SEQ ID NO: 83);
CCR6 sense 5' CCATTCTGGGCAGTGAGTCA-3' (SEQ ID NO: 84), antisense 5'-AGCAGCATCCCGCAGTTAA-3' (SEQ ID NO: 85);

CXCR4 sense 5'-AGCTGTTGGCTGAAAAGGTGGTC-TATG-3' (SEQ ID NO: 86), antisense 5'-GCGCTTCTG-GTGGCCCTTGGAGTGTG-3' (SEQ ID NO: 87);

CXCL12 sense 5'-ATGAACGCCAAGGTCGTGGTCG-3' (SEQ ID NO: 88), antisense 5'-TGTTGTTGTTCT-TCAGCCG-3' (SEQ ID NO: 89).

Two microliters of the reverse-transcribed product were subjected to PCR amplification in a final reaction volume of 20 µL containing 1 U of Supertherm Taq polymerase (JMR-Holdings, London, England). Amplification conditions were denaturation at 94° C. for 30 seconds, annealing at 56° C. for 30 seconds, and extension at 72° C. for 30 seconds for 30 consecutive cycles. The PCR amplified products were run on 1% agarose gel containing ethidium bromide. The sizes were estimated by comparison with molecular weight markers.

In FIG. 2C, control (gray) and CXCR4 (black) siRNA-transfected PC3-CXCR4.5 cells at 48 hours post-transfection were incubated with CXCL12 500 ng/ml and 4F-benzoyl-TN14003 8 µM (4FB-TN14003) for additional 48 hours. MIP3α secretion was assessed by ELISA. The results represent the average of triplicates±STDEV.

Example 2

The Chemokine MIP3α is Expressed by Prostate Xenografts that Express CXCR4 and by Primary Human Prostate Cancer Biopsies.

Next, the expression of MIP3α was assessed by immuno-histochemical staining in tumor xenografts produced by PC3LG cells (which express luciferase and GFP genes, but not CXCR4) and PC3-CXCR4 cells, and in primary human prostate cancer biopsies. It was found, that PC3-CXCR4 (FIG. 3, middle panels), but not PC3LG (FIG. 3, left panels) xenografts expressed immnuodetectable levels of MIP3α.

Figure 3:
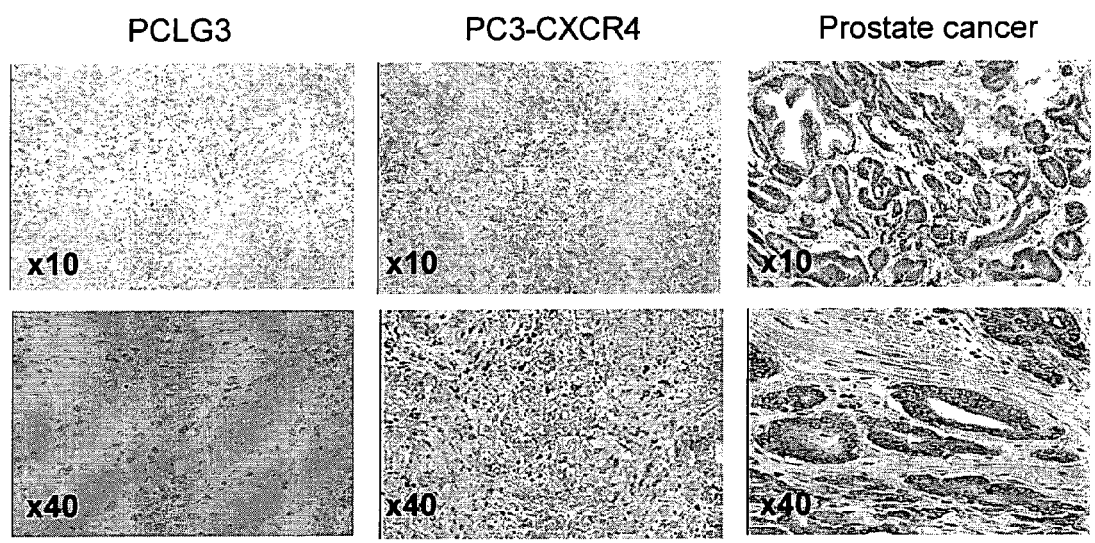
FIG. 3 demonstrates that MIP3α is expressed in vivo by primary human prostate tumors and xenografts overexpressing CXCR4, but not by xenografts with low CXCR4 expression. Immunohistochemical staining of human MIP3α was performed using a monoclonal antibody. Left panels represent staining of xenografts produced by PC3LG cells (top—×10 magnification; bottom—×40 magnification). Middle panels represent staining of xenografts produced by PC3-CXCR4 cells (top—×10 magnification; bottom—×40 magnification). Right panels represent human prostate cancer biopsy (top—×10 magnification; bottom—×40 magnification).

FIG. 3, upper left and lower left panels represent staining of xenografts produced by PC3LG cells in NOD/SCID mice, magnification of ×10 and ×40, respectively. FIG. 3, upper middle and lower middle panels represent staining of xenografts produced by PC3-CXCR4 cells in NOD/SCID mice, magnification of ×10 and ×40, respectively. FIG. 3, upper right and lower right panels represent human prostate cancer biopsy, magnification of ×10 and ×40, respectively.

Immunohistochemical staining for MIP3α was further performed using prostate cancer biopsies and tissue arrays. Out of 55 samples of prostate cancer biopsies tested, six prostate cancer biopsies (10.9%) expressed MIP3α. None of the normal prostate biopsies were stained for MIP3α. Table 2 hereinbelow summarizes the results of MIP3α immunostaining of a prostate cancer tissue array containing 55 samples of prostate cancer and 3 samples of normal prostate tissue.

TABLE 2

MIP3α staining in prostate tissue

| | |
|---|---|
| MIP3α-positive tumors | 6/55 (10.9%) |
| Highly positive | 3/6 (5.4% from total) |
| Stage | 4 tumors - stage IV |
| | 1 tumor - stage III |
| | 1 tumor - stage II |
| Normal prostate | 0/3 |

Example 3

The Chemokine MIP3α is Expressed by the Hepatic Carcinoma Cell Line HepG2, by Normal Human Keratinocytes and by Human Leukemic Cell Lines NB4 and HL-60 and its Levels are Upregulated by CXCL12 and 4F-benzoyl-TN14003

Figure 4A:
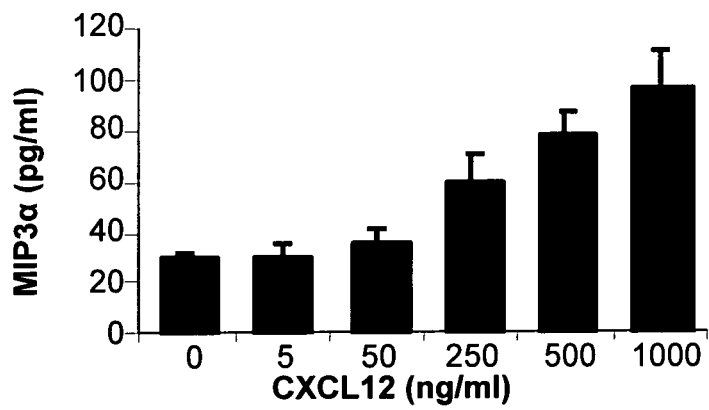
FIG. 4 demonstrates that CXCR4 activation by CXCL12 enhances the MIP3α secretion from human leukemic cells and normal keratinocytes. Acute promyelocytic leukemia cell lines NB4 (FIG. 4A) and HL60 (FIG. 4B), primary peripheral blasts from the patient with acute myelocytic leukemia (FIG. 4C) and normal keratinocytes (FIG. 4D) were stimulated with different concentration of CXCL12 for 48 hours. The secretion of MIP3α was assayed by ELISA.
Figure 4B:
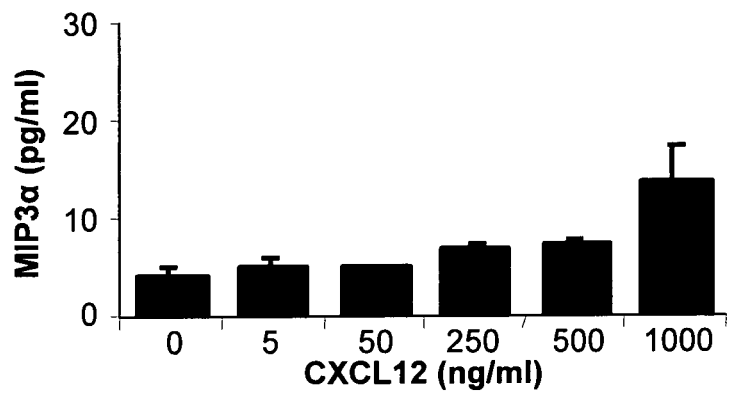
Figure 4C:
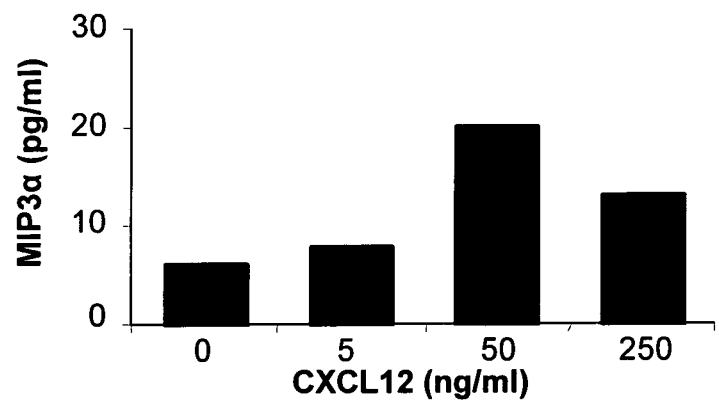
Figure 4D:
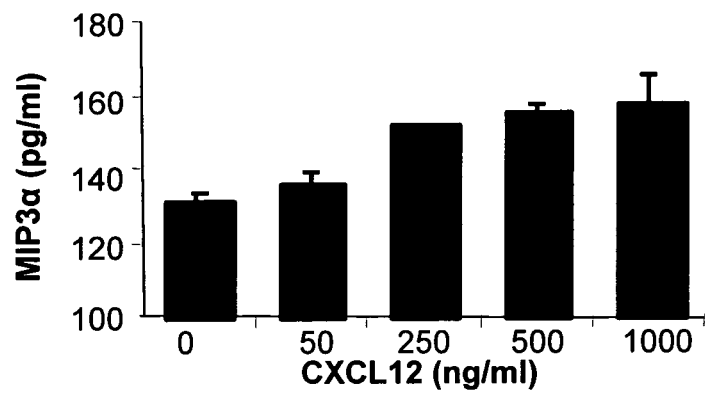

The expression of MIP3α in a range of carcinoma cell lines and normal epithelial cells was tested by ELISA. The prostate cancer cell lines, DU145, LNCap, 22Rv1 and 22Rv1-CXCR4, did not express MIP3α. Bone marrow endothelial cells, BMEC, glioblastoma cells U87, breast carcinoma cells MDA231, also were negative for MIP3α secretion. The acute promyelocytic leukemia (APL) cell lines, NB4 and HL-60, secreted MIP3α (FIGS. 4A and 4B, respectively). In addition, MIP3α was also secreted by normal keratinocytes (FIG. 4D) and primary blasts from peripheral blood of patients with AML (FIG. 4C).

Furthermore, in HL-60, NB4 and keratinocytes, the secretion of MIP3α was increased following the stimulation with CXCL12 and 4F-benzoyl-TN14003 (FIGS. 5 and 6).

Figure 5A:
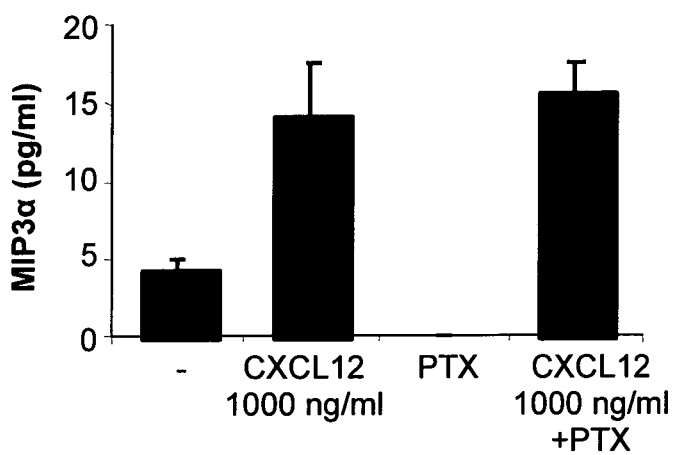
FIG. 5 demonstrates that CXCR4 activation by CXCL12 enhances MIP3α secretion from human leukemic cells and normal keratinocytes in a CXCR4-specific manner. CXCR4 signaling in HL60 (FIG. 5A) and keratinocytes (FIG. 5B) was inhibited with Pertussis toxin treatment alone or in combination with CXCL12. Secretion of MIP3α was assessed by ELISA.
Figure 5B:
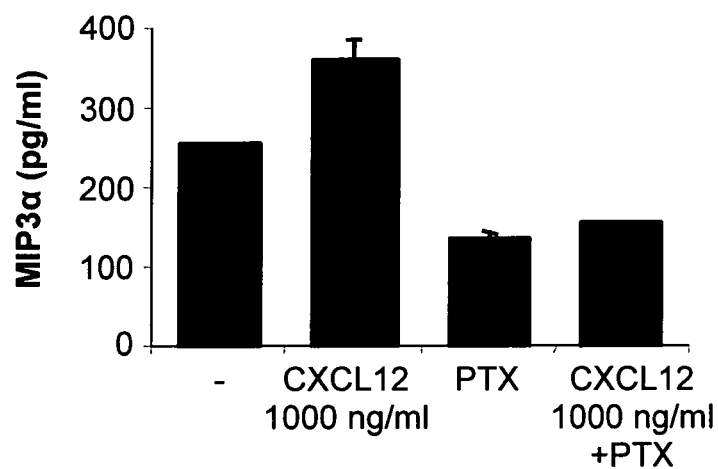
Figure 6A:
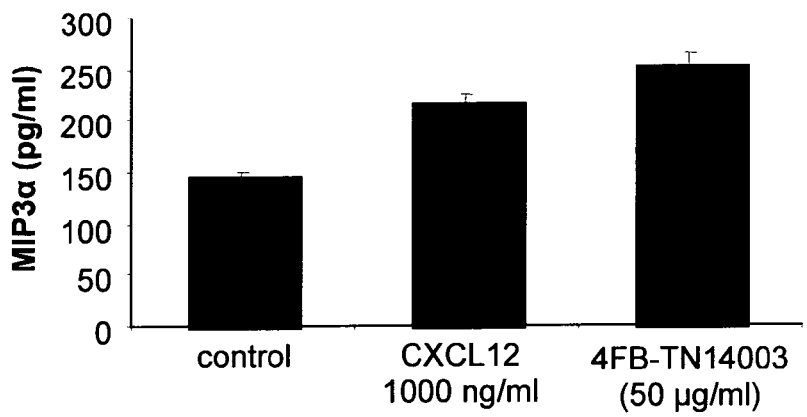
FIG. 6 demonstrates that CXCR4 activation by CXCL12 or 4F-benzoyl-TN14003 enhances the MIP3α secretion from human leukemic cells and normal keratinocytes. 4F-benzoyl-TN14003 (4FB-TN14003) stimulates HL60 and NB4 to secrete MIP3α.
Figure 6B:
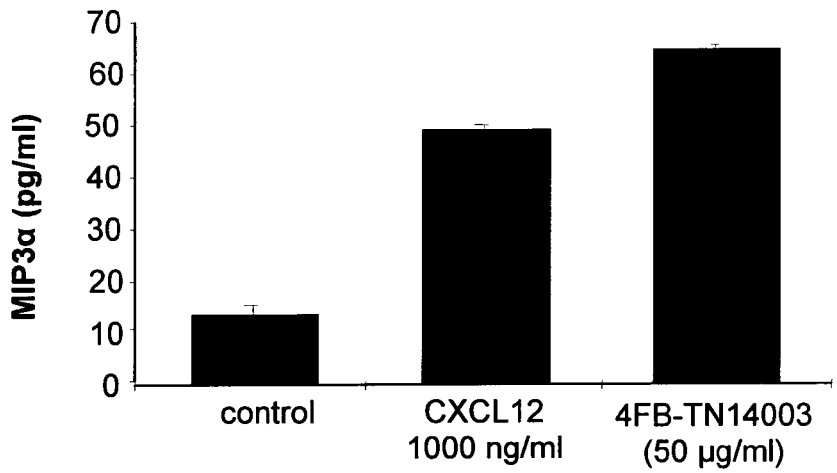
Figure 6C:
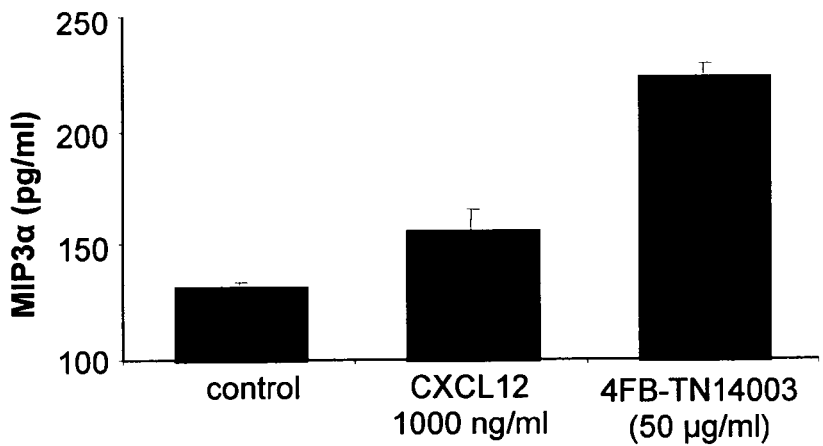

In FIG. 4, acute promyelocytic leukemia cell lines NB4 (FIG. 4A) and HL60 (FIG. 4B), primary peripheral blasts from the patient with acute myelocytic leukemia (FIG. 4C) and normal keratinocytes (FIG. 4D) were stimulated with the indicated concentration of CXCL12 for 48 hours. The secretion of MIP3α was assayed by ELISA. The results of experiments with NB4, HL60 and keratinocytes represent the average of triplicates±STDEV. In FIG. 5, CXCR4 signaling in HL60 (FIG. 5A) and keratinocytes (FIG. 5B) was inhibited with Pertussis toxin (PTX) treatment alone or in combination with CXCL12. Secretion of MIP3α was assessed by ELISA. FIG. 6 demonstrates that 4F-benzoyl-TN14003 (4FB-TN14003) stimulates NB4 (FIG. 6A), HL60 (FIG. 6B) and keratinocytes (FIG. 6C) to secrete MIP3α. The results represent the average of triplicates±STDEV.

REFERENCES

Avniel, S. et al., *J. Invest. Dermatol.* 2006, 126(2): 468-76.
Balkwill, F. *Semi. in Canc. Biol.* 2004, 14: 171-179.
Broxmeyer, H. E. et al., *J. Exp. Med.* 2005, 201(8): 1307-1318.
Dar, A. et al., *Nat. Immunol.* 2005. 6(10): 1038-1046.
Flomenberg, N. et al., *Blood,* 2005, 106(5): 1867-1874.
Kim, C. H. and Broxmeyer H. E., *Blood,* 1998, 91(1): 100-110.
Kollet, O. et al., *Blood,* 2002, 100(8): 2778-2786.
Lack, N. A. et al., *Clin. Pharmacol. Ther.* 2005, 77(5): 427-436.
Lapidot, T. and Kollet, O., *Leukemia,* 2002 16(10): 1992-2003.
Lapidot, T. et al., *Blood,* 2005, 106(6): 1901-1910.
Levesque, J. P. et al., *J. Clin. Invest.* 2003, 111(2): 187-196.
Martin, C. et al., *Immunity,* 2003, 19(4): 583-593.
Muller, A. et al., *Nature,* 2001, 410: 50-56.
Nagasawa, T. et al., *Proc. Nat. Aca. Sci.* 1994, 91: 2305-2309.
Peled, A., et al., *Science,* 1999, 283(5403): 845-848.
Phillips, R. et al., *Amer. J. Respir. Critic. Care Med.* 2003, 167: 1676-1686.
Princen, K. and Schols, D., *Cytokine Grow. Fac. Rev.* 2005, 16(6): 659-677.
Rossi, D. and Zlotnik, A., *Ann. Rev. Immun.* 2000, 18: 217-242.
Tamamura, H. et al., *Biochem. Biophys. Res. Commun.* 1998, 253(3): 877-882.

Tamamura, H. et al., *Org. Biomol. Chem.* 2003, 1: 3663-3669.
Tamamura, H. and Fujii, N., *Expert Opin. Ther. Targets,* 2005, 9(6): 1267-1282.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

SEQUENCE LISTING

```
<160> NUMBER OF SEQ ID NOS: 89

<210> SEQ ID NO 1
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 4-fluorobenzoyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 1

Xaa Arg Xaa Cys Tyr Xaa Lys Xaa Pro Tyr Arg Xaa Cys Arg
1               5                   10

<210> SEQ ID NO 2
<211> LENGTH: 14
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: MOD_RES
<222> LOCATION: (1)..(1)
<223> OTHER INFORMATION: N' ACETYLATION
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline
```

-continued

```
<400> SEQUENCE: 2

Arg Arg Xaa Cys Tyr Xaa Lys Xaa Pro Tyr Arg Xaa Cys Arg
1               5                   10

<210> SEQ ID NO 3
<211> LENGTH: 14
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: MOD_RES
<222> LOCATION: (1)..(1)
<223> OTHER INFORMATION: N' ACETYLATION
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline

<400> SEQUENCE: 3

Arg Arg Xaa Cys Tyr Arg Lys Xaa Pro Tyr Arg Xaa Cys Arg
1               5                   10

<210> SEQ ID NO 4
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline

<400> SEQUENCE: 4

Arg Arg Xaa Cys Tyr Xaa Lys Xaa Pro Tyr Arg Xaa Cys Arg
1               5                   10

<210> SEQ ID NO 5
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
```

```
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (11)..(12)
<223> OTHER INFORMATION: citrulline

<400> SEQUENCE: 5

Arg Arg Xaa Cys Tyr Xaa Lys Xaa Pro Tyr Xaa Xaa Cys Arg
1               5                   10

<210> SEQ ID NO 6
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' acetylated citrulline
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 6

Xaa Arg Xaa Cys Tyr Xaa Lys Xaa Pro Tyr Arg Xaa Cys Arg
1               5                   10

<210> SEQ ID NO 7
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' acetylated citrulline
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline

<400> SEQUENCE: 7

Xaa Arg Xaa Cys Tyr Arg Lys Xaa Pro Tyr Arg Xaa Cys Arg
```

```
1               5                   10
```

<210> SEQ ID NO 8
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (11)..(12)
<223> OTHER INFORMATION: citrulline

<400> SEQUENCE: 8

```
Arg Arg Xaa Cys Tyr Arg Lys Xaa Pro Tyr Xaa Xaa Cys Arg
1               5                   10
```

<210> SEQ ID NO 9
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED citrulline
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (11)..(12)
<223> OTHER INFORMATION: citrulline

<400> SEQUENCE: 9

```
Xaa Arg Xaa Cys Tyr Arg Lys Xaa Pro Tyr Xaa Xaa Cys Arg
1               5                   10
```

<210> SEQ ID NO 10
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:

```
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 10

Arg Arg Xaa Cys Tyr Xaa Lys Xaa Pro Tyr Arg Xaa Cys Arg
1               5                   10

<210> SEQ ID NO 11
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (11)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 11

Arg Arg Xaa Cys Tyr Xaa Lys Xaa Pro Tyr Xaa Xaa Cys Arg
1               5                   10

<210> SEQ ID NO 12
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED citrulline
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
```

-continued

```
<223> OTHER INFORMATION: citrulline
<220> FEATURE:
<221> NAME/KEY: MOD_RES
<222> LOCATION: (14)..(14)
<223> OTHER INFORMATION: AMIDATED

<400> SEQUENCE: 12

Xaa Arg Xaa Cys Tyr Xaa Lys Xaa Pro Tyr Arg Xaa Cys Arg
1               5                   10

<210> SEQ ID NO 13
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED citrulline
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 13

Xaa Arg Xaa Cys Tyr Arg Lys Xaa Pro Tyr Arg Xaa Cys Arg
1               5                   10

<210> SEQ ID NO 14
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (11)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 14

Arg Arg Xaa Cys Tyr Arg Lys Xaa Pro Tyr Xaa Xaa Cys Arg
1               5                   10

<210> SEQ ID NO 15
<211> LENGTH: 14
```

```
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED citrulline
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (11)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 15

Xaa Arg Xaa Cys Tyr Arg Lys Xaa Pro Tyr Xaa Xaa Cys Arg
1               5                   10

<210> SEQ ID NO 16
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: D-glutamic acid
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 16

Xaa Arg Xaa Cys Tyr Arg Lys Xaa Pro Tyr Arg Xaa Cys Arg
1               5                   10

<210> SEQ ID NO 17
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 17
```

Arg Glu Xaa Cys Tyr Arg Lys Xaa Pro Tyr Arg Xaa Cys Arg
1               5                   10

<210> SEQ ID NO 18
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 18

Arg Arg Xaa Cys Tyr Glu Lys Xaa Pro Tyr Arg Xaa Cys Arg
1               5                   10

<210> SEQ ID NO 19
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 19

Arg Arg Xaa Cys Tyr Arg Glu Xaa Pro Tyr Arg Xaa Cys Arg
1               5                   10

<210> SEQ ID NO 20
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline

<400> SEQUENCE: 20

Arg Arg Xaa Cys Tyr Arg Lys Xaa Pro Tyr Arg Xaa Cys Arg
1               5                   10

```
<210> SEQ ID NO 21
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 21

Arg Arg Xaa Cys Tyr Arg Lys Xaa Pro Tyr Glu Xaa Cys Arg
 1               5                  10

<210> SEQ ID NO 22
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 22

Arg Arg Xaa Cys Tyr Arg Lys Xaa Pro Tyr Arg Xaa Cys Glu
 1               5                  10

<210> SEQ ID NO 23
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' amidated

<400> SEQUENCE: 23

Arg Arg Xaa Cys Tyr Xaa Lys Xaa Pro Tyr Arg Xaa Cys Arg
```

<210> SEQ ID NO 24
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: D-glutamic acid
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 24

Arg Arg Xaa Cys Tyr Xaa Lys Xaa Pro Tyr Arg Xaa Cys Arg
1               5                   10

<210> SEQ ID NO 25
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: D-glutamic acid
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 25

Arg Arg Xaa Cys Tyr Xaa Lys Xaa Pro Tyr Arg Xaa Cys Arg
1               5                   10

<210> SEQ ID NO 26
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: D-glutamic acid
<220> FEATURE:

```
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 26

Xaa Arg Xaa Cys Tyr Xaa Lys Xaa Pro Tyr Arg Xaa Cys Arg
 1               5                  10

<210> SEQ ID NO 27
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (10)..(10)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 27

Arg Arg Xaa Cys Tyr Xaa Lys Xaa Pro Xaa Arg Xaa Cys Arg
 1               5                  10

<210> SEQ ID NO 28
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
```

-continued

```
<223> OTHER INFORMATION: D-glutamic acid
<220> FEATURE:
<221> NAME/KEY: MOD_RES
<222> LOCATION: (12)..(12)
<223> OTHER INFORMATION: D-glutamic acid
<220> FEATURE:
<221> NAME/KEY: MOD_RES
<222> LOCATION: (14)..(14)
<223> OTHER INFORMATION: c' amidated

<400> SEQUENCE: 28

Arg Arg Xaa Cys Tyr Xaa Lys Xaa Pro Tyr Arg Xaa Cys Arg
1               5                   10

<210> SEQ ID NO 29
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED D-glutamic acid
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 29

Xaa Arg Xaa Cys Tyr Xaa Lys Xaa Pro Tyr Arg Xaa Cys Arg
1               5                   10

<210> SEQ ID NO 30
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (10)..(10)
<223> OTHER INFORMATION: D-glutamic acid
<220> FEATURE:
```

```
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 30

Arg Arg Xaa Cys Tyr Xaa Lys Xaa Pro Xaa Arg Xaa Cys Arg
1               5                   10

<210> SEQ ID NO 31
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: D-glutamic acid
<220> FEATURE:
<221> NAME/KEY: MOD_RES
<222> LOCATION: (14)..(14)
<223> OTHER INFORMATION: c' amidated

<400> SEQUENCE: 31

Arg Arg Xaa Cys Tyr Xaa Lys Xaa Pro Tyr Arg Xaa Cys Arg
1               5                   10

<210> SEQ ID NO 32
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
```

```
<223> OTHER INFORMATION: c' amidated

<400> SEQUENCE: 32

Arg Arg Xaa Cys Tyr Xaa Lys Xaa Pro Tyr Arg Xaa Cys Arg
1               5                   10

<210> SEQ ID NO 33
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Guanyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 33

Xaa Arg Xaa Cys Tyr Xaa Lys Xaa Pro Tyr Arg Xaa Cys Arg
1               5                   10

<210> SEQ ID NO 34
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Tetramethylguanyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 34

Xaa Arg Xaa Cys Tyr Xaa Lys Xaa Pro Tyr Arg Xaa Cys Arg
1               5                   10
```

```
<210> SEQ ID NO 35
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Tetramethylguanyl-arginine
<220> FEATURE:
<221> NAME/KEY: MOD_RES
<222> LOCATION: (2)..(2)
<223> OTHER INFORMATION: 3-((2-naphthyl) alanine
<220> FEATURE:
<221> NAME/KEY: MOD_RES
<222> LOCATION: (5)..(5)
<223> OTHER INFORMATION: citrulline
<220> FEATURE:
<221> NAME/KEY: MOD_RES
<222> LOCATION: (7)..(7)
<223> OTHER INFORMATION: D-glutamic acid
<220> FEATURE:
<221> NAME/KEY: MOD_RES
<222> LOCATION: (11)..(11)
<223> OTHER INFORMATION: citrulline
<220> FEATURE:
<221> NAME/KEY: MOD_RES
<222> LOCATION: (13)..(13)
<223> OTHER INFORMATION: c' amidated

<400> SEQUENCE: 35

Xaa Xaa Cys Tyr Xaa Lys Xaa Pro Tyr Arg Xaa Cys Arg
1               5                   10

<210> SEQ ID NO 36
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 4-fluorobenzoyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: amidated

<400> SEQUENCE: 36

Xaa Arg Xaa Cys Tyr Xaa Lys Xaa Pro Tyr Arg Xaa Cys Arg
1               5                   10

<210> SEQ ID NO 37
<211> LENGTH: 14
<212> TYPE: PRT
<213> ORGANISM: Artificial Sequence
```

```
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 2-fluorobenzoyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 37

Xaa Arg Xaa Cys Tyr Xaa Lys Xaa Pro Tyr Arg Xaa Cys Arg
1               5                   10

<210> SEQ ID NO 38
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 5-aminopentanoyl-arginine
<220> FEATURE:
<221> NAME/KEY: MOD_RES
<222> LOCATION: (2)..(2)
<223> OTHER INFORMATION: 3-((2-naphthyl) alanine
<220> FEATURE:
<221> NAME/KEY: MOD_RES
<222> LOCATION: (5)..(5)
<223> OTHER INFORMATION: citrulline
<220> FEATURE:
<221> NAME/KEY: MOD_RES
<222> LOCATION: (7)..(7)
<223> OTHER INFORMATION: D-glutamic acid
<220> FEATURE:
<221> NAME/KEY: MOD_RES
<222> LOCATION: (11)..(11)
<223> OTHER INFORMATION: citrulline
<220> FEATURE:
<221> NAME/KEY: MOD_RES
<222> LOCATION: (13)..(13)
<223> OTHER INFORMATION: c' amidated

<400> SEQUENCE: 38

Xaa Xaa Cys Tyr Xaa Lys Xaa Pro Tyr Arg Xaa Cys Arg
1               5                   10

<210> SEQ ID NO 39
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 2-desamino-arginyl
```

```
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 39

Xaa Arg Xaa Cys Tyr Xaa Lys Xaa Pro Tyr Arg Xaa Cys Arg
1               5                   10

<210> SEQ ID NO 40
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Guanyl-arginine
<220> FEATURE:
<221> NAME/KEY: MOD_RES
<222> LOCATION: (2)..(2)
<223> OTHER INFORMATION: 3-((2-naphthyl) alanine
<220> FEATURE:
<221> NAME/KEY: MOD_RES
<222> LOCATION: (5)..(5)
<223> OTHER INFORMATION: citrulline
<220> FEATURE:
<221> NAME/KEY: MOD_RES
<222> LOCATION: (7)..(7)
<223> OTHER INFORMATION: D-glutamic acid
<220> FEATURE:
<221> NAME/KEY: MOD_RES
<222> LOCATION: (11)..(11)
<223> OTHER INFORMATION: citrulline
<220> FEATURE:
<221> NAME/KEY: MOD_RES
<222> LOCATION: (13)..(13)
<223> OTHER INFORMATION: c' amidated

<400> SEQUENCE: 40

Xaa Xaa Cys Tyr Xaa Lys Xaa Pro Tyr Arg Xaa Cys Arg
1               5                   10

<210> SEQ ID NO 41
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Succinyl-arginine
<220> FEATURE:
<221> NAME/KEY: MOD_RES
<222> LOCATION: (2)..(2)
<223> OTHER INFORMATION: 3-((2-naphthyl) alanine
<220> FEATURE:
<221> NAME/KEY: MOD_RES
```

```
<222> LOCATION: (5)..(5)
<223> OTHER INFORMATION: citrulline
<220> FEATURE:
<221> NAME/KEY: MOD_RES
<222> LOCATION: (7)..(7)
<223> OTHER INFORMATION: D-glutamic acid
<220> FEATURE:
<221> NAME/KEY: MOD_RES
<222> LOCATION: (11)..(11)
<223> OTHER INFORMATION: citrulline
<220> FEATURE:
<221> NAME/KEY: MOD_RES
<222> LOCATION: (13)..(13)
<223> OTHER INFORMATION: c' amidated

<400> SEQUENCE: 41

Xaa Xaa Cys Tyr Xaa Lys Xaa Pro Tyr Arg Xaa Cys Arg
1               5                   10

<210> SEQ ID NO 42
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Glutaryl-arginine
<220> FEATURE:
<221> NAME/KEY: MOD_RES
<222> LOCATION: (2)..(2)
<223> OTHER INFORMATION: 3-((2-naphthyl) alanine
<220> FEATURE:
<221> NAME/KEY: MOD_RES
<222> LOCATION: (5)..(5)
<223> OTHER INFORMATION: citrulline
<220> FEATURE:
<221> NAME/KEY: MOD_RES
<222> LOCATION: (7)..(7)
<223> OTHER INFORMATION: D-glutamic acid
<220> FEATURE:
<221> NAME/KEY: MOD_RES
<222> LOCATION: (11)..(11)
<223> OTHER INFORMATION: citrulline
<220> FEATURE:
<221> NAME/KEY: MOD_RES
<222> LOCATION: (13)..(13)
<223> OTHER INFORMATION: c' amidated

<400> SEQUENCE: 42

Xaa Xaa Cys Tyr Xaa Lys Xaa Pro Tyr Arg Xaa Cys Arg
1               5                   10

<210> SEQ ID NO 43
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: desaminoTMG-APA (formula IV in the
      specification)
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
```

```
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 43

Xaa Arg Xaa Cys Tyr Xaa Lys Xaa Pro Tyr Arg Xaa Cys Arg
1               5                   10

<210> SEQ ID NO 44
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: R-CH2 - formula (V) in the specification
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 44

Xaa Arg Xaa Cys Tyr Xaa Lys Xaa Pro Tyr Arg Xaa Cys Arg
1               5                   10

<210> SEQ ID NO 45
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: 3-((2-naphthyl) alanine
<220> FEATURE:
<221> NAME/KEY: MOD_RES
<222> LOCATION: (5)..(5)
<223> OTHER INFORMATION: citrulline
<220> FEATURE:
<221> NAME/KEY: MOD_RES
<222> LOCATION: (7)..(7)
<223> OTHER INFORMATION: D-glutamic acid
<220> FEATURE:
<221> NAME/KEY: MOD_RES
<222> LOCATION: (11)..(11)
<223> OTHER INFORMATION: citrulline
<220> FEATURE:
<221> NAME/KEY: MOD_RES
<222> LOCATION: (13)..(13)
<223> OTHER INFORMATION: c' amidated
```

```
<400> SEQUENCE: 45

Arg Xaa Cys Tyr Xaa Lys Xaa Pro Tyr Arg Xaa Cys Arg
1               5                   10

<210> SEQ ID NO 46
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: tetramethylguanyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 46

Xaa Arg Xaa Cys Tyr Xaa Lys Xaa Pro Tyr Arg Xaa Cys Arg
1               5                   10

<210> SEQ ID NO 47
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 6-aminohexanoyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 47

Xaa Arg Xaa Cys Tyr Xaa Lys Xaa Pro Tyr Arg Xaa Cys Arg
1               5                   10
```

```
<210> SEQ ID NO 48
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 6-aminohexanoyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 48

Xaa Arg Xaa Cys Tyr Arg Lys Xaa Pro Tyr Arg Xaa Cys Arg
1               5                   10

<210> SEQ ID NO 49
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' amidated

<400> SEQUENCE: 49

Arg Arg Xaa Cys Tyr Xaa Arg Xaa Pro Tyr Arg Xaa Cys Arg
1               5                   10

<210> SEQ ID NO 50
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
```

```
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' amidated

<400> SEQUENCE: 50

Arg Arg Xaa Cys Tyr Xaa Arg Xaa Pro Tyr Arg Xaa Cys Arg
1               5                   10

<210> SEQ ID NO 51
<211> LENGTH: 14
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 51

Arg Arg Xaa Cys Tyr Xaa Lys Xaa Pro Tyr Arg Xaa Cys Arg
1               5                   10

<210> SEQ ID NO 52
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
```

<222> LOCATION: (14)..(14)
<223> OTHER INFORMATION: C' AMIDATED

<400> SEQUENCE: 52

Arg Arg Xaa Cys Tyr Arg Lys Xaa Pro Tyr Arg Xaa Cys Arg
1               5                   10

<210> SEQ ID NO 53
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 4-fluorobenzoyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MISC_FEATURE
<222> LOCATION: (14)..(14)
<223> OTHER INFORMATION: derivatization by a NH-methyl group

<400> SEQUENCE: 53

Xaa Arg Xaa Cys Tyr Xaa Lys Xaa Pro Tyr Arg Xaa Cys Arg
1               5                   10

<210> SEQ ID NO 54
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 4-fluorobenzoyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MISC_FEATURE
<222> LOCATION: (14)..(14)
<223> OTHER INFORMATION: derivatization by a NH-ethyl group

<400> SEQUENCE: 54

Xaa Arg Xaa Cys Tyr Xaa Lys Xaa Pro Tyr Arg Xaa Cys Arg

```
1               5                   10
```

<210> SEQ ID NO 55
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 4-fluorobenzoyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MISC_FEATURE
<222> LOCATION: (14)..(14)
<223> OTHER INFORMATION: derivatization by NH-isopropyl

<400> SEQUENCE: 55

```
Xaa Arg Xaa Cys Tyr Xaa Lys Xaa Pro Tyr Arg Xaa Cys Arg
1               5                   10
```

<210> SEQ ID NO 56
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 4-fluorobenzoyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MISC_FEATURE
<222> LOCATION: (14)..(14)
<223> OTHER INFORMATION: derivatization with a tyramine residue

<400> SEQUENCE: 56

```
Xaa Arg Xaa Cys Tyr Xaa Lys Xaa Pro Tyr Arg Xaa Cys Arg
1               5                   10
```

<210> SEQ ID NO 57
<211> LENGTH: 14
<212> TYPE: PRT

```
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 57

Ala Arg Xaa Cys Tyr Arg Lys Xaa Pro Tyr Arg Xaa Cys Arg
1               5                   10

<210> SEQ ID NO 58
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 58

Arg Arg Xaa Cys Tyr Ala Lys Xaa Pro Tyr Arg Xaa Cys Arg
1               5                   10

<210> SEQ ID NO 59
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 59

Arg Arg Xaa Cys Tyr Arg Ala Xaa Pro Tyr Arg Xaa Cys Arg
1               5                   10

<210> SEQ ID NO 60
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
```

```
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-alanine
<220> FEATURE:
<221> NAME/KEY: MOD_RES
<222> LOCATION: (12)..(12)
<223> OTHER INFORMATION: citrulline

<400> SEQUENCE: 60

Arg Arg Xaa Cys Tyr Arg Lys Xaa Pro Tyr Arg Xaa Cys Arg
1               5                   10

<210> SEQ ID NO 61
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 61

Arg Arg Xaa Cys Tyr Arg Lys Xaa Ala Tyr Arg Xaa Cys Arg
1               5                   10

<210> SEQ ID NO 62
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 62

Arg Arg Xaa Cys Tyr Arg Lys Xaa Pro Ala Arg Xaa Cys Arg
1               5                   10

<210> SEQ ID NO 63
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
```

<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 63

Arg Arg Xaa Cys Tyr Arg Lys Xaa Pro Tyr Ala Xaa Cys Arg
1               5                   10

<210> SEQ ID NO 64
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: citrulline
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 64

Xaa Arg Xaa Cys Tyr Arg Lys Xaa Pro Tyr Arg Xaa Cys Arg
1               5                   10

<210> SEQ ID NO 65
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 65

Arg Arg Xaa Cys Tyr Xaa Lys Xaa Pro Tyr Arg Xaa Cys Arg
1               5                   10

<210> SEQ ID NO 66
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine

```
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 66

Arg Arg Xaa Cys Tyr Xaa Lys Xaa Pro Tyr Arg Xaa Cys Arg
1               5                   10

<210> SEQ ID NO 67
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (7)..(7)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 67

Arg Arg Xaa Cys Tyr Arg Xaa Xaa Pro Tyr Arg Xaa Cys Arg
1               5                   10

<210> SEQ ID NO 68
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 68
```

Arg Arg Xaa Cys Tyr Xaa Lys Xaa Pro Tyr Arg Xaa Cys Arg
1               5                   10

```
<210> SEQ ID NO 69
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 69
```

Arg Arg Xaa Cys Tyr Arg Lys Xaa Pro Tyr Arg Xaa Cys Arg
1               5                   10

```
<210> SEQ ID NO 70
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline

<400> SEQUENCE: 70
```

Arg Arg Xaa Cys Tyr Xaa Lys Xaa Pro Tyr Arg Xaa Cys Arg
1               5                   10

```
<210> SEQ ID NO 71
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline

<400> SEQUENCE: 71
```

```
Arg Arg Xaa Cys Tyr Arg Lys Xaa Pro Tyr Arg Xaa Cys Arg
1               5                   10
```

<210> SEQ ID NO 72
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: citrulline
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' Amidated

<400> SEQUENCE: 72

```
Xaa Arg Xaa Cys Tyr Arg Lys Xaa Pro Tyr Arg Xaa Cys Arg
1               5                   10
```

<210> SEQ ID NO 73
<211> LENGTH: 14
<212> TYPE: PRT
<213> ORGANISM: Artificial Sequence
<220> FEATURE:
<223> OTHER INFORMATION: SYNTHETIC FORMULA PEPTIDE
<220> FEATURE:
<221> NAME/KEY: MISC_FEATURE
<222> LOCATION: (1)..(1)
<223> OTHER INFORMATION: Xaa is Arg, Lys, ornithine, citrulline, Ala or
      Glu which may be derivatized at the N-terminal
<220> FEATURE:
<221> NAME/KEY: MISC_FEATURE
<222> LOCATION: (1)..(14)
<223> OTHER INFORMATION: L-amino acid or D-amino acid
<220> FEATURE:
<221> NAME/KEY: MISC_FEATURE
<222> LOCATION: (2)..(2)
<223> OTHER INFORMATION: When Xaa of (1) is Arg, Lys, ornithine,
      citrulline, Ala or Glu which may be derivatized at the N-terminal,
      Xaa is Arg or Glu, and when Xaa of (1) is absent, Xaa is Arg or
      Glu which may be derivatized at the N-terminal
<220> FEATURE:
<221> NAME/KEY: MISC_FEATURE
<222> LOCATION: (3)..(3)
<223> OTHER INFORMATION: Xaa is an aromatic amino acid residue
<220> FEATURE:
<221> NAME/KEY: DISULFID
<222> LOCATION: (4)..(13)
<223> OTHER INFORMATION: Cys at 4-position and Cys at 13-position may
      form a disulfid bond.
<220> FEATURE:
<221> NAME/KEY: MISC_FEATURE
<222> LOCATION: (6)..(6)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (7)..(7)
<223> OTHER INFORMATION: Xaa is Arg, Lys, ornithine, citrulline, Ala or
      Glu.
<220> FEATURE:
<221> NAME/KEY: MISC_FEATURE

```
<222> LOCATION: (8)..(8)
<223> OTHER INFORMATION: Xaa is Pro, Gly, ornithine, Lys, Ala,
      citrulline, Arg or Glu.
<220> FEATURE:
<221> NAME/KEY: MISC_FEATURE
<222> LOCATION: (9)..(9)
<223> OTHER INFORMATION: Xaa is Pro, Gly, ornithine, Lys, Ala,
      citrulline or Arg
<220> FEATURE:
<221> NAME/KEY: MISC_FEATURE
<222> LOCATION: (10)..(10)
<223> OTHER INFORMATION: Xaa is Tyr, Phe, Ala, naphthyl Ala, citrulline
      or Glu.
<220> FEATURE:
<221> NAME/KEY: MISC_FEATURE
<222> LOCATION: (11)..(11)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (12)..(12)
<223> OTHER INFORMATION: Xaa is Arg, Lys, citrulline or Glu.
<220> FEATURE:
<221> NAME/KEY: MISC_FEATURE
<222> LOCATION: (14)..(14)
<223> OTHER INFORMATION: Xaa is Arg, Glu, Lys or citrulline which may be
      derivatized at the C-terminal.

<400> SEQUENCE: 73

Xaa Xaa Xaa Cys Tyr Xaa Xaa Xaa Xaa Xaa Xaa Xaa Cys Xaa
1               5                   10

<210> SEQ ID NO 74
<211> LENGTH: 14
<212> TYPE: PRT
<213> ORGANISM: Artificial Sequence
<220> FEATURE:
<223> OTHER INFORMATION: synthetic formula peptide
<220> FEATURE:
<221> NAME/KEY: MISC_FEATURE
<222> LOCATION: (1)..(1)
<223> OTHER INFORMATION: Xaa is Arg, Ala or Citrulline
<220> FEATURE:
<221> NAME/KEY: MISC_FEATURE
<222> LOCATION: (3)..(3)
<223> OTHER INFORMATION: Xaa is Trp or naphtylalanine
<220> FEATURE:
<221> NAME/KEY: MISC_FEATURE
<222> LOCATION: (6)..(6)
<223> OTHER INFORMATION: Xaa is Arg, Ala or Citrulline
<220> FEATURE:
<221> NAME/KEY: MISC_FEATURE
<222> LOCATION: (7)..(7)
<223> OTHER INFORMATION: Xaa is Lys, Ala or Citrulline
<220> FEATURE:
<221> NAME/KEY: MISC_FEATURE
<222> LOCATION: (8)..(9)
<223> OTHER INFORMATION: These positions represent a dipeptide selected
      from: D-lysyl-proline, D-alanyl-proline, D-lysyl-alanine and
      D-citrullyl-proline
<220> FEATURE:
<221> NAME/KEY: MISC_FEATURE
<222> LOCATION: (10)..(10)
<223> OTHER INFORMATION: Xaa is Tyr or Ala
<220> FEATURE:
<221> NAME/KEY: MISC_FEATURE
<222> LOCATION: (11)..(11)
<223> OTHER INFORMATION: Xaa is Arg, Ala or Citrulline
<220> FEATURE:
<221> NAME/KEY: MISC_FEATURE
<222> LOCATION: (12)..(12)
<223> OTHER INFORMATION: Xaa is Citrulline

<400> SEQUENCE: 74

Xaa Arg Xaa Cys Tyr Xaa Xaa Xaa Xaa Xaa Xaa Xaa Cys Arg
1               5                   10
```

```
<210> SEQ ID NO 75
<211> LENGTH: 13
<212> TYPE: PRT
<213> ORGANISM: Artificial Sequence
<220> FEATURE:
<223> OTHER INFORMATION: synthetic formula peptide
<220> FEATURE:
<221> NAME/KEY: MISC_FEATURE
<222> LOCATION: (1)..(1)
<223> OTHER INFORMATION: Arg, Lys, Ala, ornithine, citrulline, any N-
      alpha-substituted derivative of these amino acids, or not present
<220> FEATURE:
<221> NAME/KEY: MISC_FEATURE
<222> LOCATION: (3)..(3)
<223> OTHER INFORMATION: Any aromatic amino acid
<220> FEATURE:
<221> NAME/KEY: MISC_FEATURE
<222> LOCATION: (6)..(7)
<223> OTHER INFORMATION: Each position independently represents Arg,
      Lys, Ala, ornithine or citrulline
<220> FEATURE:
<221> NAME/KEY: MISC_FEATURE
<222> LOCATION: (8)..(8)
<223> OTHER INFORMATION: D-citrulline, D-alanine, citrulline or alanine
<220> FEATURE:
<221> NAME/KEY: MISC_FEATURE
<222> LOCATION: (9)..(9)
<223> OTHER INFORMATION: Tyr, Phe, Ala, naphthylalanine or citrulline
<220> FEATURE:
<221> NAME/KEY: MISC_FEATURE
<222> LOCATION: (10)..(10)
<223> OTHER INFORMATION: Arg, Lys, Ala, ornithine or citrulline
<220> FEATURE:
<221> NAME/KEY: MISC_FEATURE
<222> LOCATION: (11)..(11)
<223> OTHER INFORMATION: citrulline
<220> FEATURE:
<221> NAME/KEY: MISC_FEATURE
<222> LOCATION: (13)..(13)
<223> OTHER INFORMATION: Lys or Arg; a carboxyl group may be amidated

<400> SEQUENCE: 75

Xaa Arg Xaa Cys Tyr Xaa Xaa Xaa Xaa Xaa Xaa Cys Xaa
1               5                   10

<210> SEQ ID NO 76
<211> LENGTH: 14
<212> TYPE: PRT
<213> ORGANISM: Artificial Sequence
<220> FEATURE:
<223> OTHER INFORMATION: synthetic formula peptide
<220> FEATURE:
<221> NAME/KEY: MISC_FEATURE
<222> LOCATION: (1)..(1)
<223> OTHER INFORMATION: Arg, Lys, Ala, ornithine, citrulline, any N-
      alpha-substituted derivative of these amino acids, or not present
<220> FEATURE:
<221> NAME/KEY: MISC_FEATURE
<222> LOCATION: (1)..(14)
<223> OTHER INFORMATION: this sequence is structured with the proviso
      that either of the amino acid residues at positions 1, 6, 7, 10,
      11 and 14 is Ala or citrulline
<220> FEATURE:
<221> NAME/KEY: MISC_FEATURE
<222> LOCATION: (3)..(3)
<223> OTHER INFORMATION: Any aromatic amino acid
<220> FEATURE:
<221> NAME/KEY: DISULFID
<222> LOCATION: (4)..(13)
<223> OTHER INFORMATION: Cys at 4-position and Cys at 13-position may
      form a disulfid bond.
<220> FEATURE:
<221> NAME/KEY: MISC_FEATURE
<222> LOCATION: (6)..(7)
<223> OTHER INFORMATION: Each position independently represents Arg,
      Lys, Ala, ornithine or citrulline
<220> FEATURE:
```

```
<221> NAME/KEY: MISC_FEATURE
<222> LOCATION: (8)..(9)
<223> OTHER INFORMATION: D-orn-pro, pro-D-orn, D-lys-pro, pro-D-lys,
      D-arg-pro, pro-D-arg, D-cit-pro, D-cit-ala, D-ala-cit, pro-D-cit,
      gly-orn, orn-gly, gly-lys, lys-gly, gly-arg, arg-gly, gly-cit,
      cit-gly, D-ala-pro or D-lys-ala
<220> FEATURE:
<221> NAME/KEY: MISC_FEATURE
<222> LOCATION: (10)..(10)
<223> OTHER INFORMATION: Tyr, Phe, Ala, naphthylalanine or citrulline
<220> FEATURE:
<221> NAME/KEY: MISC_FEATURE
<222> LOCATION: (11)..(11)
<223> OTHER INFORMATION: Arg, Lys, Ala, ornithine or citrulline
<220> FEATURE:
<221> NAME/KEY: MISC_FEATURE
<222> LOCATION: (14)..(14)
<223> OTHER INFORMATION: Lys or Arg; a carboxyl group may be amidated

<400> SEQUENCE: 76

Xaa Arg Xaa Cys Tyr Xaa Xaa Xaa Xaa Xaa Xaa Cys Xaa
1               5                   10

<210> SEQ ID NO 77
<211> LENGTH: 18
<212> TYPE: PRT
<213> ORGANISM: Artificial Sequence
<220> FEATURE:
<223> OTHER INFORMATION: synthetic formula peptide
<220> FEATURE:
<221> NAME/KEY: MISC_FEATURE
<222> LOCATION: (1)..(1)
<223> OTHER INFORMATION: Arg, Lys, Ala, ornithine, citrulline, any N-
      alpha-substituted derivative of these amino acids, or not present
<220> FEATURE:
<221> NAME/KEY: MISC_FEATURE
<222> LOCATION: (1)..(18)
<223> OTHER INFORMATION: this sequence is structured with the proviso
      that either of the amino acid residues at positions 1, 6, 7, 14,
      15 and 18 is Ala or citrulline
<220> FEATURE:
<221> NAME/KEY: MISC_FEATURE
<222> LOCATION: (3)..(3)
<223> OTHER INFORMATION: Any aromatic amino acid
<220> FEATURE:
<221> NAME/KEY: DISULFID
<222> LOCATION: (4)..(17)
<223> OTHER INFORMATION: Cys at 4-position and Cys at 17-position may
      form a disulfid bond.
<220> FEATURE:
<221> NAME/KEY: MISC_FEATURE
<222> LOCATION: (6)..(7)
<223> OTHER INFORMATION: Each position independently represents Arg,
      Lys, Ala, ornithine or citrulline
<220> FEATURE:
<221> NAME/KEY: MISC_FEATURE
<222> LOCATION: (8)..(8)
<223> OTHER INFORMATION: Ala, Val, Leu, Ile, Ser, Cys or Met
<220> FEATURE:
<221> NAME/KEY: DISULFID
<222> LOCATION: (8)..(13)
<223> OTHER INFORMATION: when positions 8 and 13 are Cys, they may form
      a disulfide bond
<220> FEATURE:
<221> NAME/KEY: MISC_FEATURE
<222> LOCATION: (9)..(9)
<223> OTHER INFORMATION: Any aromatic amino acid
<220> FEATURE:
<221> NAME/KEY: MISC_FEATURE
<222> LOCATION: (10)..(10)
<223> OTHER INFORMATION: Arg, Lys, Ala, ornithine or citrulline
<220> FEATURE:
<221> NAME/KEY: MISC_FEATURE
<222> LOCATION: (12)..(12)
<223> OTHER INFORMATION: Tyr, Phe, Trp, Ala, Val, Leu, Ile, Ser, Cys or
      Met
<220> FEATURE:
<221> NAME/KEY: MISC_FEATURE
```

```
<222> LOCATION: (13)..(13)
<223> OTHER INFORMATION: Ala, Val, Leu, Ile, Ser, Cys or Met

<400> SEQUENCE: 77

Xaa Arg Xaa Cys Tyr Xaa Xaa Xaa Xaa Xaa Gly Xaa Xaa Xaa Xaa Xaa
1               5                   10                  15

Cys Xaa

<210> SEQ ID NO 78
<211> LENGTH: 25
<212> TYPE: DNA
<213> ORGANISM: Artificial Sequence
<220> FEATURE:
<223> OTHER INFORMATION: PCR primer

<400> SEQUENCE: 78
uaaaaucuuc cugcccacca ucuac                                          25

<210> SEQ ID NO 79
<211> LENGTH: 27
<212> TYPE: DNA
<213> ORGANISM: Artificial Sequence
<220> FEATURE:
<223> OTHER INFORMATION: PCR primer

<400> SEQUENCE: 79
guagauggug ggcaggaaga uuuuauu                                        27

<210> SEQ ID NO 80
<211> LENGTH: 20
<212> TYPE: DNA
<213> ORGANISM: Artificial Sequence
<220> FEATURE:
<223> OTHER INFORMATION: PCR primer

<400> SEQUENCE: 80
ccctggactt cgagcaagag                                                20

<210> SEQ ID NO 81
<211> LENGTH: 20
<212> TYPE: DNA
<213> ORGANISM: Artificial Sequence
<220> FEATURE:
<223> OTHER INFORMATION: PCR primer

<400> SEQUENCE: 81
tctccttctg catcctgtcg                                                20

<210> SEQ ID NO 82
<211> LENGTH: 20
<212> TYPE: DNA
<213> ORGANISM: Artificial Sequence
<220> FEATURE:
<223> OTHER INFORMATION: PCR primer

<400> SEQUENCE: 82
atgtgctgta ccaagagttt                                                20

<210> SEQ ID NO 83
<211> LENGTH: 20
<212> TYPE: DNA
<213> ORGANISM: Artificial Sequence
<220> FEATURE:
<223> OTHER INFORMATION: PCR primer

<400> SEQUENCE: 83
```
caagtctgtt ttggatttgc                                                    20

<210> SEQ ID NO 84
<211> LENGTH: 20
<212> TYPE: DNA
<213> ORGANISM: Artificial Sequence
<220> FEATURE:
<223> OTHER INFORMATION: PCR primer

<400> SEQUENCE: 84
ccattctggg cagtgagtca                                                    20

<210> SEQ ID NO 85
<211> LENGTH: 19
<212> TYPE: DNA
<213> ORGANISM: Artificial Sequence
<220> FEATURE:
<223> OTHER INFORMATION: PCR primer

<400> SEQUENCE: 85
agcagcatcc cgcagttaa                                                     19

<210> SEQ ID NO 86
<211> LENGTH: 27
<212> TYPE: DNA
<213> ORGANISM: Artificial Sequence
<220> FEATURE:
<223> OTHER INFORMATION: PCR primer

<400> SEQUENCE: 86
agctgttggc tgaaaaggtg gtctatg                                            27

<210> SEQ ID NO 87
<211> LENGTH: 26
<212> TYPE: DNA
<213> ORGANISM: Artificial Sequence
<220> FEATURE:
<223> OTHER INFORMATION: PCR primer

<400> SEQUENCE: 87
gcgcttctgg tggcccttgg agtgtg                                             26

<210> SEQ ID NO 88
<211> LENGTH: 22
<212> TYPE: DNA
<213> ORGANISM: Artificial Sequence
<220> FEATURE:
<223> OTHER INFORMATION: PCR primer

<400> SEQUENCE: 88
atgaacgcca aggtcgtggt cg                                                 22

<210> SEQ ID NO 89
<211> LENGTH: 19
<212> TYPE: DNA
<213> ORGANISM: Artificial Sequence
<220> FEATURE:
<223> OTHER INFORMATION: PCR primer

<400> SEQUENCE: 89
tgttgttgtt cttcagccg                                                     19

The invention claimed is:

1. A method for stimulating or enhancing in a subject in need thereof an immune response to an antigen, comprising administering to the subject: i) an immunogenic amount of the antigen, or a recombinant construct comprising a nucleic acid sequence encoding the antigen, the nucleic acid sequence being operably linked to at least one transcription control sequence, and ii) an immunogenicity-augmenting amount of a peptide as set forth in SEQ ID NO:1 in concurrent or sequential combination with said antigen.

2. The method of claim 1, wherein said antigen is selected from the group consisting of a tumor-associated antigen, a viral antigen, a bacterial antigen, a fungal antigen and a parasite-derived antigen.

* * * * *